United States Patent
Kang et al.

(10) Patent No.: US 12,202,893 B2
(45) Date of Patent: Jan. 21, 2025

(54) ANTIBODY COMPOSITIONS COMPRISING Fc MUTATIONS AND SITE-SPECIFIC CONJUGATION PROPERTIES FOR USE IN TREATING CANCER, IMMUNOLOGICAL DISORDERS, AND METHODS THEREOF

(71) Applicant: TAE Life Sciences, Foot Hill Ranch, CA (US)

(72) Inventors: Sohye Kang, Torrance, CA (US); Morrison Kendall, Santa Monica, CA (US)

(73) Assignee: TAE Life Sciences, LLC, Irvine, CA (US)

(*) Notice: Subject to any disclaimer, the term of this patent is extended or adjusted under 35 U.S.C. 154(b) by 255 days.

(21) Appl. No.: 16/974,114

(22) Filed: Oct. 2, 2020

(65) Prior Publication Data

US 2023/0165967 A1    Jun. 1, 2023

Related U.S. Application Data

(60) Provisional application No. 62/973,475, filed on Oct. 4, 2019.

(51) Int. Cl.
| | |
|---|---|
| C07K 16/28 | (2006.01) |
| A61K 47/68 | (2017.01) |
| A61P 35/00 | (2006.01) |
| C07K 16/30 | (2006.01) |
| C07K 16/32 | (2006.01) |

(52) U.S. Cl.
CPC ........ *C07K 16/28* (2013.01); *A61K 47/68031* (2023.08); *A61K 47/6851* (2017.08);
(Continued)

(58) Field of Classification Search
CPC . A61K 47/6803; A61K 47/6851; A61P 35/00; C07K 16/28; C07K 16/2863;
(Continued)

(56) References Cited

U.S. PATENT DOCUMENTS

| | | |
|---|---|---|
| 7,910,099 B2 | 3/2011 | Karpusas et al. |
| 8,415,338 B2 | 4/2013 | Blanchard et al. |

(Continued)

FOREIGN PATENT DOCUMENTS

| | | |
|---|---|---|
| WO | WO 2018/160683 | 9/2018 |
| WO | WO-2019079357 A1 * | 4/2019 |

OTHER PUBLICATIONS

Tilman Schlothauer, Sylvia Herter, Claudia Ferrara Koller, Sandra Grau-Richards, Virginie Steinhart, Christian Spick, Manfred Kubbies, Christian Klein, Pablo Umana, Ekkehard Mossner. Protein Engineering, Design and Selection, vol. 29, Issue 10, Oct. 2016, pp. 457-466. (Year: 2016).*

(Continued)

*Primary Examiner* — Adam Weidner
*Assistant Examiner* — Laura Ann Essex
(74) *Attorney, Agent, or Firm* — LOSMP; Shane M. Popp

(57) ABSTRACT

Antibodies that bind Her2, EGFR, Trop2, CDH3 or other TAAs containing a triple mutation at L234A, L235A, and L328C and methods of making such triple mutated antibodies are disclosed herein. Consequently, the triple mutated antibodies contain a modified effector function through Fc silencing and are capable of site-specific conjugation at L328C to form an antibody-drug-conjugate (ADC) which can be administered to patients and provide a method of treating cancer, immunological and neurological disorders.

33 Claims, 61 Drawing Sheets

Specification includes a Sequence Listing.

Anti-HER2 mAb and Fc variants: A complete inhibition of FcγRI binding is observed for the triple mutant

(52) U.S. Cl.
CPC .......... *A61P 35/00* (2018.01); *C07K 16/2863* (2013.01); *C07K 16/30* (2013.01); *C07K 16/32* (2013.01); *C07K 2317/524* (2013.01); *C07K 2317/526* (2013.01); *C07K 2317/71* (2013.01)

(58) Field of Classification Search
CPC .. C07K 16/30; C07K 16/32; C07K 2317/524; C07K 2317/526; C07K 2317/71
See application file for complete search history.

(56) References Cited

U.S. PATENT DOCUMENTS

| | | | |
|---|---|---|---|
| 8,734,791 | B2 | 5/2014 | Lazar et al. |
| 8,969,526 | B2 | 3/2015 | Baehner et al. |
| 9,133,214 | B2 | 9/2015 | Blanchard et al. |
| 9,328,170 | B2 | 5/2016 | Zha |
| 9,546,203 | B2 | 1/2017 | Kannan |
| 9,573,964 | B2 | 2/2017 | Blanchard et al. |
| 9,657,106 | B2 * | 5/2017 | Lazar ............... A61P 43/00 |
| 10,053,513 | B2 | 8/2018 | McCarthy et al. |
| 11,180,554 | B2 | 11/2021 | Sato et al. |
| 11,236,168 | B2 | 2/2022 | Igawa et al. |
| 2004/0209895 | A1 | 10/2004 | Luecking et al. |
| 2014/0086916 | A1 | 3/2014 | Zha |
| 2014/0093496 | A1 | 4/2014 | Mimoto et al. |
| 2014/0105889 | A1 | 4/2014 | Igawa et al. |
| 2015/0203577 | A1 | 7/2015 | Igawa et al. |
| 2017/0080103 | A1 | 3/2017 | Ariaans et al. |
| 2017/0204116 | A1 | 7/2017 | Gray et al. |
| 2019/0054319 | A1 | 2/2019 | Wang et al. |
| 2020/0071404 | A1 | 3/2020 | Sato et al. |
| 2020/0199241 | A1 | 6/2020 | Igawa et al. |
| 2020/0277399 | A1 * | 9/2020 | Wozniak-Knopp ......................... C07K 16/2863 |

OTHER PUBLICATIONS

Hezarah, et. al., Effector Function Activities of a Panel of Mutants of a Broadly Neutralixing Antibody against . . . , J. Virology, vol. 75, No. 24, pp. 12161-12168 (Dec. 2001).

Wu, et. al., Site-Specific Conjugation of Boron-Containing Dendrimers to Anti-EGF Receptor Monoclonal Antibody Cetuximab . . . , Bioconjugate Chem., vol. 15, No. 1 (2004).

Deonarain, et. al., Emerging Formats for Next-Generation Drug Conjugates, Expert Opin. Drug Dicov. (2015) 10(5).

Hoffmann, et. al., Antibody Structure and Engineering Considerations for the Design and Function of Antibody Drug Conjugates (ADCs), Oncoimmunology, vol. 7, No. 3 (2018).

Jacobsen, et. al., Engineering an IgG Scaffold Lacking Effector Function with Optimized Developability, J. Bio. Chem., vol. 292, No. 5 (Feb. 3, 2017).

Schumacher, et. al., Current Status: Site-Specific Antibody Drug Conjugates, J. Clin Immunol (2016) 36 (Suppl 1):S100-S107.

Panowski, et. al., Site-specific Antibody Drug Conjugates for Cancer Therapy, mAbs 6:1, 34-45 (Jan./Feb. 2014).

Zhou, Qun, Site-Specific Antibody Conjugation for ADC and Beyond, Biomedicines 2017, 5, 64.

Wang, et. al., IgG Fc Engineering to Modulate Antibody Effector Functions, Protein Cell 2018, 9(1):63-73.

Saunders, Kevin, Conceptual Approaches to Modulating Antibody Effector Functions and Circulation Half-Life, Front. Immunol. 10:1296 (2019).

Schlothauer, et. al., Novel Human IgG1 and IgG4 Fc-Engineered Antibodies with Completely Abolished Immune . . . , Pro. Eng., Design & Sel., 2016, vol. 29, No. 10, pp. 457-466.

Sussman, et. al., Engineered Cysteine Antibodies: An Improved Antibody-Drug Conjugate Platform with a Novel . . . , Pro. Eng., Design & Sel., 2017, vol. 31, No. 2, pp. 47-54.

Tam, et. al., Functional; Biophysical, and Structural Characterization of Human IgG1 and IgG4 Fc Variants with Ablated Immune . . . , Antibodies (2017), 6, 12, pp. 1-34.

Weber, et. al., First Infusion Reactions are Mediated by FcγRIIIb and Neutrophils, Pharm. Res. (2018) 35:169, pp. 1-11.

Wines, et. al., The IgG Fc Contains Distinct Fc Receptor (FcR) Binding Sites: The Leukocyte Receptors FcγRI and FcγRIIa Bind to . . . , J. Immunol 2000; 164:5313-5318.

Bhat, et. al., The Next Step in Homogeneous Bioconjugate Development: Optimizing Payload Placement and Conjugate Composition, Bioprocess Int. 12(9)s pp. 1-7 (Oct. 2014).

\* cited by examiner

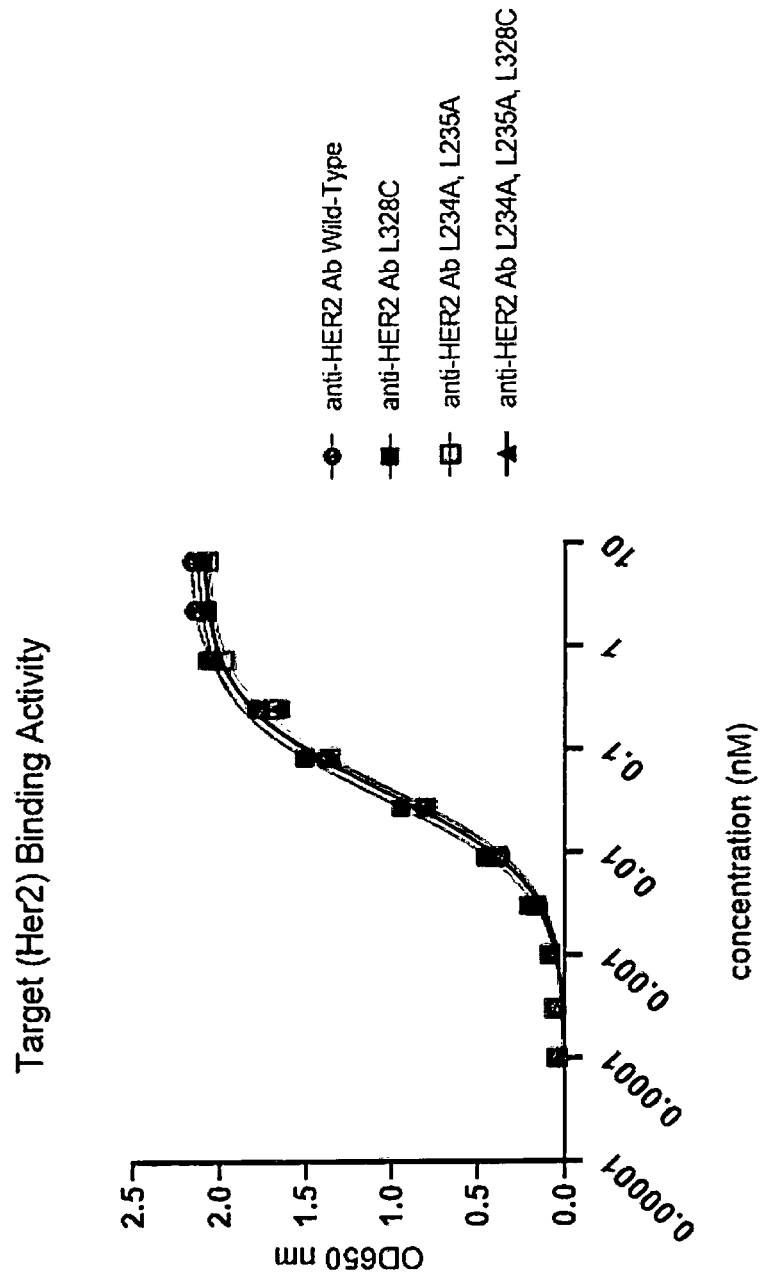
Figure 1. Anti-HER2 mAb and Fc variants: Fc variants do not affect target binding

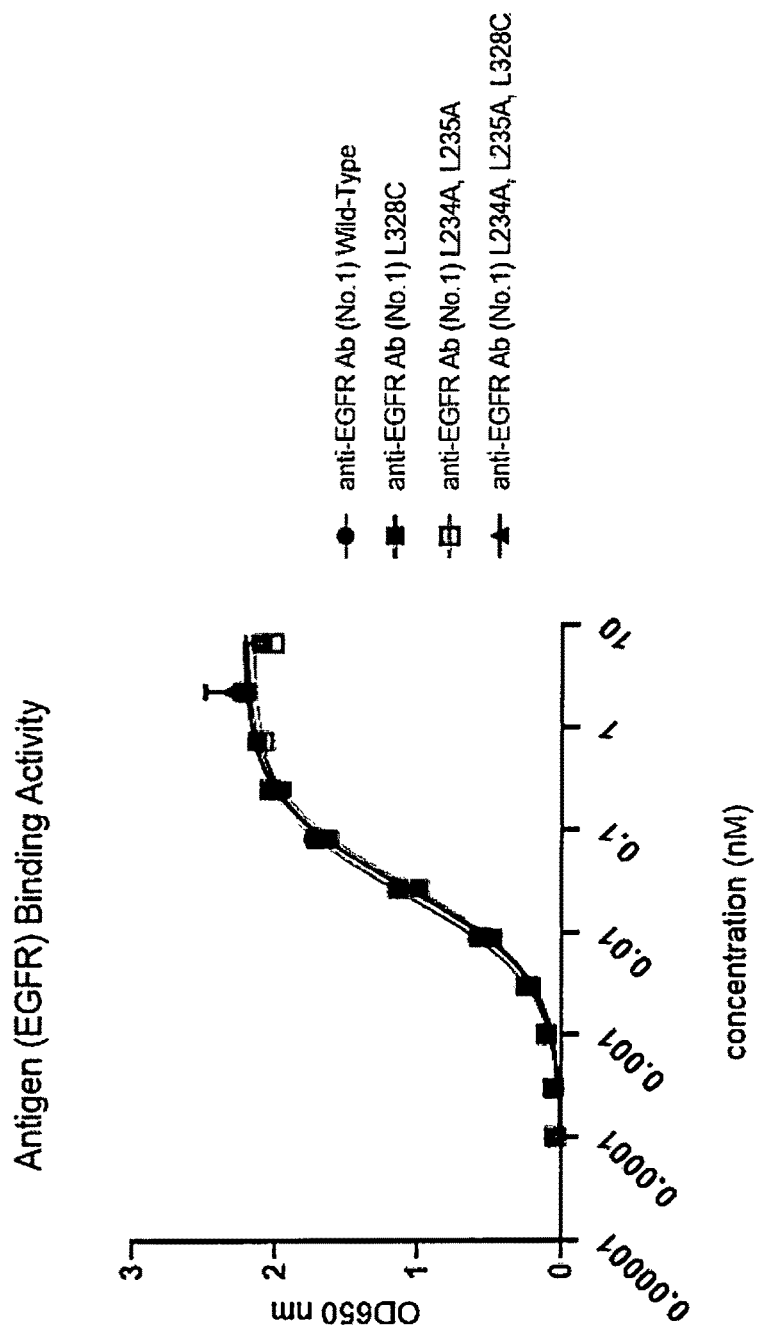
Figure 2. Anti-EGFR mAb No. 1 and Fc variants: Fc variants do not affect target binding

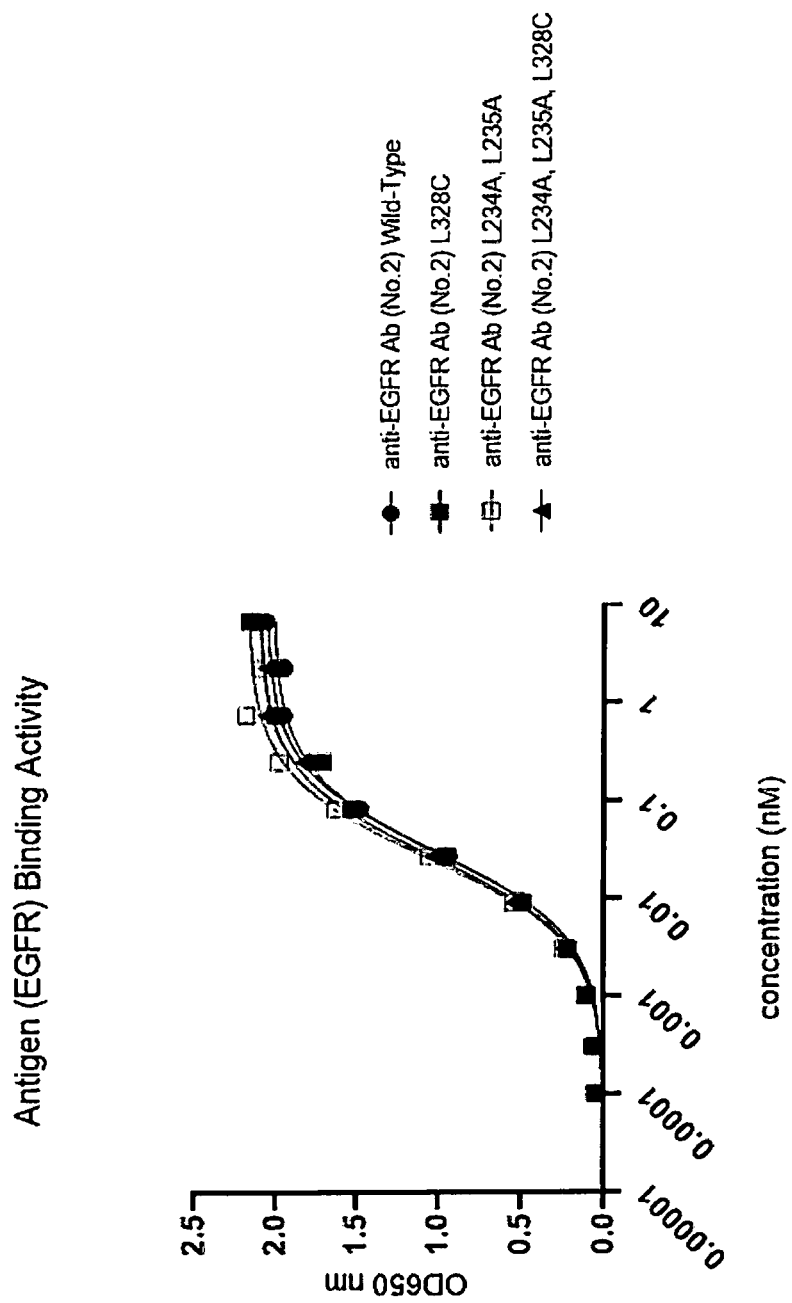
Figure 3. Anti-EGFR mAb No. 2 and Fc variants: Fc variants do not affect target binding

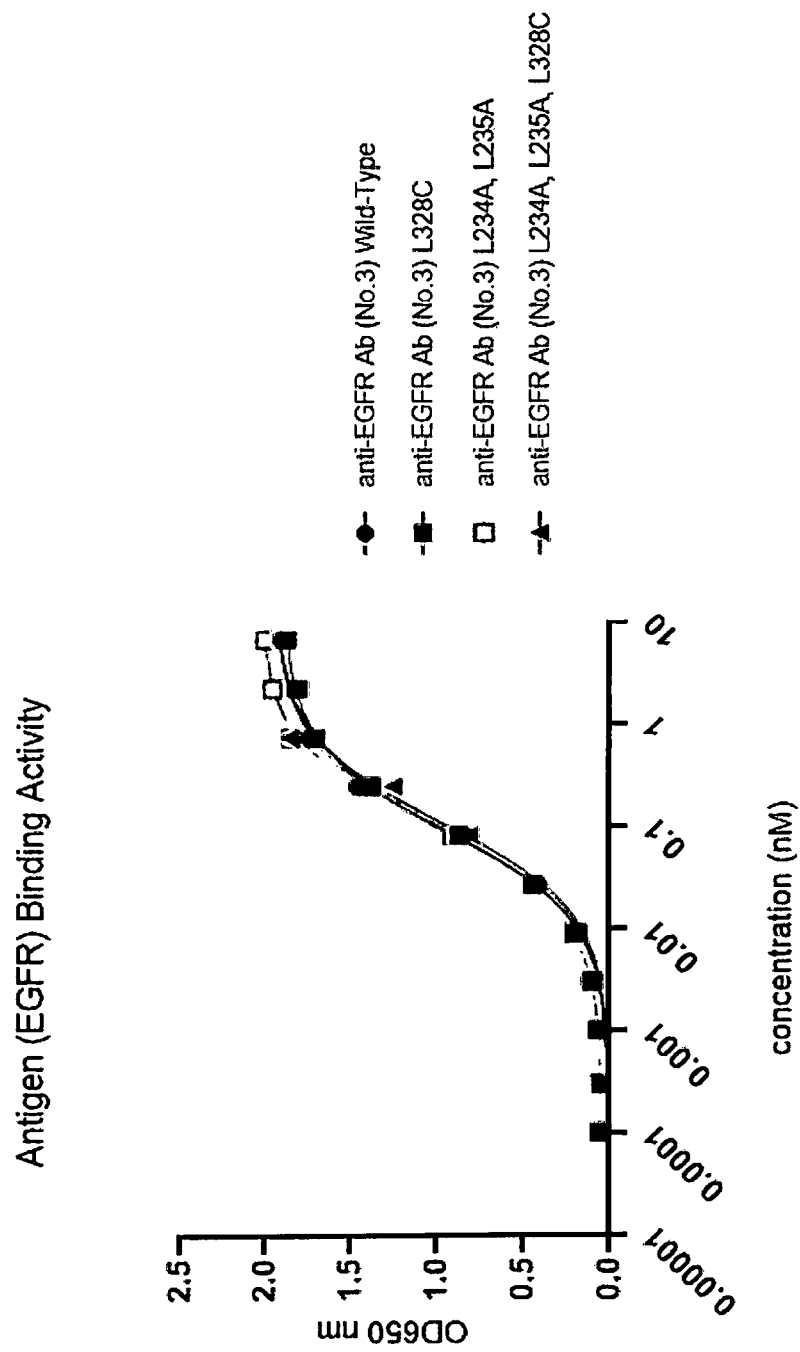
Figure 4. Anti-EGFR mAb No. 3 and Fc variants: Fc variants do not affect target binding

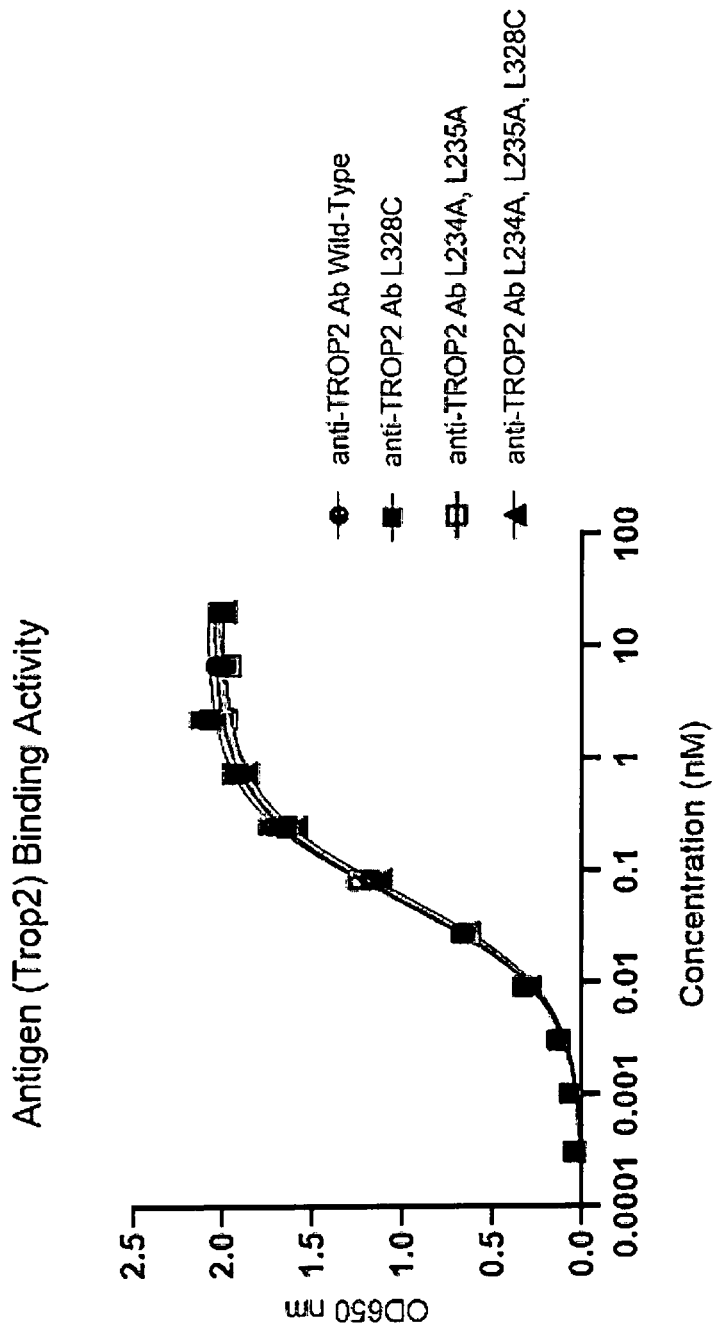
Figure 5. Anti-Trop2 mAb and Fc variants: Fc variants do not affect target binding

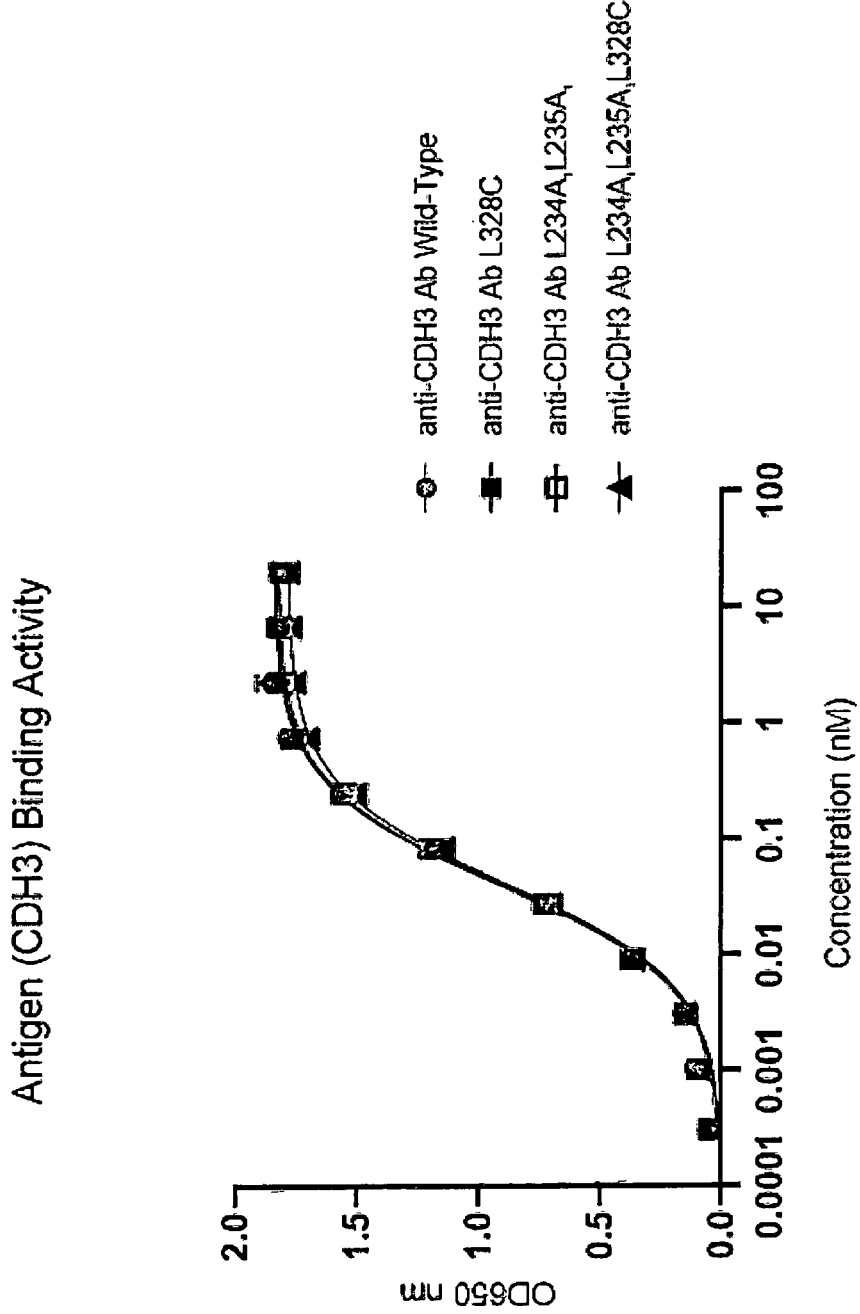
Figure 6. Anti-CDH3 mAb and Fc variants: Fc variants do not affect target binding

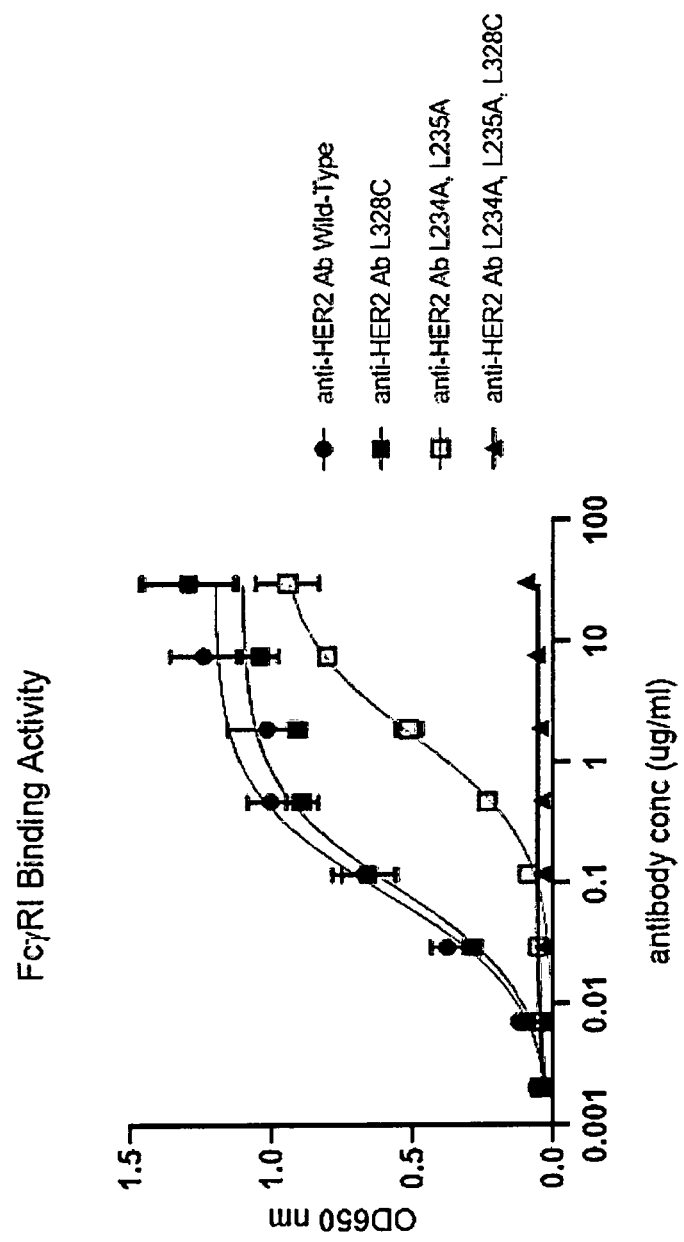
Figure 7. Anti-HER2 mAb and Fc variants: A complete inhibition of FcγRI binding is observed for the triple mutant

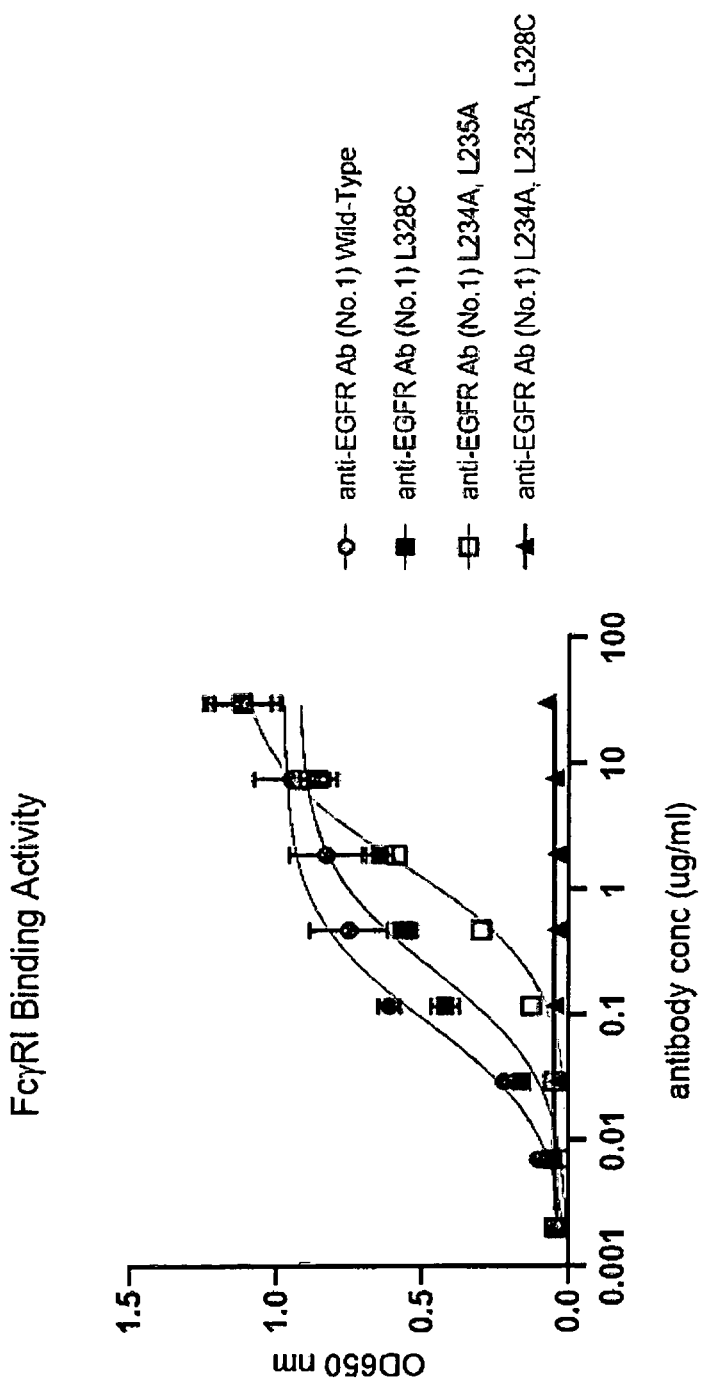
Figure 8. Anti-EGFR mAb No. 1 and Fc variants: A complete inhibition of FcγRI binding is observed for the triple mutant

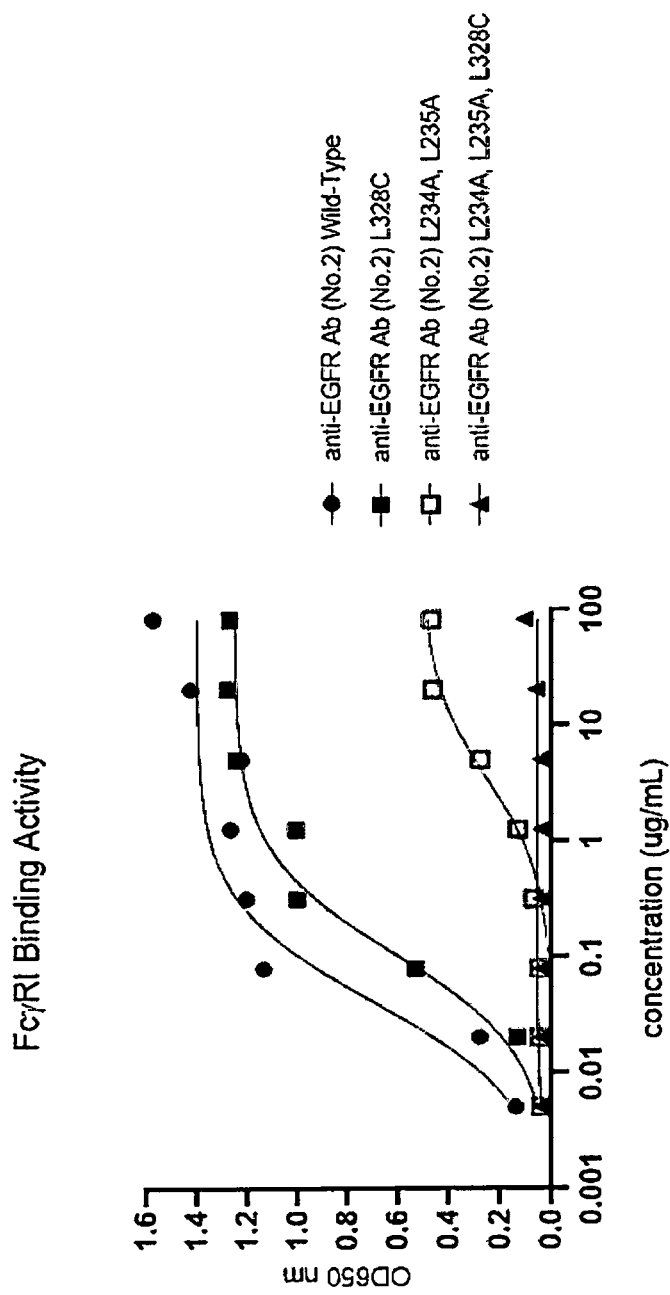
Figure 9. Anti-EGFR mAb No. 2 and Fc variants: A complete inhibition of FcγRI binding is observed for the triple mutant

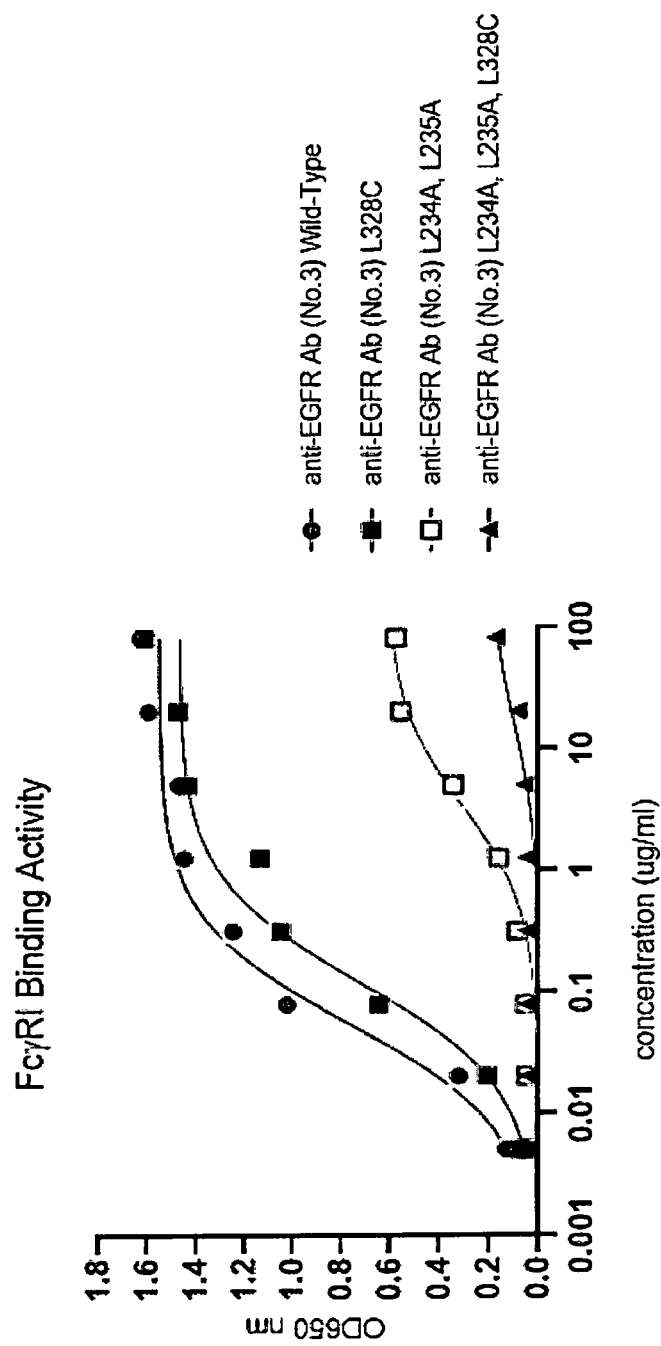
Figure 10. Anti-EGFR mAb No. 3 and Fc variants: A near complete inhibition of FcγRI binding is observed for the triple mutant

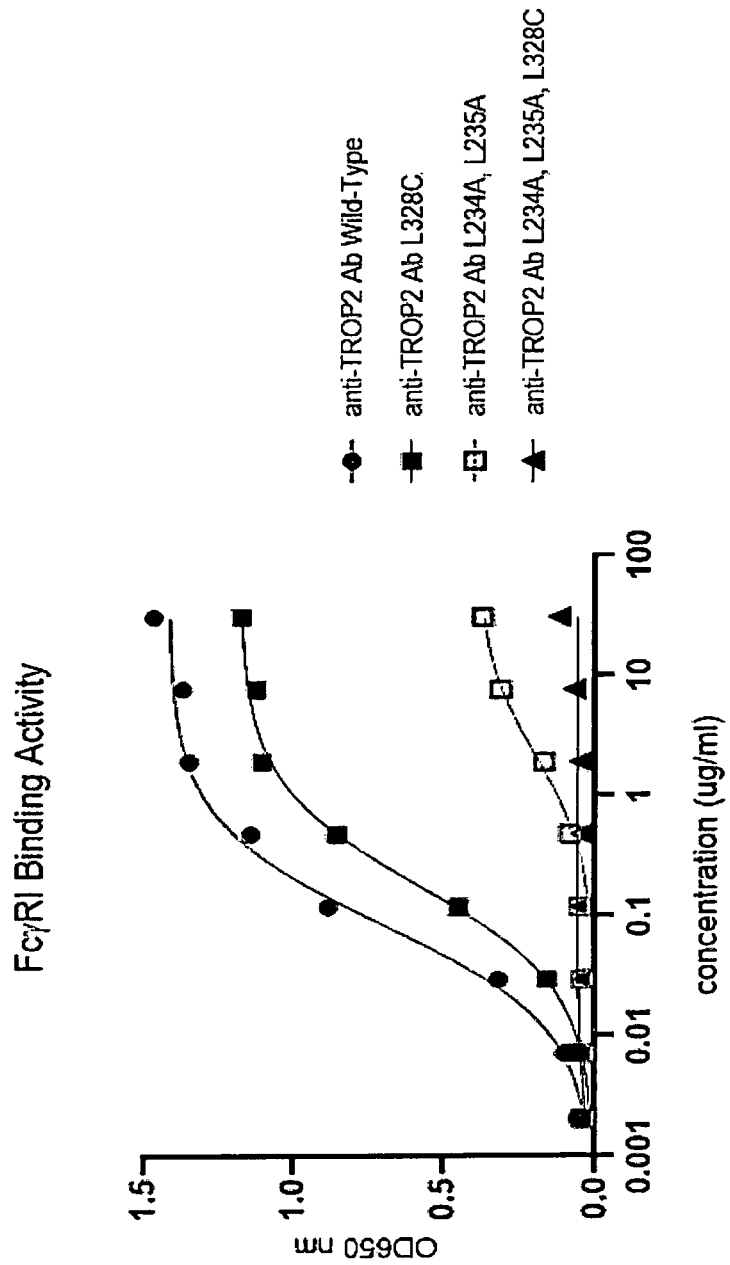
Figure 11. Anti-Trop2 mAb and Fc variants: A complete inhibition of FcγRI binding is observed for the triple mutant

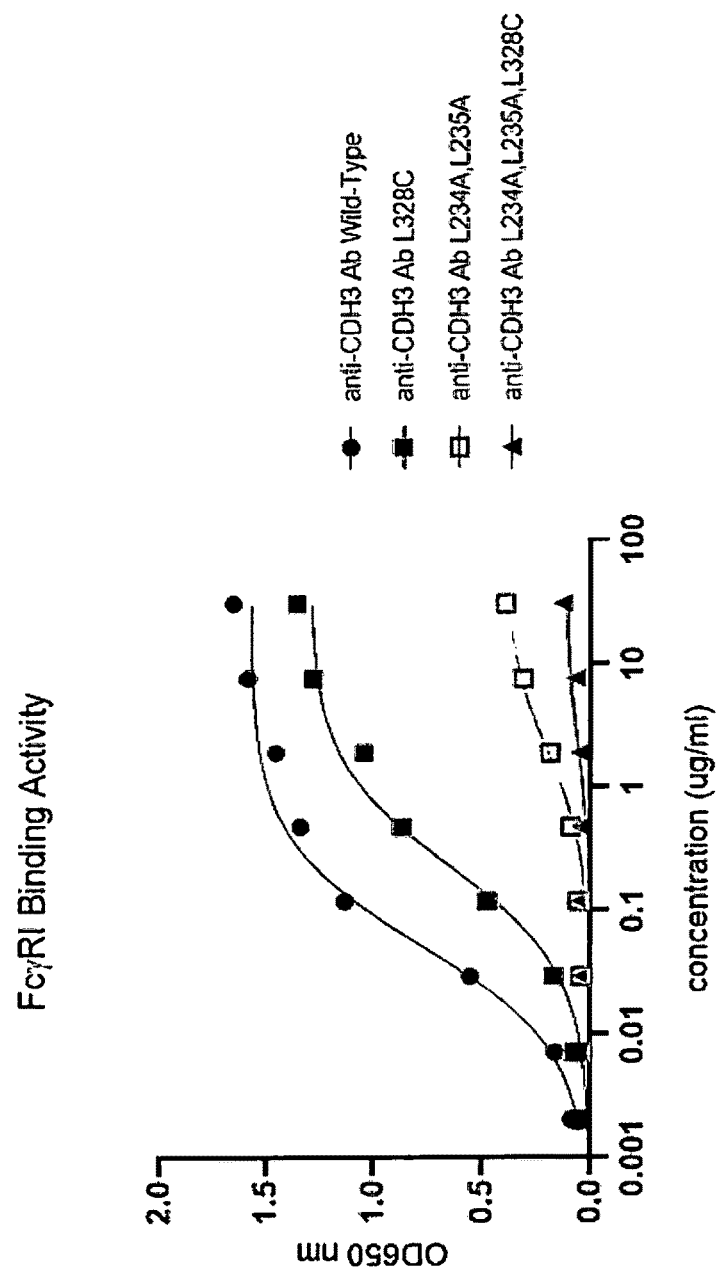
Figure 12. Anti-CDH3 mAb and Fc variants: A near complete inhibition of FcγRI binding is observed for the triple mutant

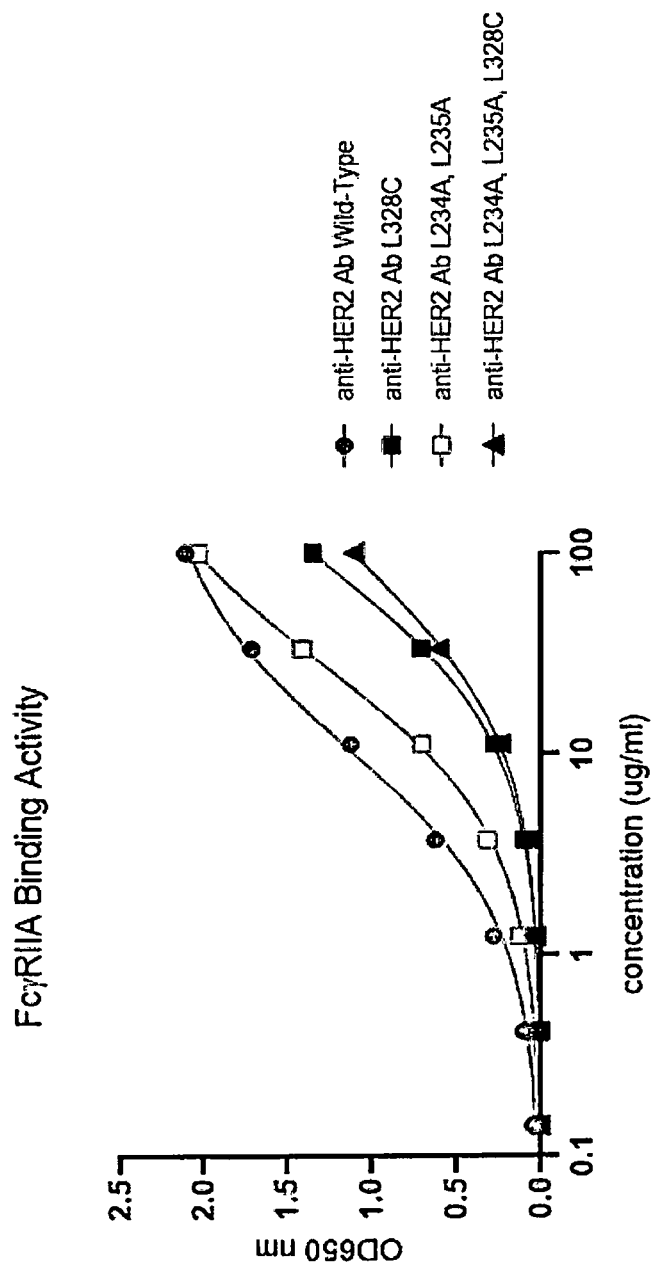
Figure 13. Anti-HER2 mAb and Fc variants: Suppression of FcγRIIA binding is observed for the single and triple mutants

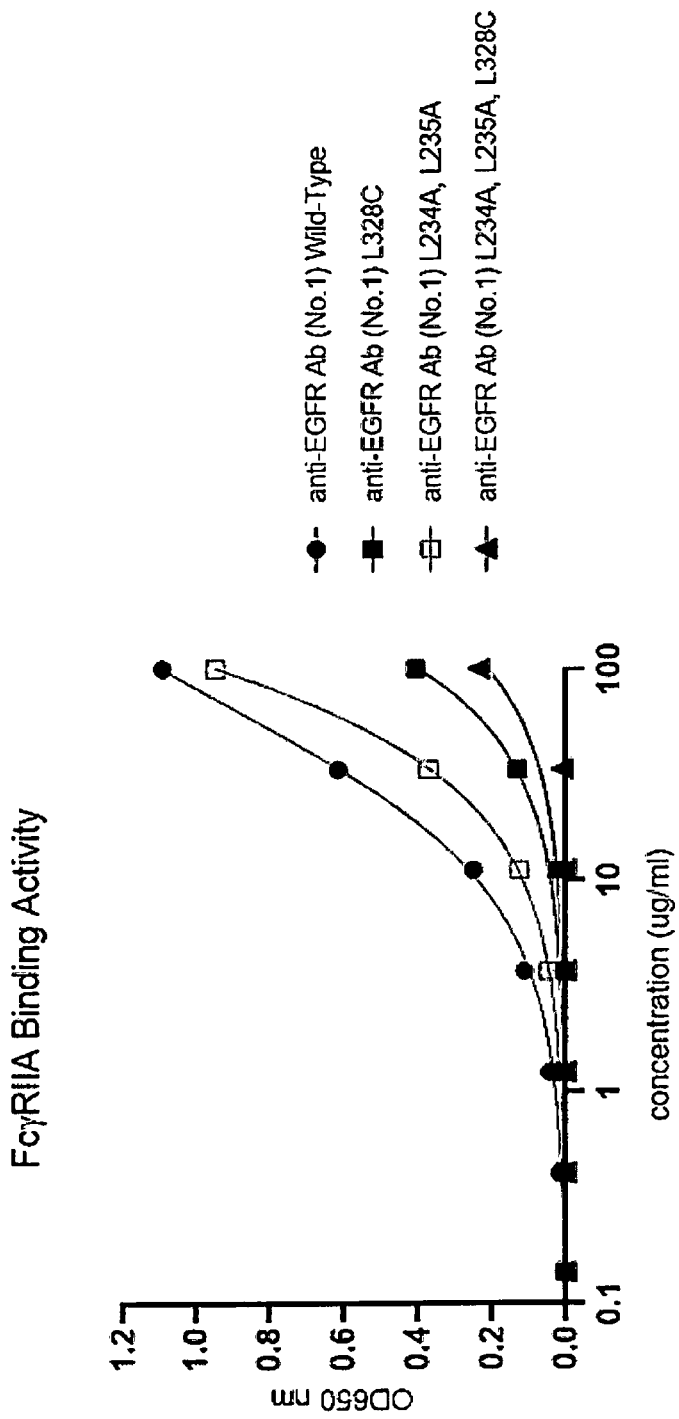
Figure 14. Anti-EGFR mAb No. 1 and Fc variants: Suppression of FcγRIIA binding is observed for the single and triple mutants

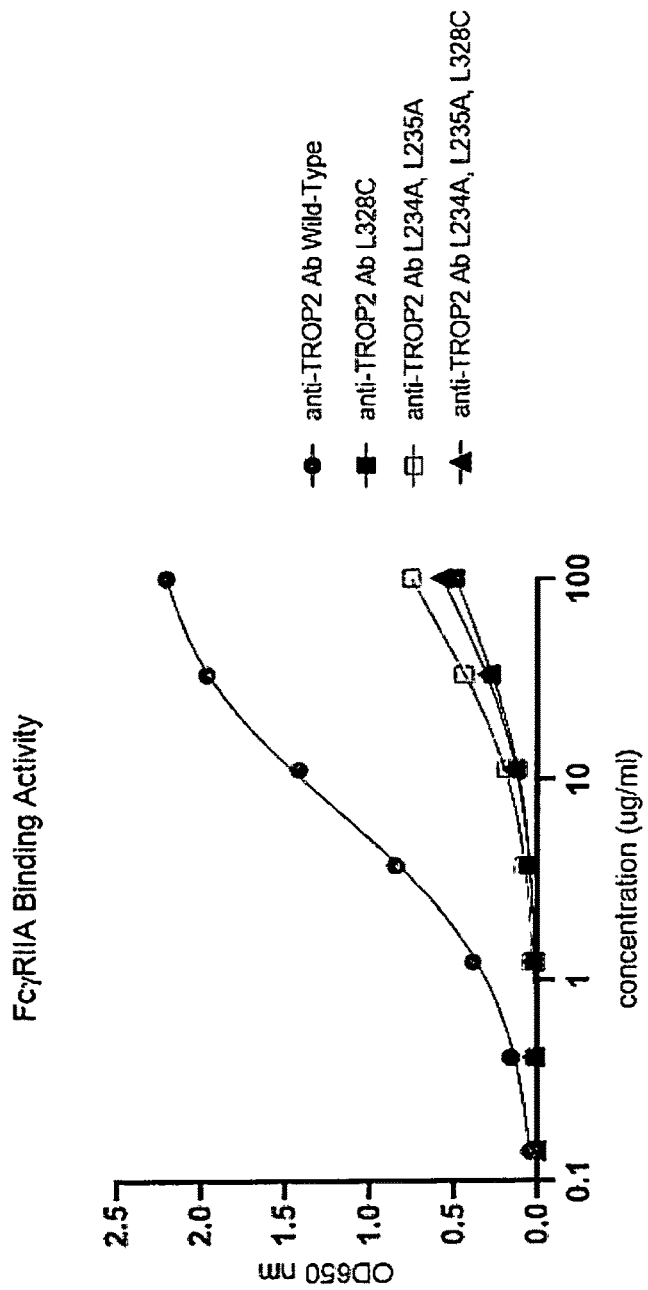
Figure 15. Anti-TROP2 mAb and Fc variants: Suppression of FcγRIIA binding is observed for the single, double and triple mutants

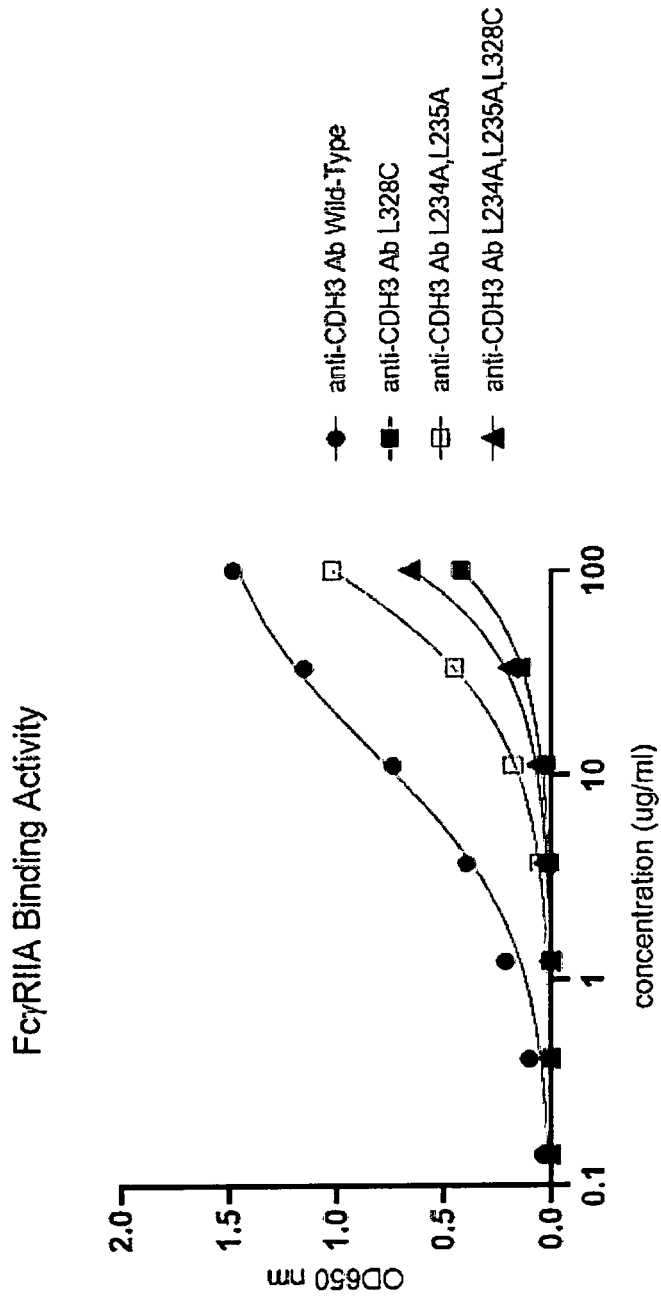
Figure 16. Anti-CDH3 mAb and Fc variants: Suppression of FcγRIIA binding is observed for the single, double and triple mutants

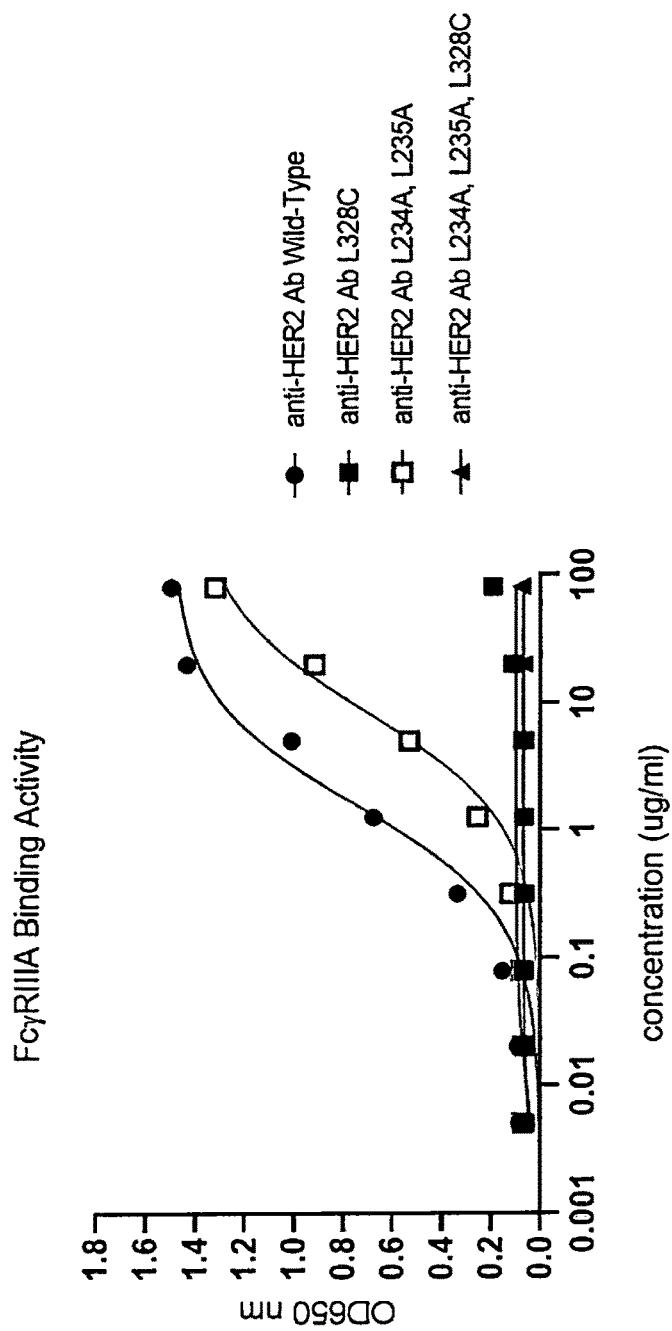
Figure 17. Anti-HER2 mAb and Fc variants: An inhibition of FcγRIIIA binding is observed for the single & triple mutant

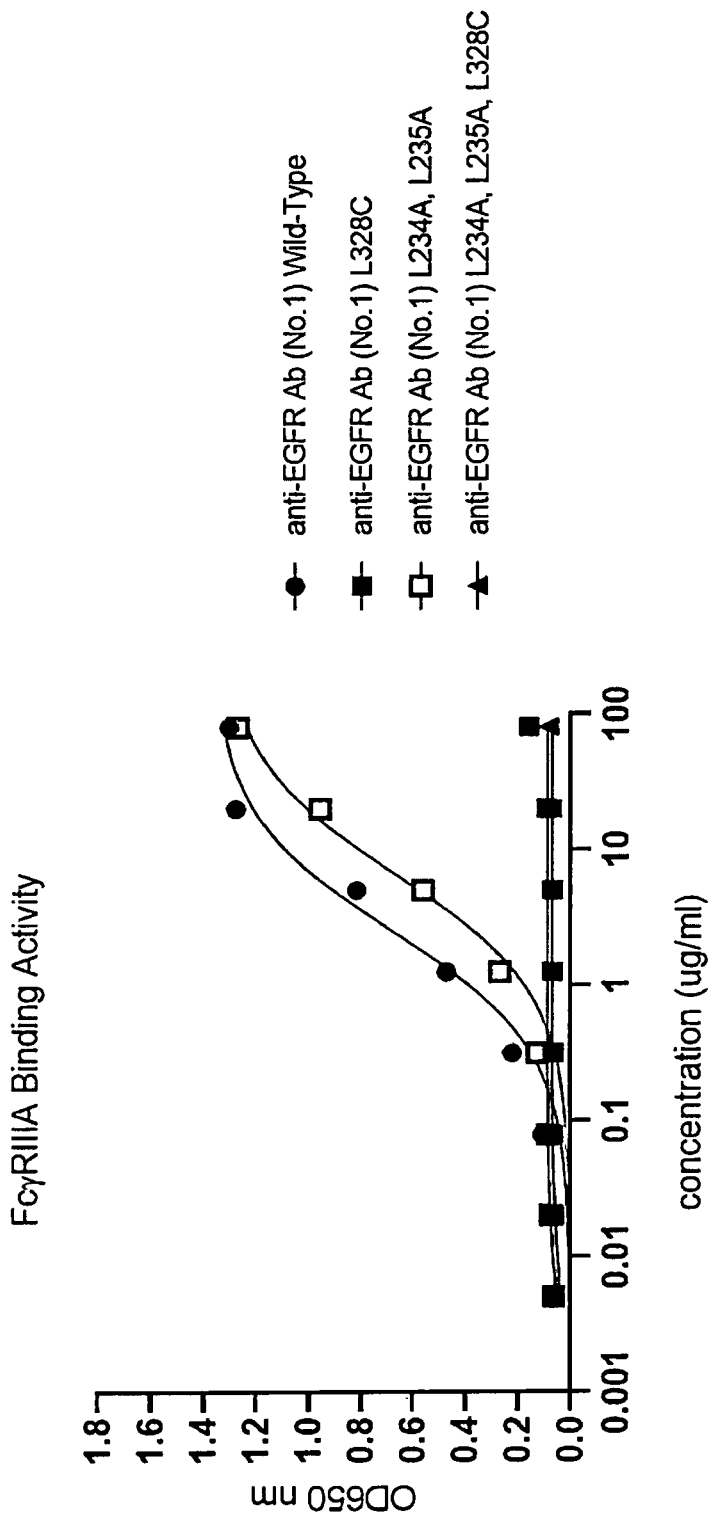
Figure 18. Anti-EGFR mAb No. 1 and Fc variants: An inhibition of FcγRIIIA binding is observed for the single & triple mutant

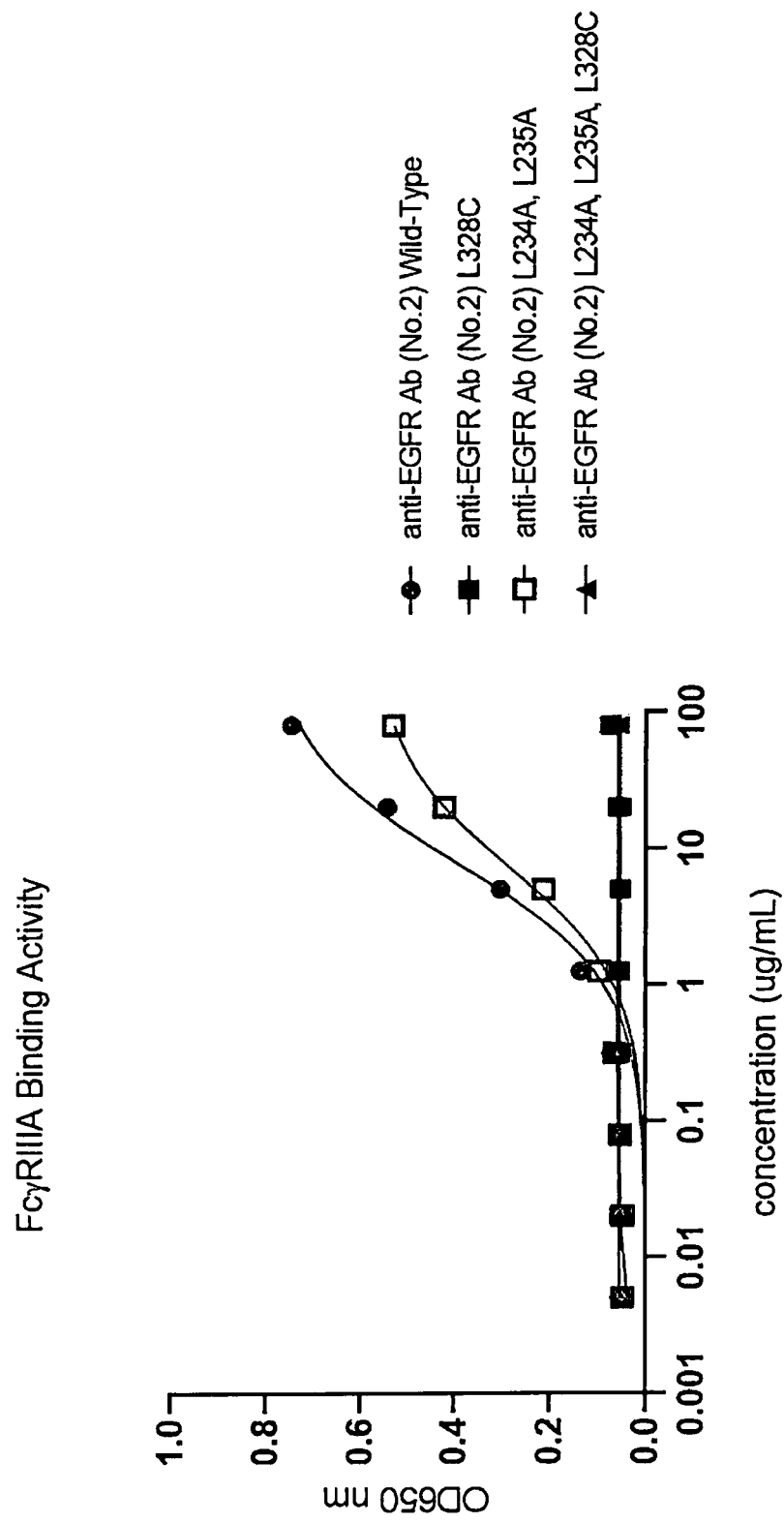
Figure 19. Anti-EGFR mAb No. 2 and Fc variants: An inhibition of FcγRIIIA binding is observed for the single & triple mutant

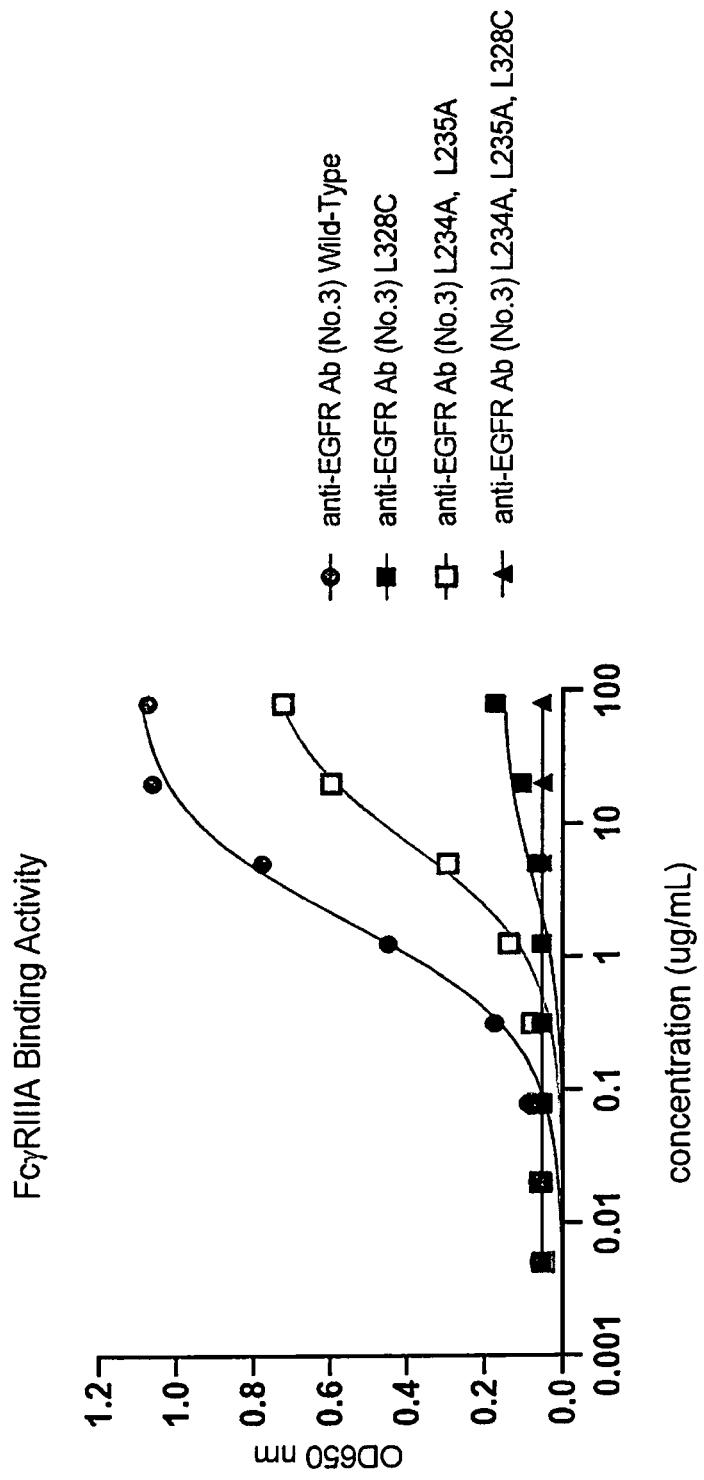
Figure 20. Anti-EGFR mAb No. 3 and Fc variants: An inhibition of FcγRIIIA binding is observed for the single & triple mutant

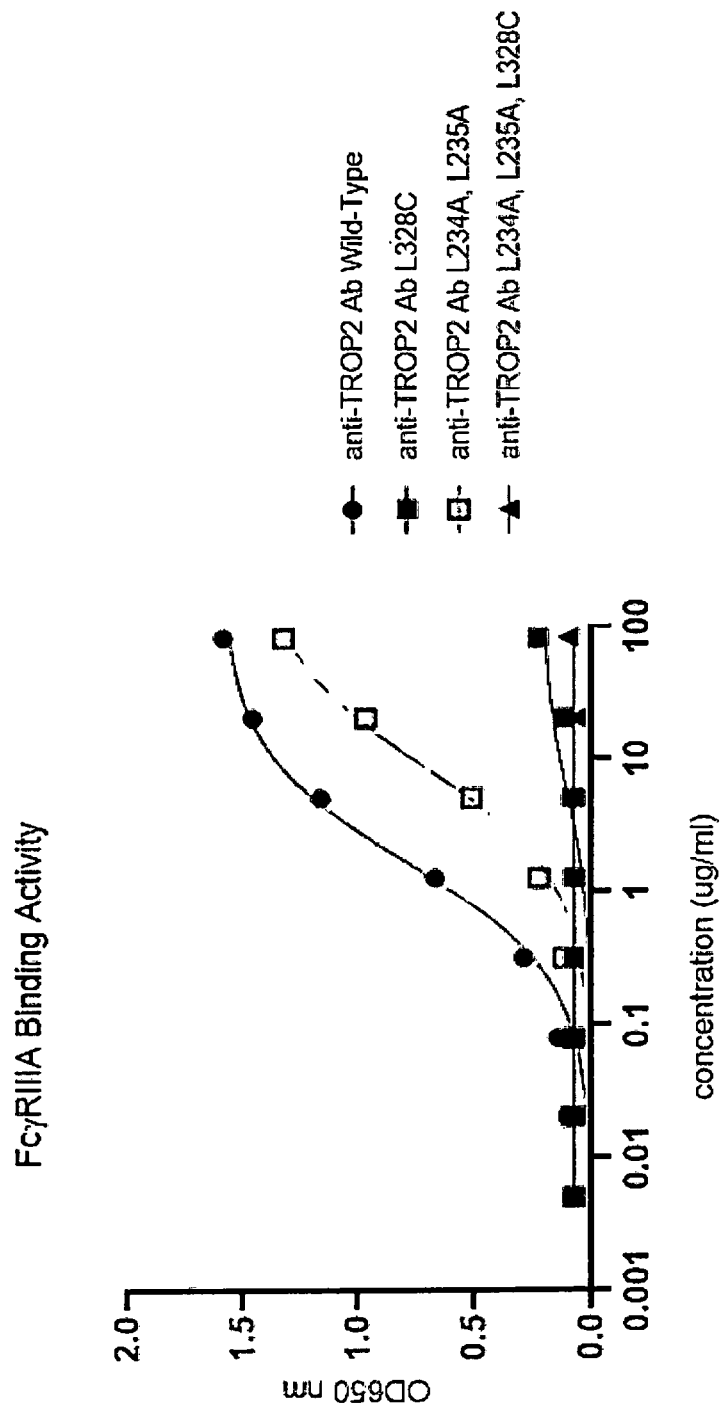
Figure 21. Anti-Trop2 and Fc variants: An inhibition of FcγRIIIA binding is observed for the single & triple mutant

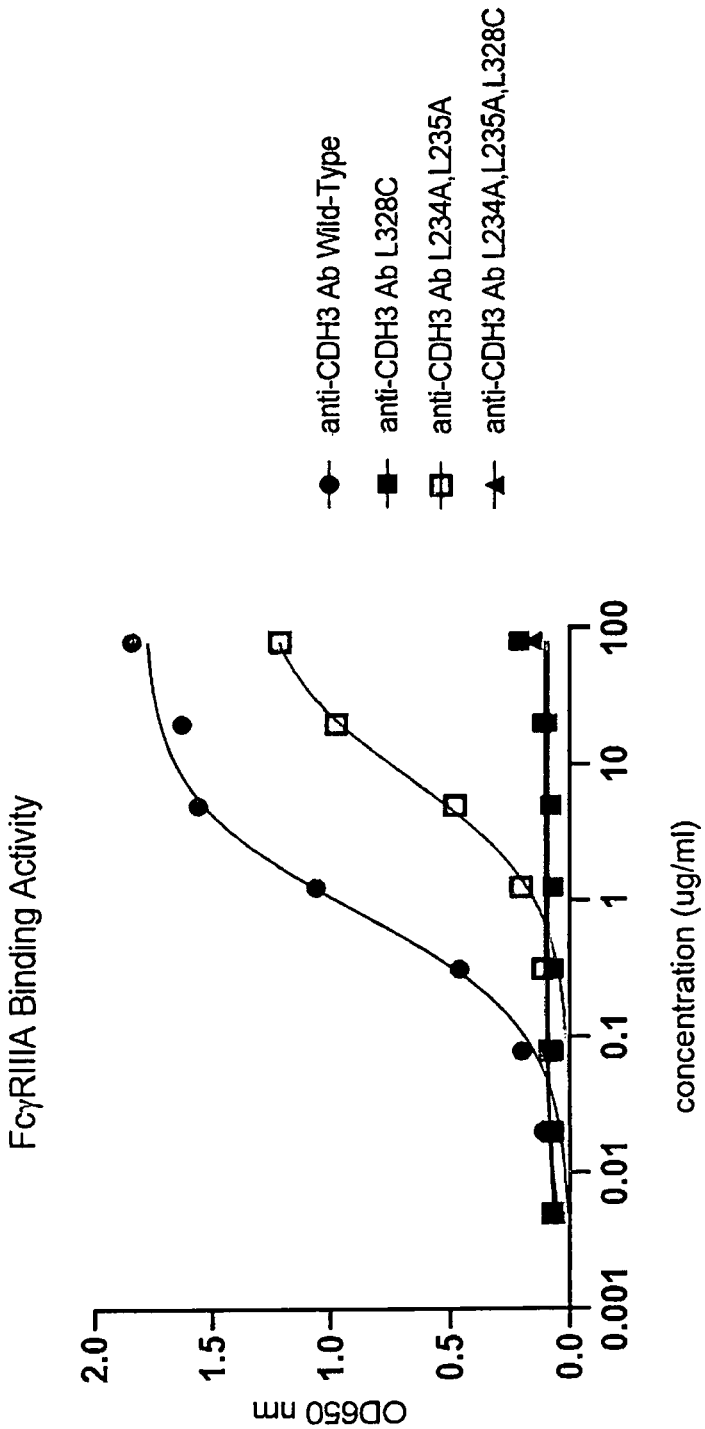
Figure 22. Anti-CDH3 and Fc variants: An inhibition of FcγRIIIA binding is observed for the single & triple mutant

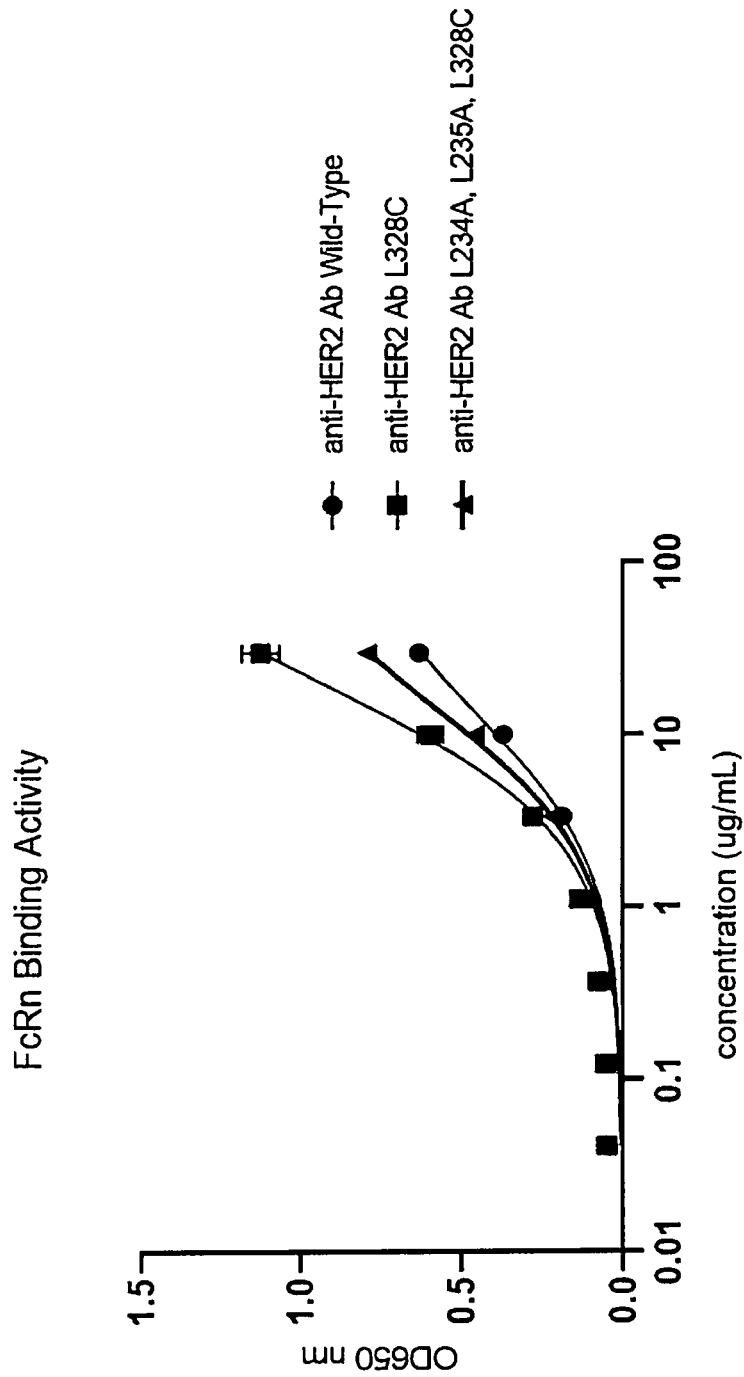
Figure 23. Anti-HER2 mAb and Fc variants: A substantial reduction in FcRn binding is not observed with Fc variants

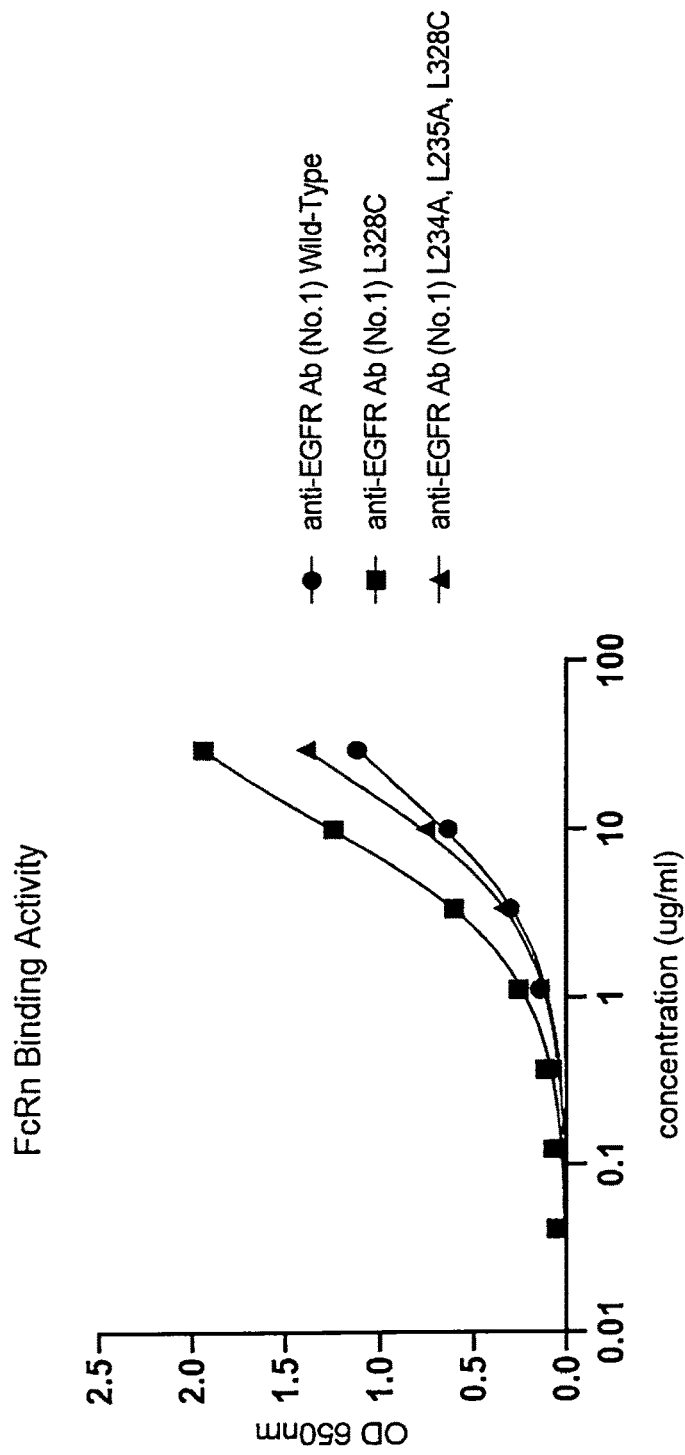
Figure 24. Anti-EGFR mAb No. 1 and Fc variants: A substantial reduction in FcRn binding is not observed with Fc variants

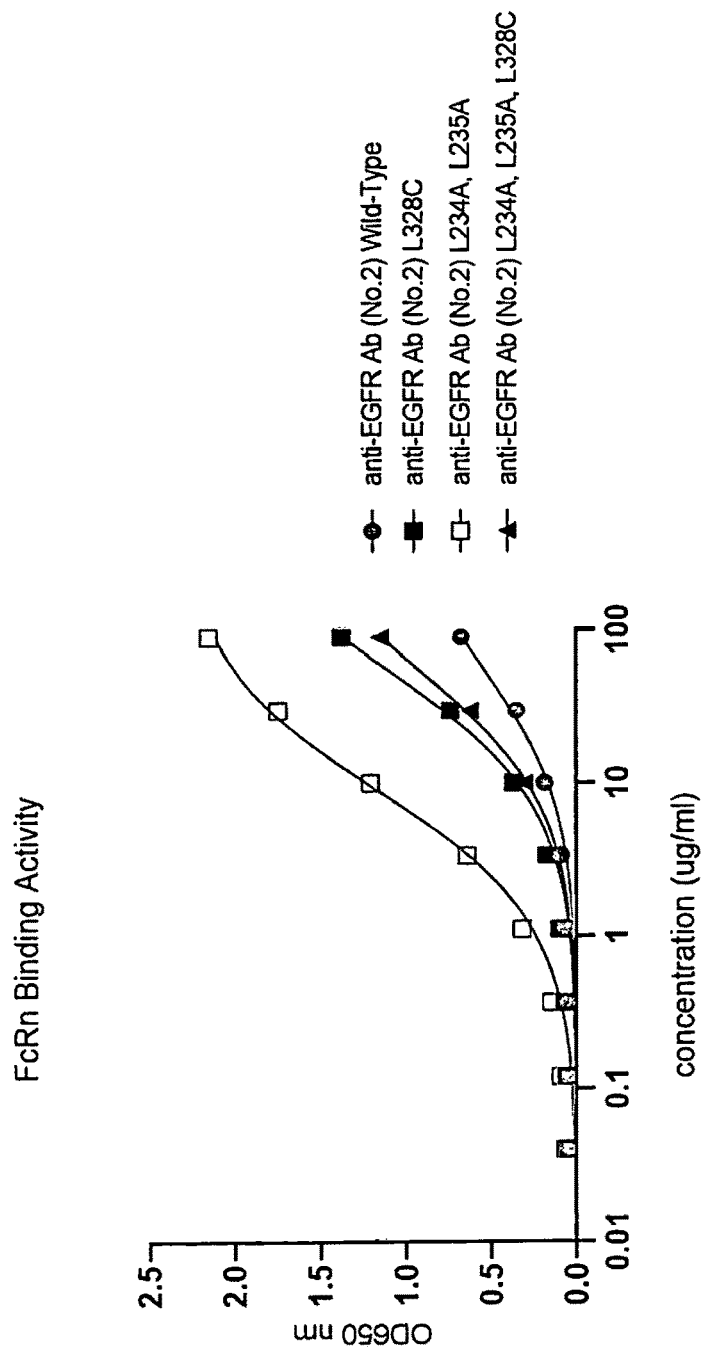
Figure 25. Anti-EGFR mAb No. 2 and Fc variants: A substantial reduction in FcRn binding is not observed with Fc variants

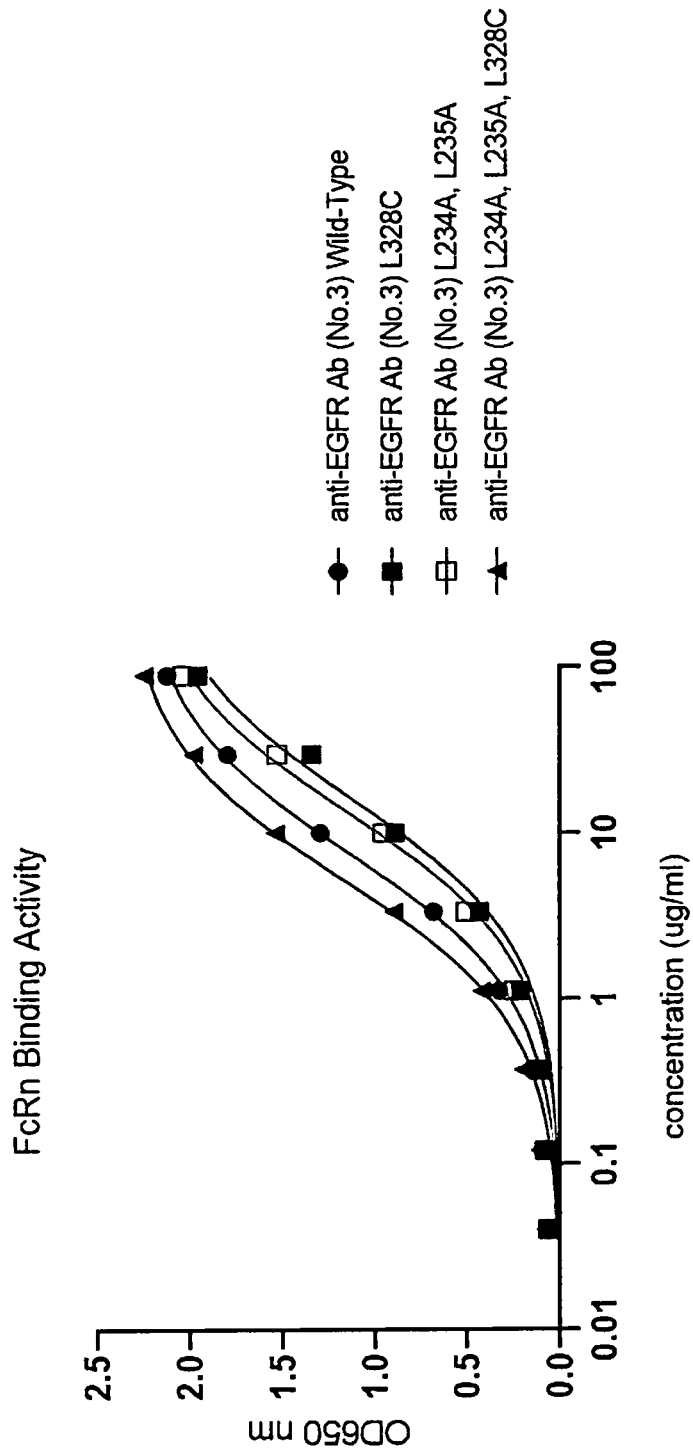
Figure 26. Anti-EGFR mAb No. 3 and Fc variants: A substantial reduction in FcRn binding is not observed with Fc variants

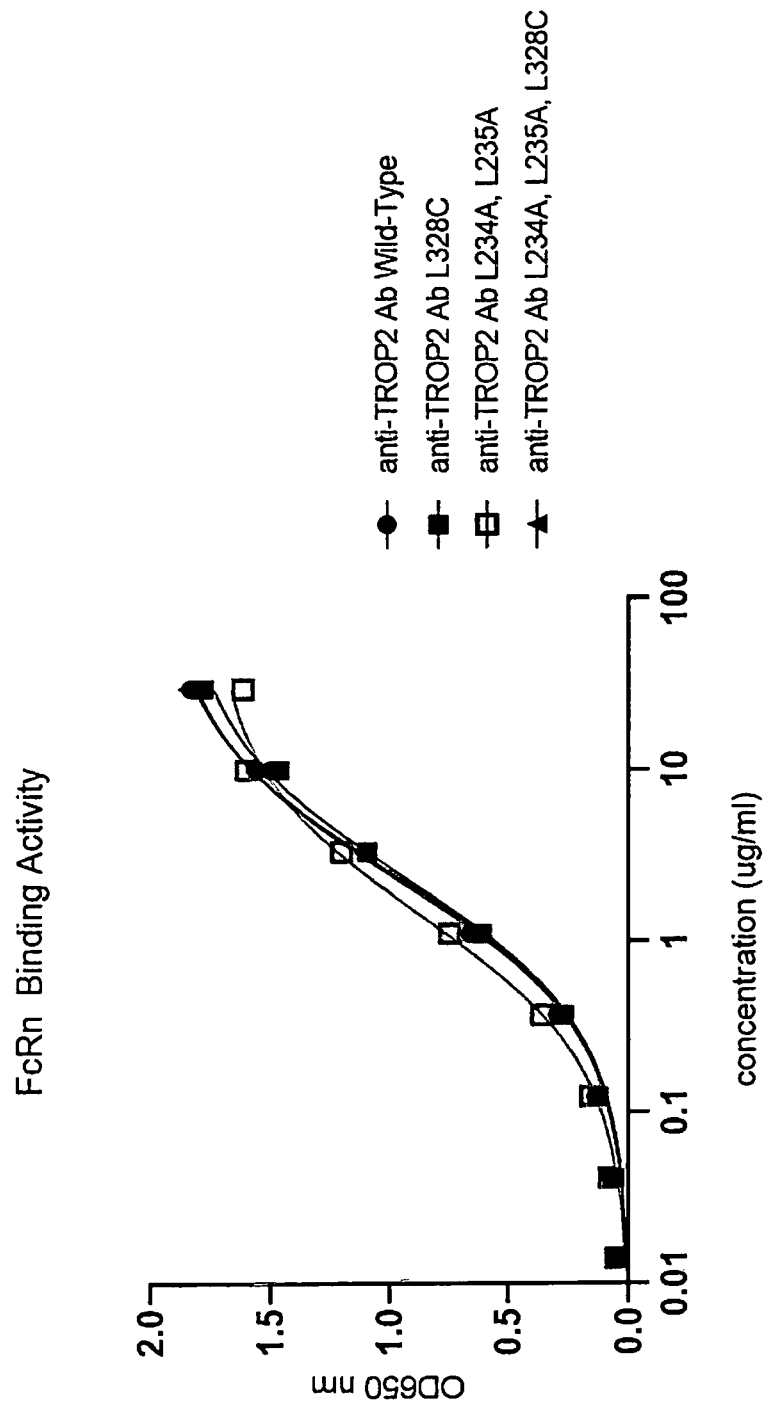
Figure 27. Anti-Trop2 mAb and Fc variants: A substantial reduction in FcRn binding is not observed with Fc variants

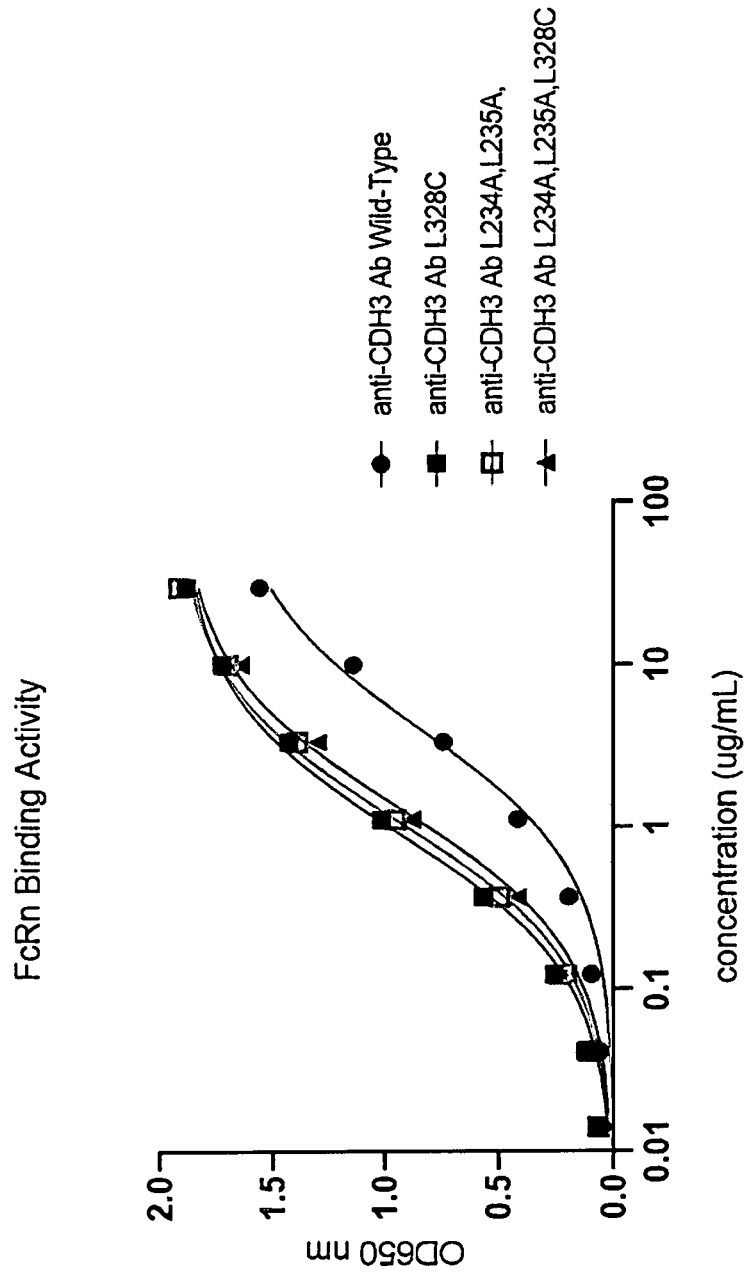
Figure 28. Anti-CDH3 mAb and Fc variants: A substantial reduction in FcRn binding is not observed with Fc variants Figure 29. Binding kinetic analysis of anti-Her2 antibody and Fc variants for FcγRI, IIA, IIB, IIIA, IIIB and FcRn. The Triple Mutant exhibits substantial binding inhibition to all FcγR isoforms but not for FcRn.

| Fcγ Receptor | Fc variant | KD (M) | k$_{on}$ (1/Ms) | k$_{dis}$ (1/s) |
|---|---|---|---|---|
| FcγRI | Wild-type | 1.42E-08 | 1.53E+05 | 2.17E-03 |
| | L328C | 2.21E-08 | 1.51E+05 | 3.33E-03 |
| | L234A, L235A, L328C | 5.80E-07 | 1.11E+05 | 6.46E-02 |
| FcγRIIA | Wild-type | 2.80E-07 | 3.00E+05 | 8.40E-02 |
| | L328C | 9.85E-07 | 8.48E+04 | 8.35E-02 |
| | L234A, L235A, L328C | No/Low binding | | |
| FcγRIIB | Wild-type | 1.80E-07 | 4.17E+05 | 7.53E-02 |
| | L328C | No/Low binding | | |
| | L234A, L235A, L328C | No/Low binding | | |
| FcγRIIIA (F158) | Wild-type | 1.98E-07 | 3.04E+05 | 6.00E-02 |
| | L328C | No/Low binding | | |
| | L234A, L235A, L328C | No/Low binding | | |
| FcγRIIIA (V158) | Wild-type | 1.83E-07 | 2.85E+05 | 5.20E-02 |
| | L328C | 4.71E-07 | 2.55E+05 | 1.20E-01 |
| | L234A, L235A, L328C | No/Low binding | | |
| FcγRIIIB | Wild-type | 2.95E-07 | 2.98E+05 | 8.78E-02 |
| | L328C | No/Low binding | | |
| | L234A, L235A, L328C | No/Low binding | | |
| FcRn (pH6.0) | Wild-type | 6.55E-08 | 4.44E+05 | 2.91E-02 |
| | L328C | 5.87E-08 | 5.34E+05 | 3.13E-02 |
| | L234A, L235A, L328C | 6.79E-08 | 5.00E+05 | 3.39E-02 |

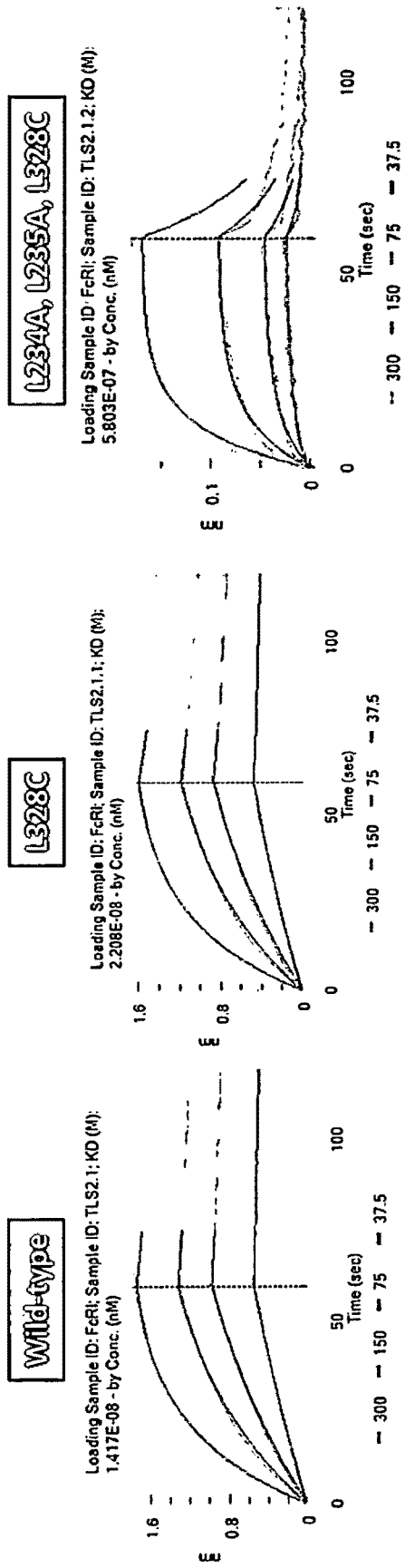
Figure 30. Binding kinetic analysis of anti-Her2 antibody and Fc variants for FcγRI. The dissociation rate is faster for the triple mutation as compared to the wild-type and single mutation.

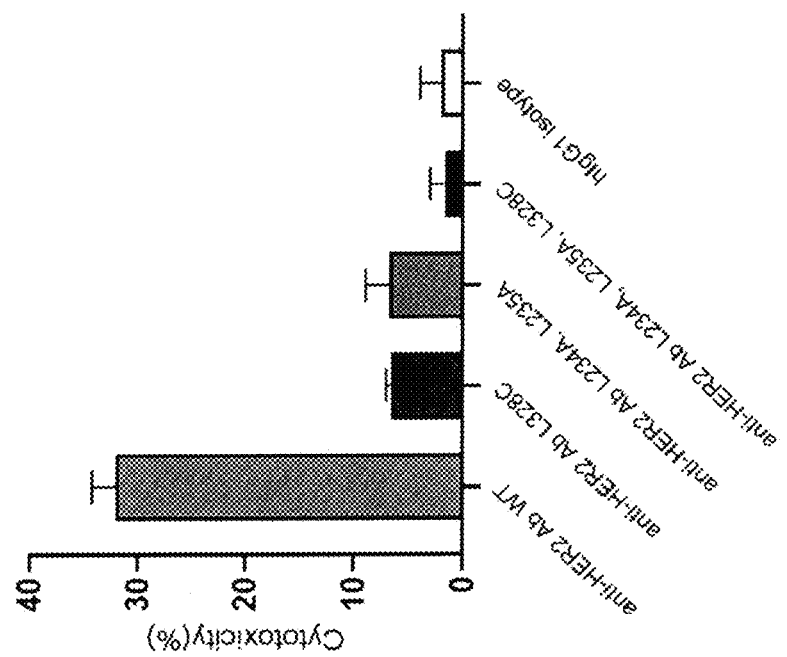
Figure 31. Anti-HER2 mAb and Fc variants: Reduction in ADCC is observed with Fc variants

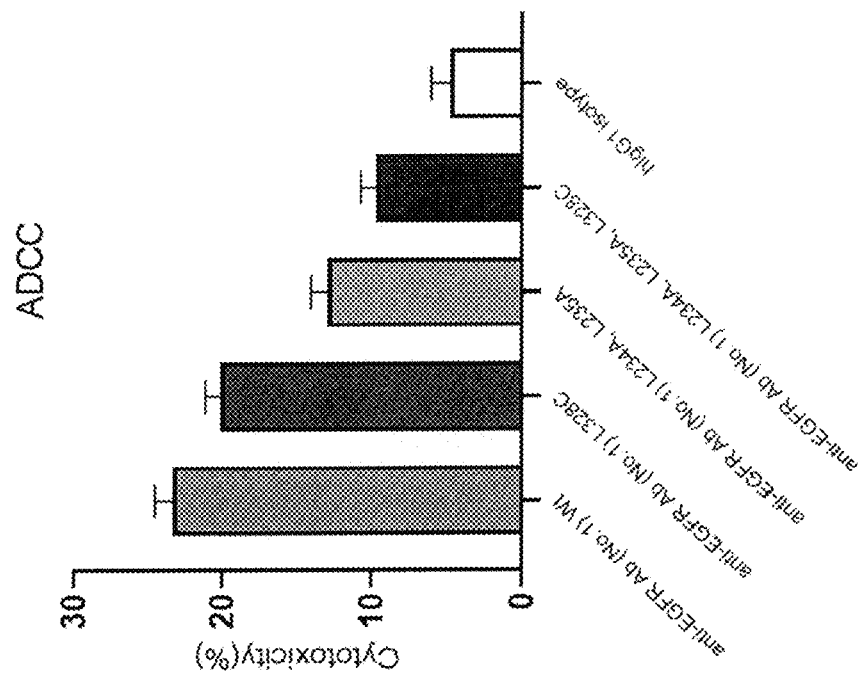
Figure 32. Anti-EGFR mAb No. 1 and Fc variants: Reduction in ADCC is observed with Fc variants

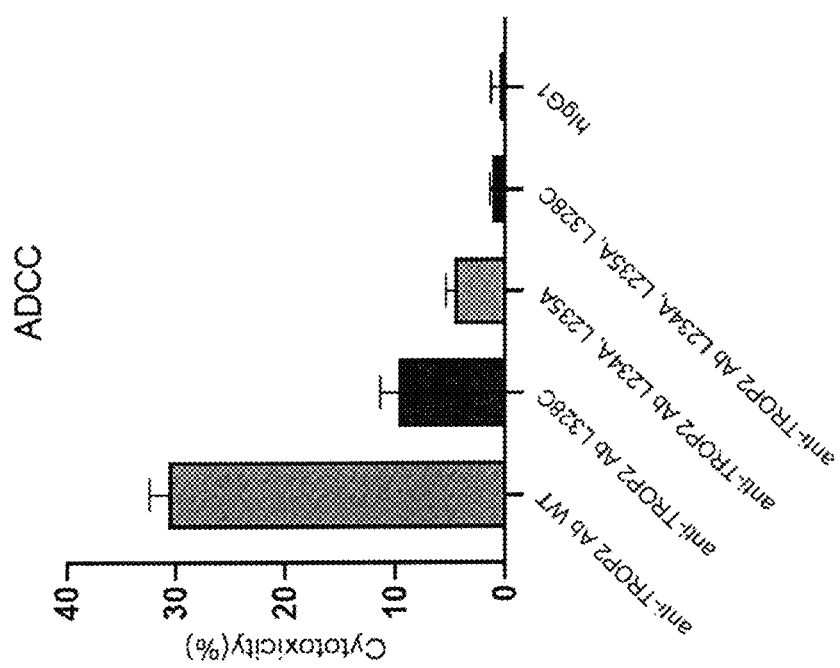
Figure 33. Anti-Trop2 mAb and Fc variants: Reduction in ADCC is observed with Fc variants

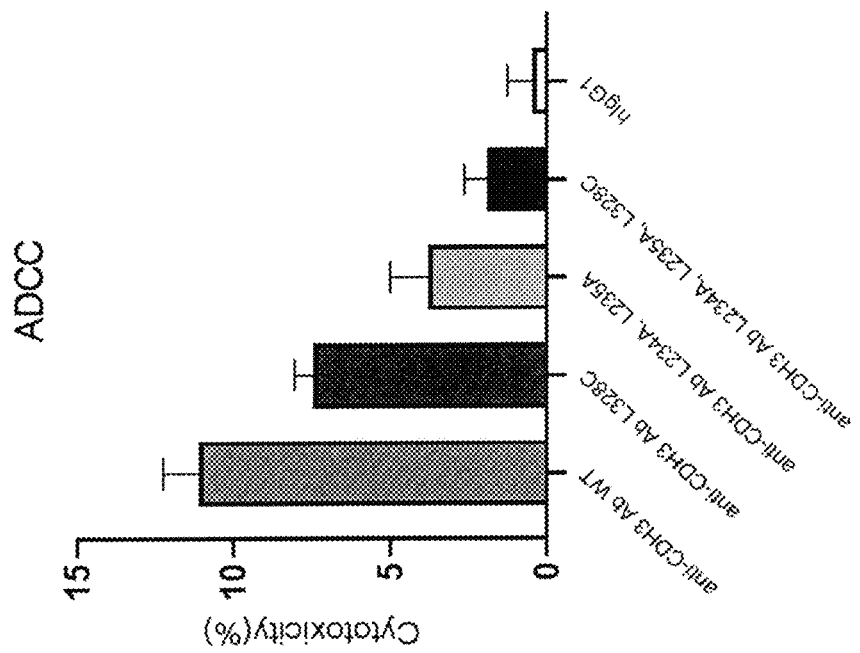
Figure 34. Anti-CDH3 mAb and Fc variants: Reduction in ADCC is observed with Fc variants

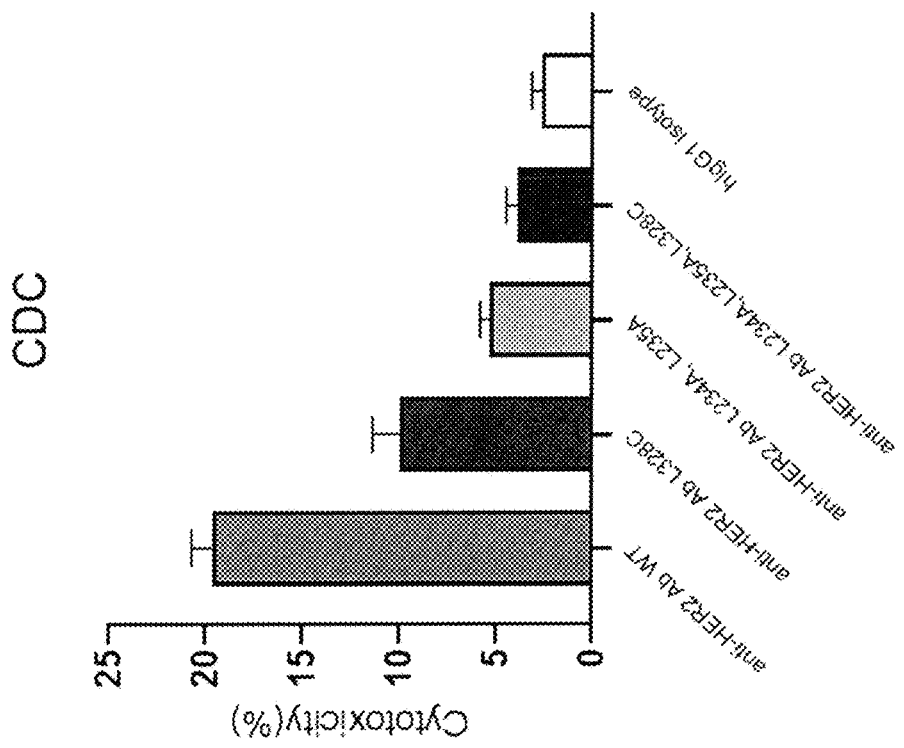
Figure 35. Anti-HER2 mAb and Fc variants: Reduction in CDC is observed with Fc variants

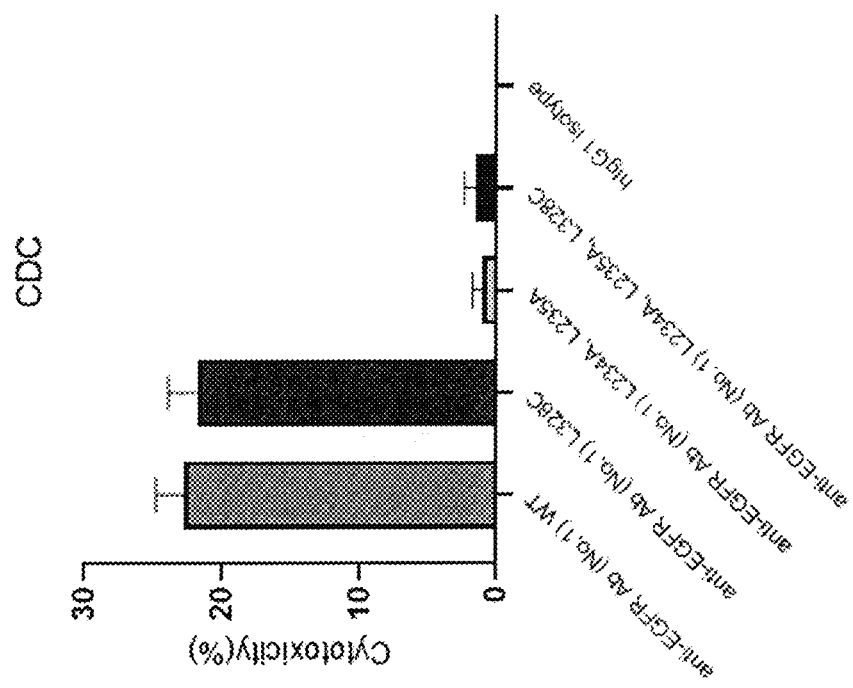
Figure 36. Anti-EGFR mAb No. 1 and Fc variants: Reduction in CDC is observed with Fc variants

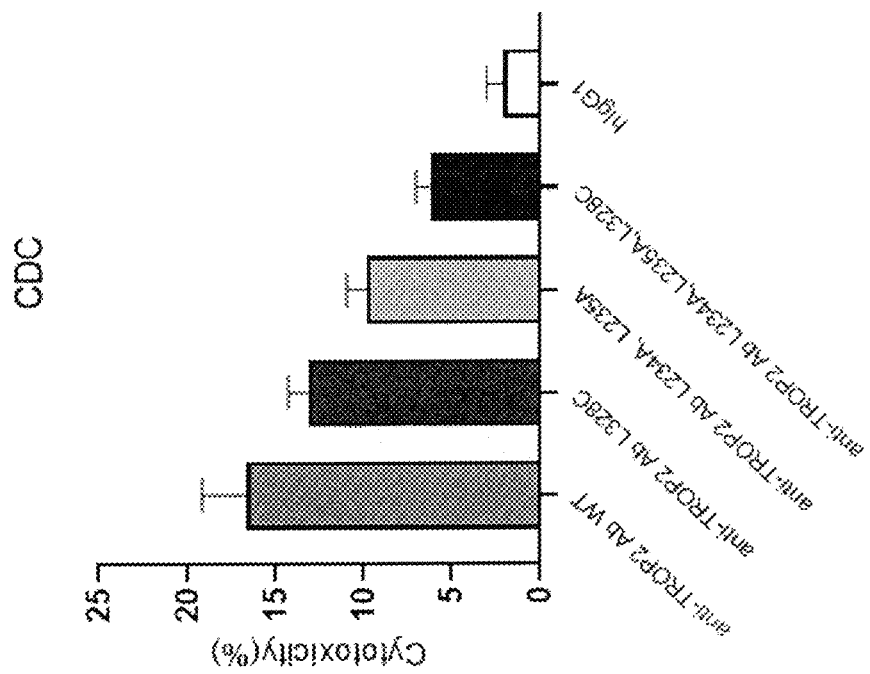
Figure 37. Anti-Trop2 mAb and Fc variants: Reduction in CDC is observed with Fc variants

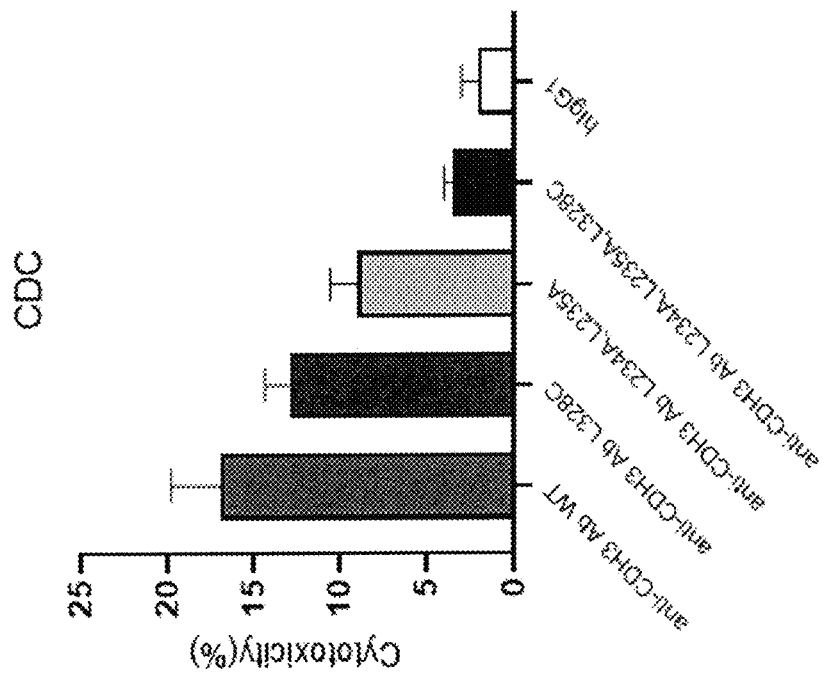
Figure 38. Anti-CDH3 mAb and Fc variants: Reduction in CDC is observed with Fc variants

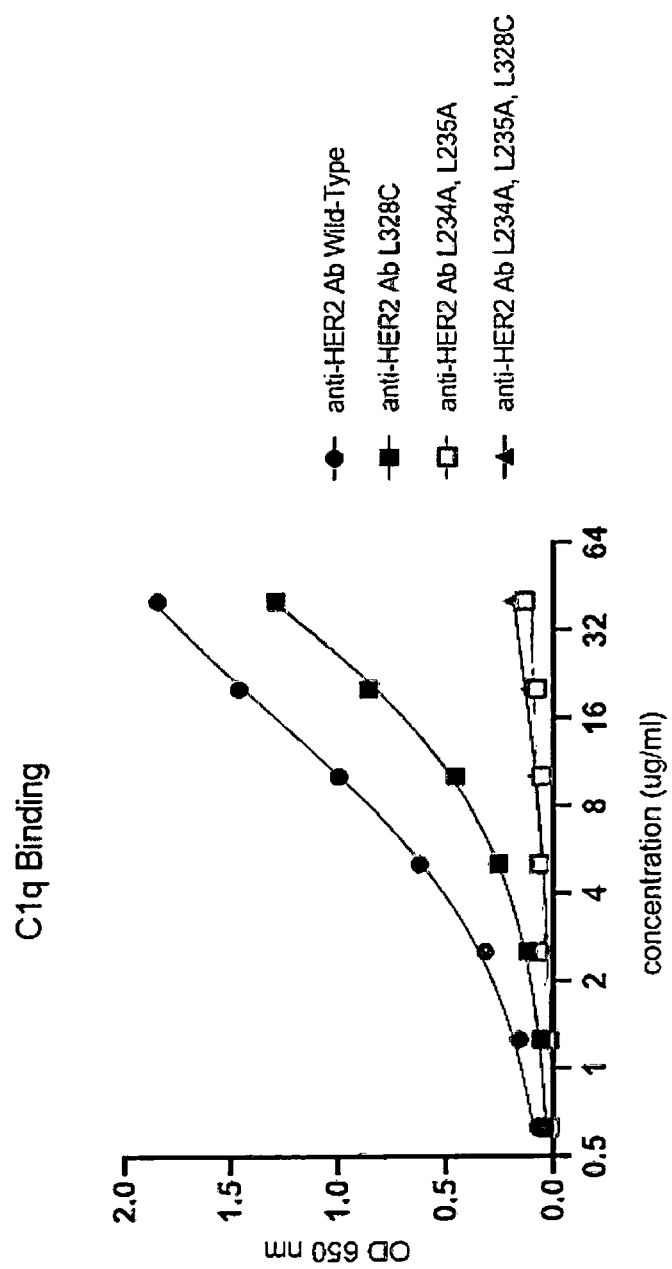
Figure 39. Anti-Her2 mAb and Fc variants: Reduction in C1q binding is observed with Fc variants

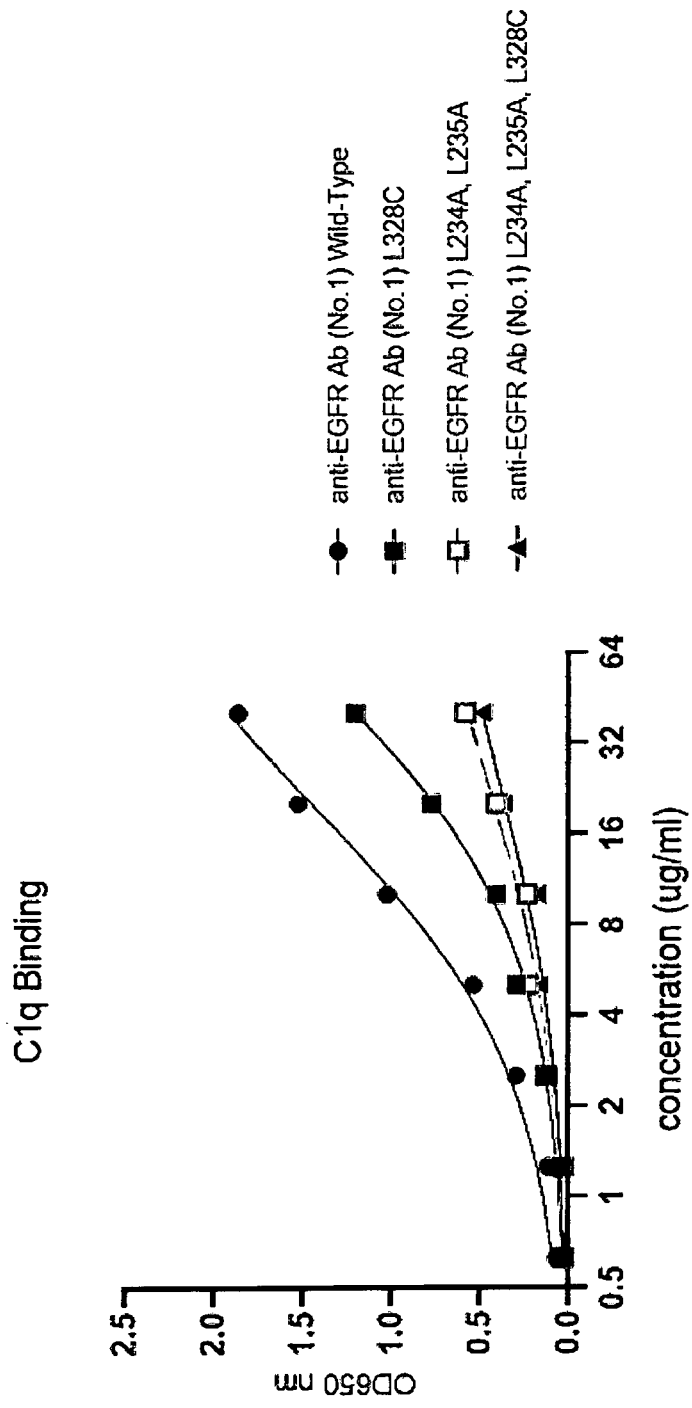
Figure 40. Anti-EGFR mAb (No. 1) and Fc variants: Reduction in C1q binding is observed with Fc variants

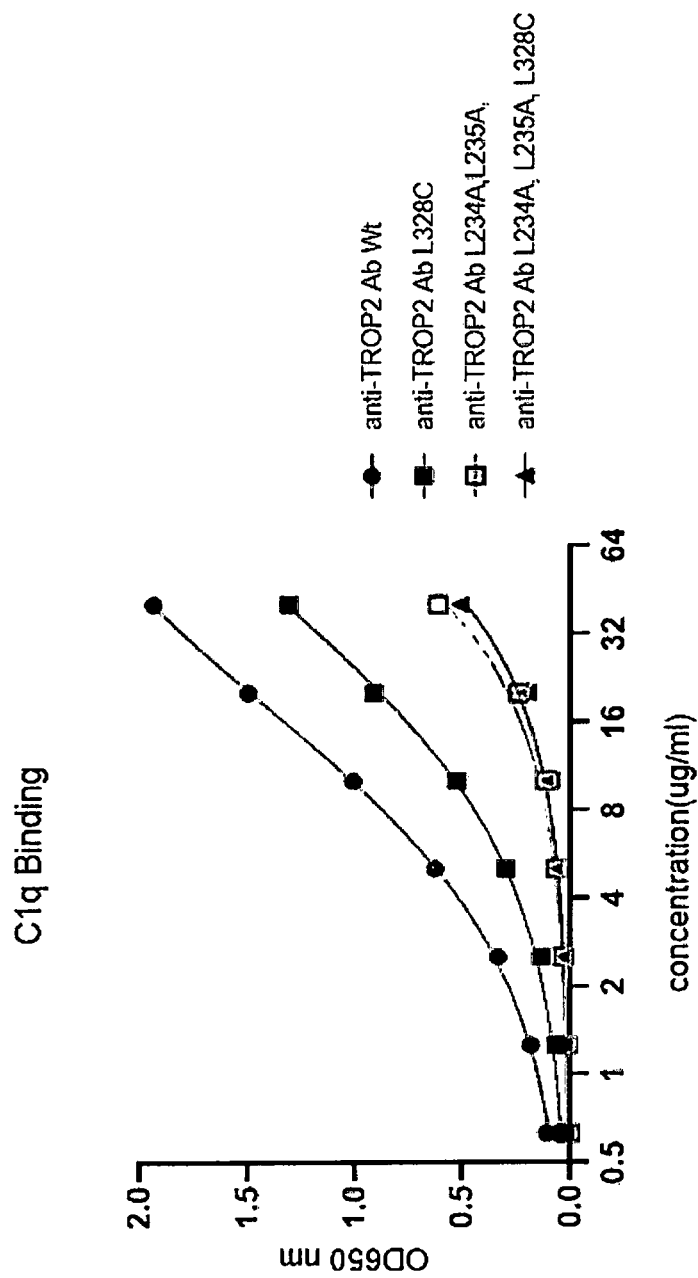
Figure 41. Anti-Trop2 mAb and Fc variants: Reduction in C1q binding is observed with Fc variants

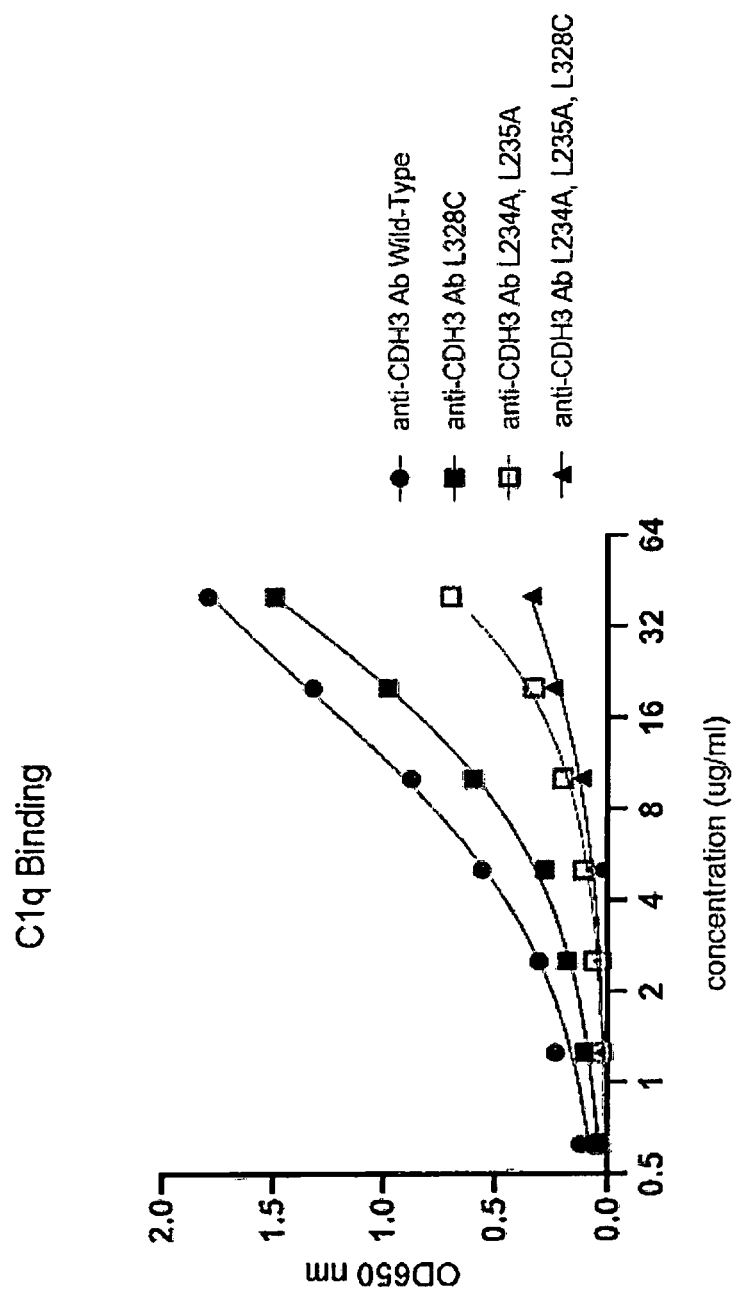
Figure 42. Anti-CDH3 mAb and Fc variants: Reduction in C1q binding is observed with Fc variants

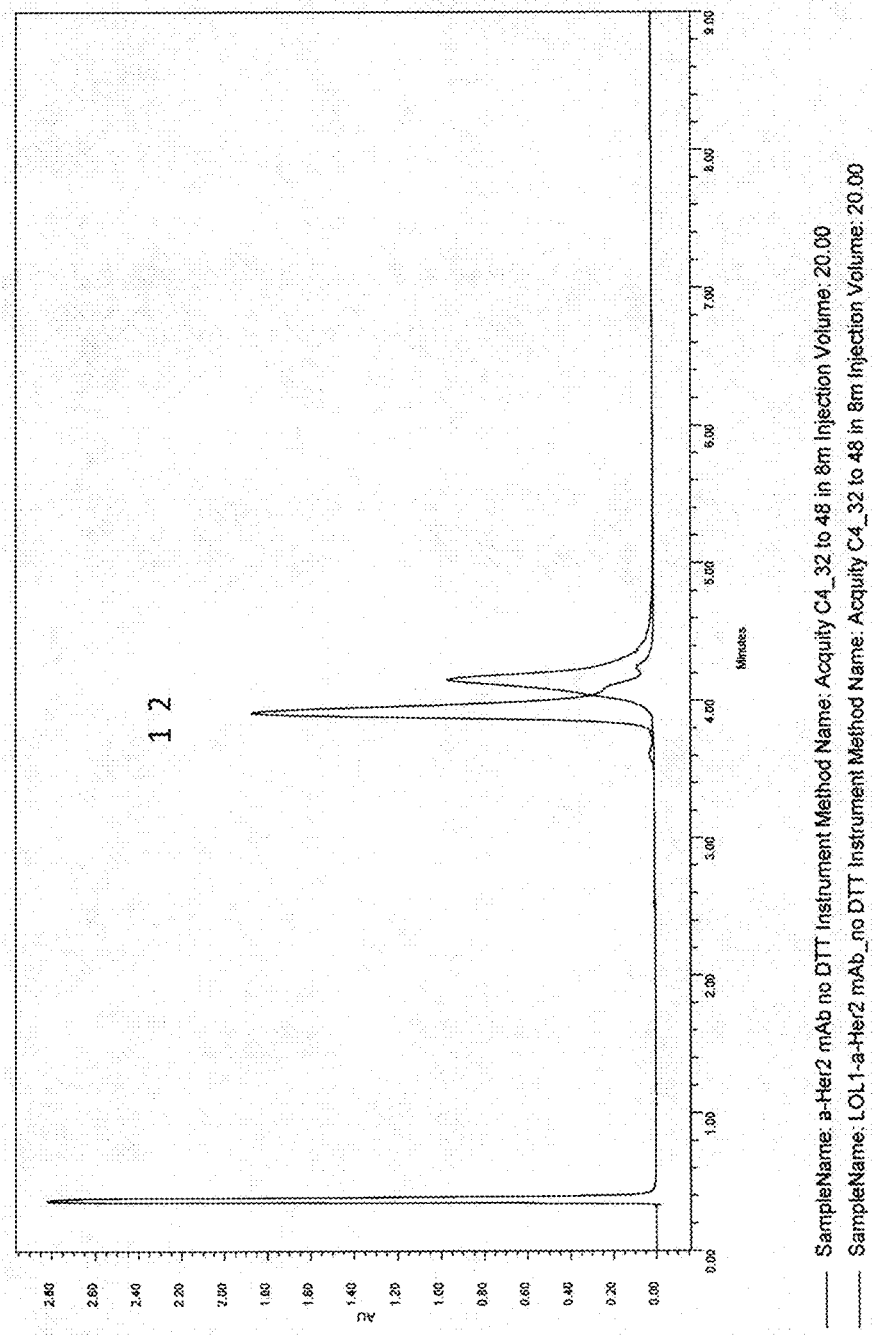
Figure 43. Reverse-Phase Column Chromatography Profile of anti-Her2 mAb triple mutant conjugated with a proprietary payload.

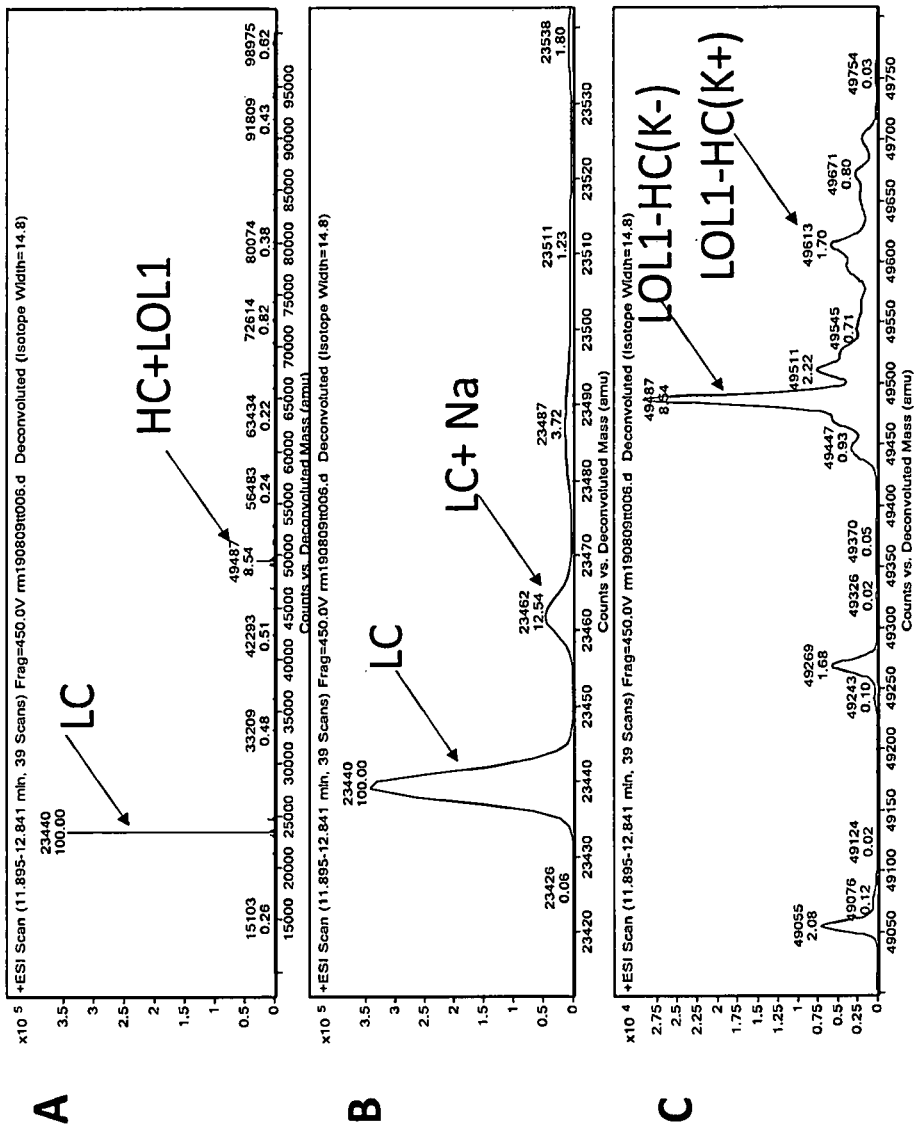
Figure 44. Intact mass analysis of LOL-1 conjugated triple mutant anti-HER2 mAb.

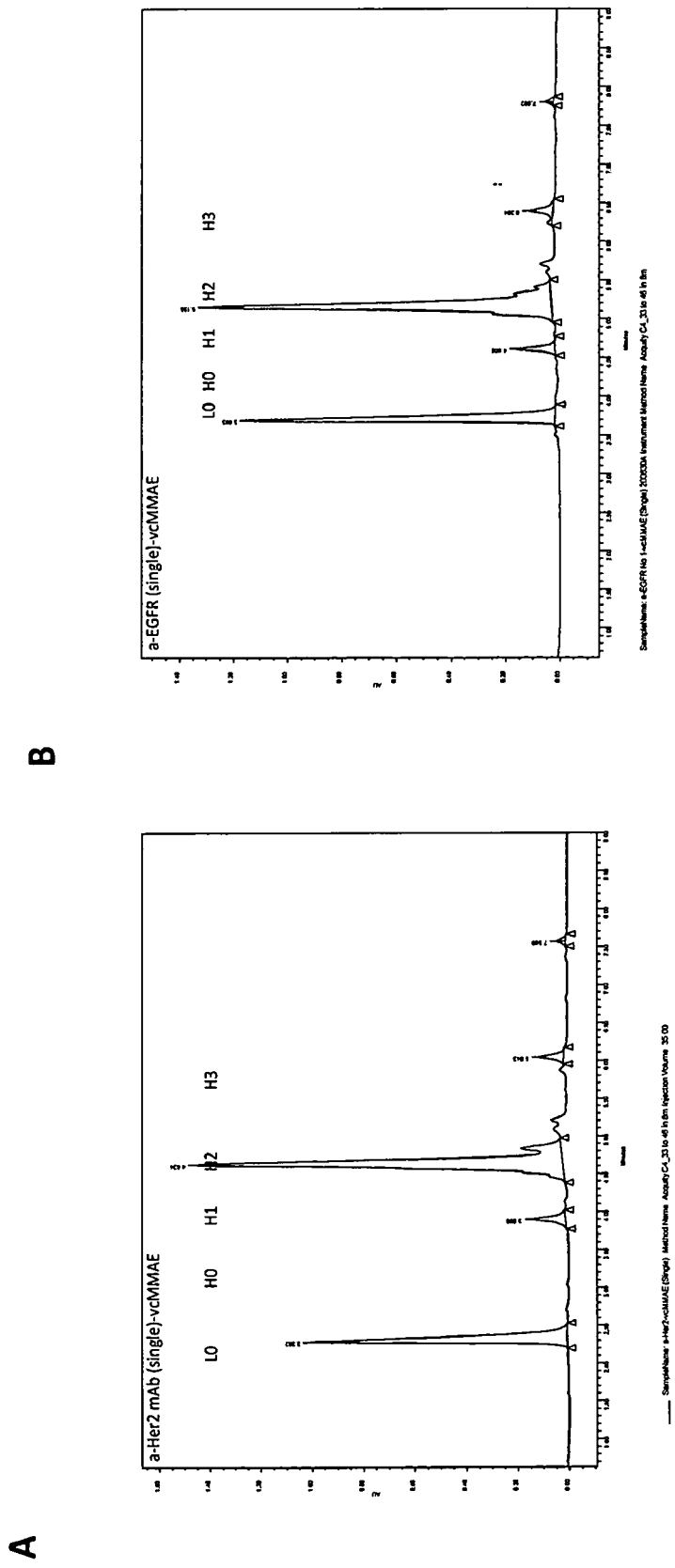
Figure 45. Reverse-Phase Column Chromatography Profiles for L328C variants of anti-HER2 and anti-EGFR mAbs.

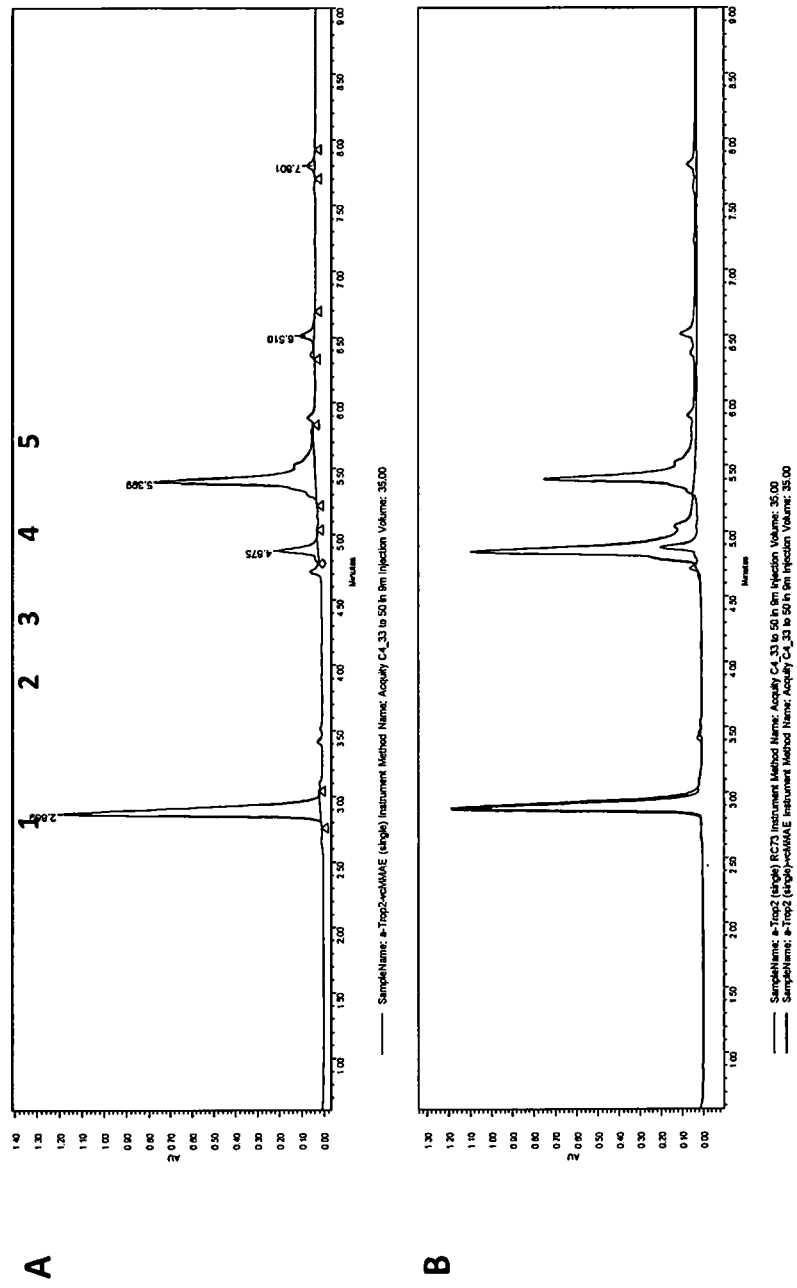
Figure 46. Reverse-Phase Column Chromatography Profile for L328C variant of anti-TROP2 mAb conjugated with vcMMAE.

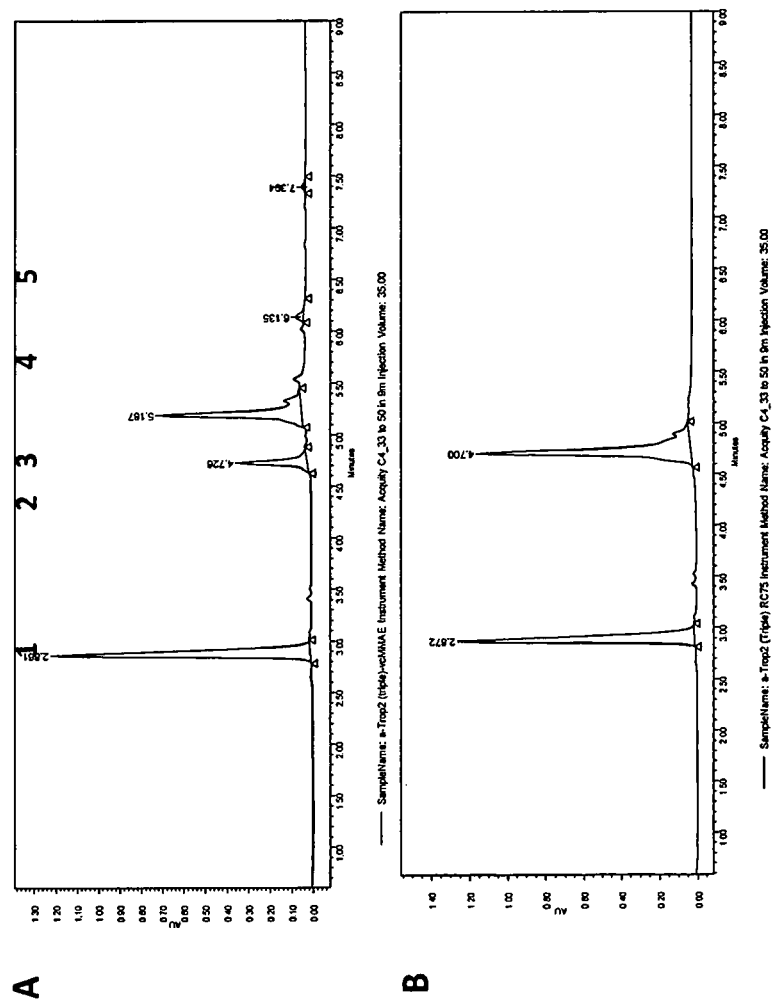
Figure 47. Reverse-Phase column chromatography of triple mutant anti-TROP2 antibody conjugated with vcMMAE.

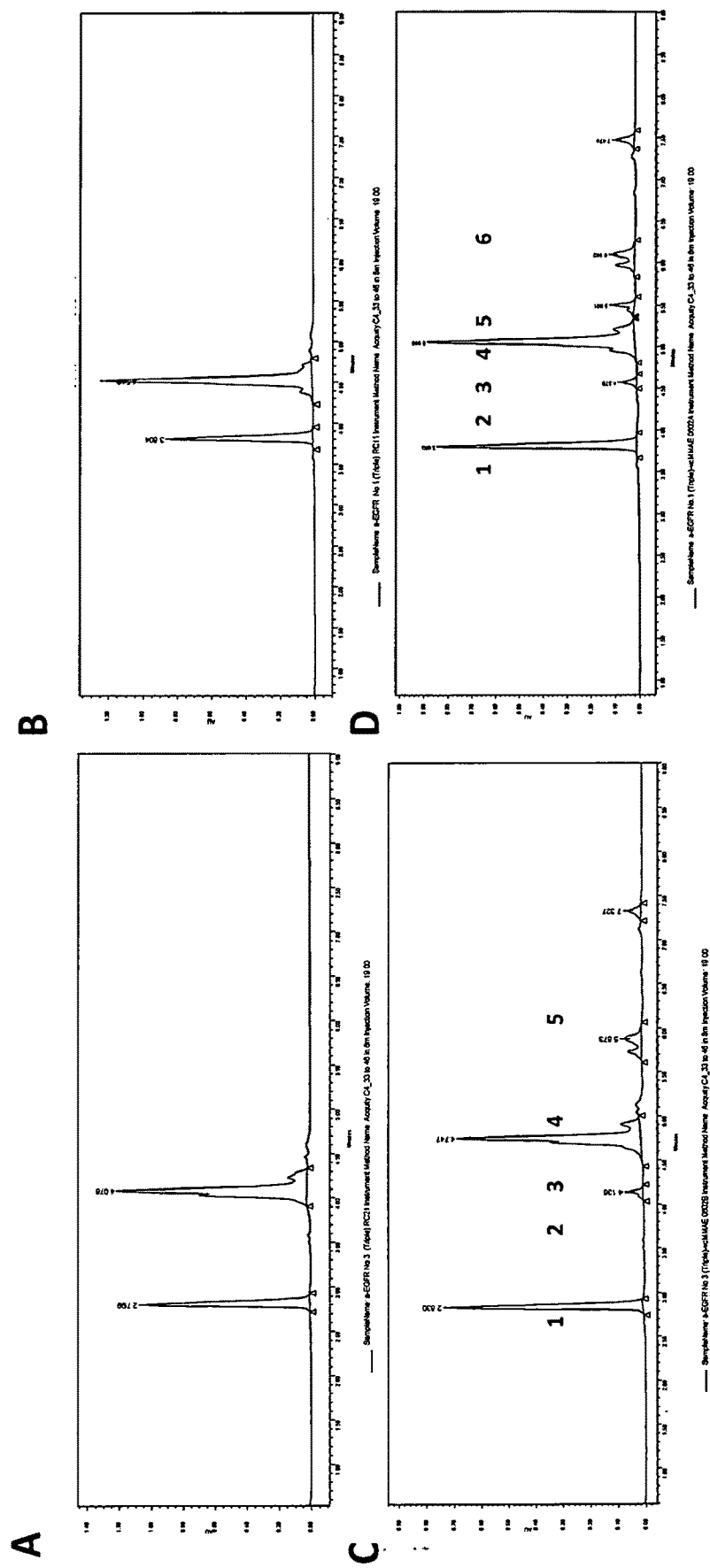
Figure 48. Reverse-Phase Column Chromatography Profiles for L234A, L235A, L328C variants of anti-EGFR mAbs conjugated with vcMMAE.

Figure 49. Peak assignment and DAR calculation based on Reverse-Phase column chromatography data (provided in Figure 48).

| ADC | Peak # | Name | Retention Time | % Area |
|---|---|---|---|---|
| a-EGFR No.3 (Triple) conjugated with vcMMAE | 1 | LC | 2.83 | 100 |
| | 2 | HC | 4.136 | 3.7 |
| | 3 (Site-Specific) | HC+1MMAE | 4.747 | 79.5 |
| | 4 | HC+2MMAE | 5.873 | 12.3 |
| | 5 | HC+3MMAE | 7.327 | 4.3 |
| a-EGFR No.1 (Triple) conjugated with vcMMAE | 5 | LC | 3.803 | 91 |
| | 1 | HC | 4.57 | 2.8 |
| | 2 (Site-Specific) | HC+1 MMAE | 5.058 | 78.7 |
| | 6 | LC+1 MMAE | 5.501 | 4.5 |
| | 3 | HC+2 MMAE | 6.102 | 12.1 |
| | 4 | HC+3 MMAE | 7.474 | 4.5 |

Figure 50. Analytical attributes of the resulting ADCs.

| Conjugates (single mutants) | TARGET | DAR | % Monomer by SEC | % DAR2 |
|---|---|---|---|---|
| anti-EGFR Ab No 1 (L328C)-vcMMAE | EGFR | 2.0 | 98.2% | 90.0% |
| anti-HER2 Ab (L328C)-vcMMAE | HER2 | 2.0 | 98.2% | 89.0% |
| anti-TROP2 Ab (L328C)-vcMMAE | TROP2 | 2.0 | 99.6% | 78.7% |

| Conjugates (triple mutants) | TARGET | DAR | % Monomer by SEC | % DAR2 |
|---|---|---|---|---|
| anti-EGFR Ab No 1 (L234A, L235A, L328C)-vcMMAE | EGFR | 2.0 | 99.2% | 80.0% |
| anti-EGFR Ab No.3 (L234A, L235A, L328C)-vcMMAE | EGFR | 2.3 | 98.0% | 82.0% |
| LOL1-anti-Her2 Ab (L234A, L235A, L328C) | HER2 | 2.0 | 96.2% | 86.0% |
| anti-TROP2 Ab (L234A, L235A, L328C)-vcMMAE | TROP2 | 1.6 | 99.6% | 70.2% |

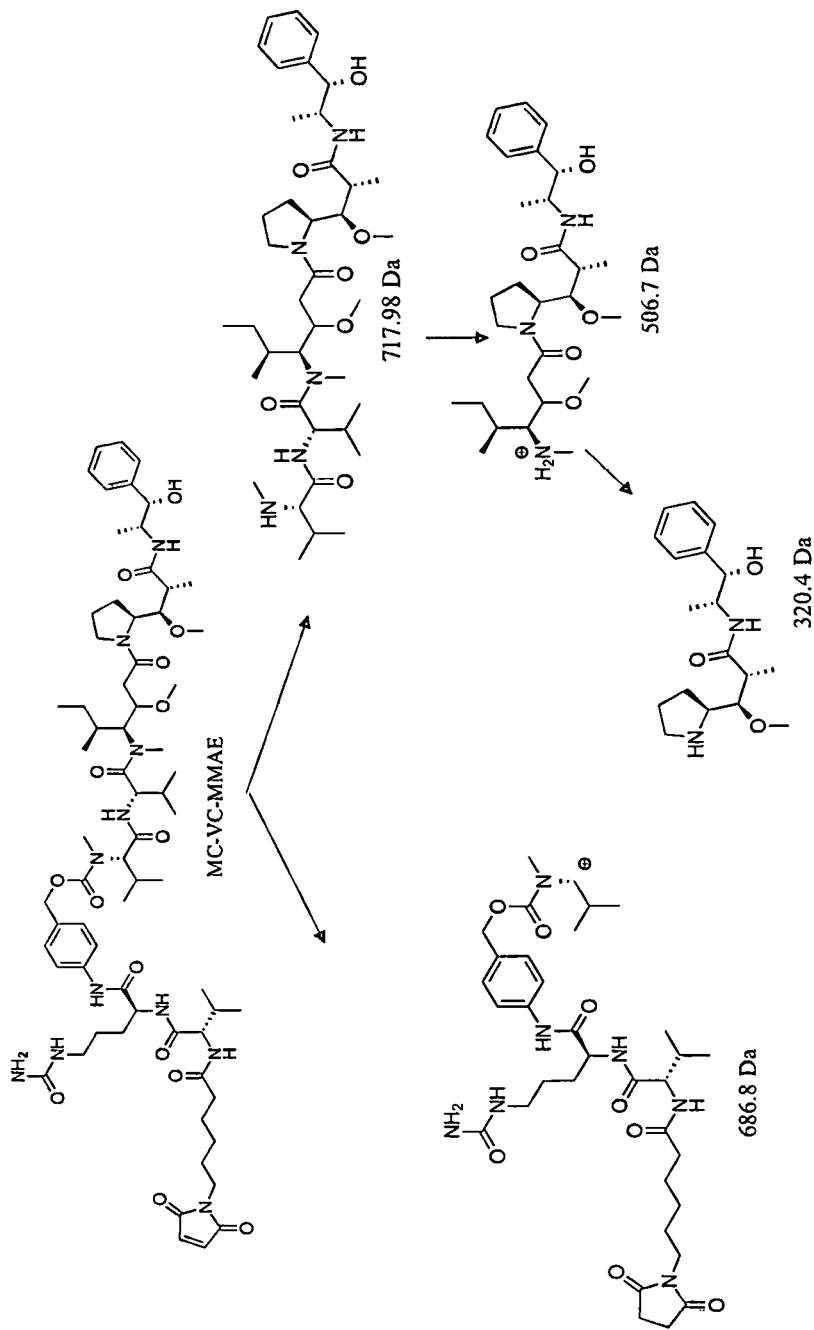
Figure 51: Characteristic daughter ions following fragmentation of a vcMMAE-peptide Figure 52: Sequence coverage of anti-EGFR No.1 triple mutant antibody conjugated with vcMMAE. (A). Light Chain, (B). Heavy Chain.
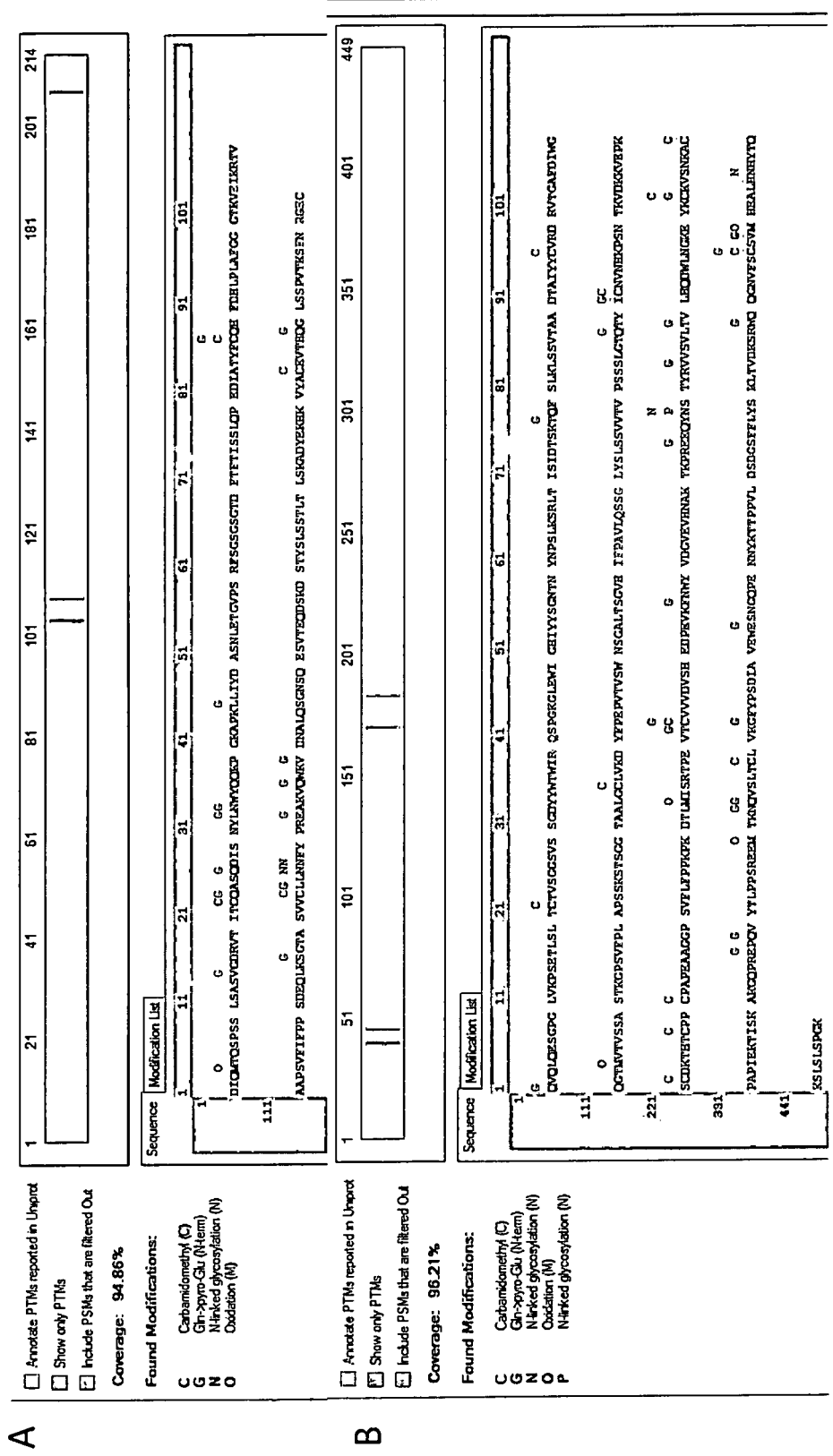

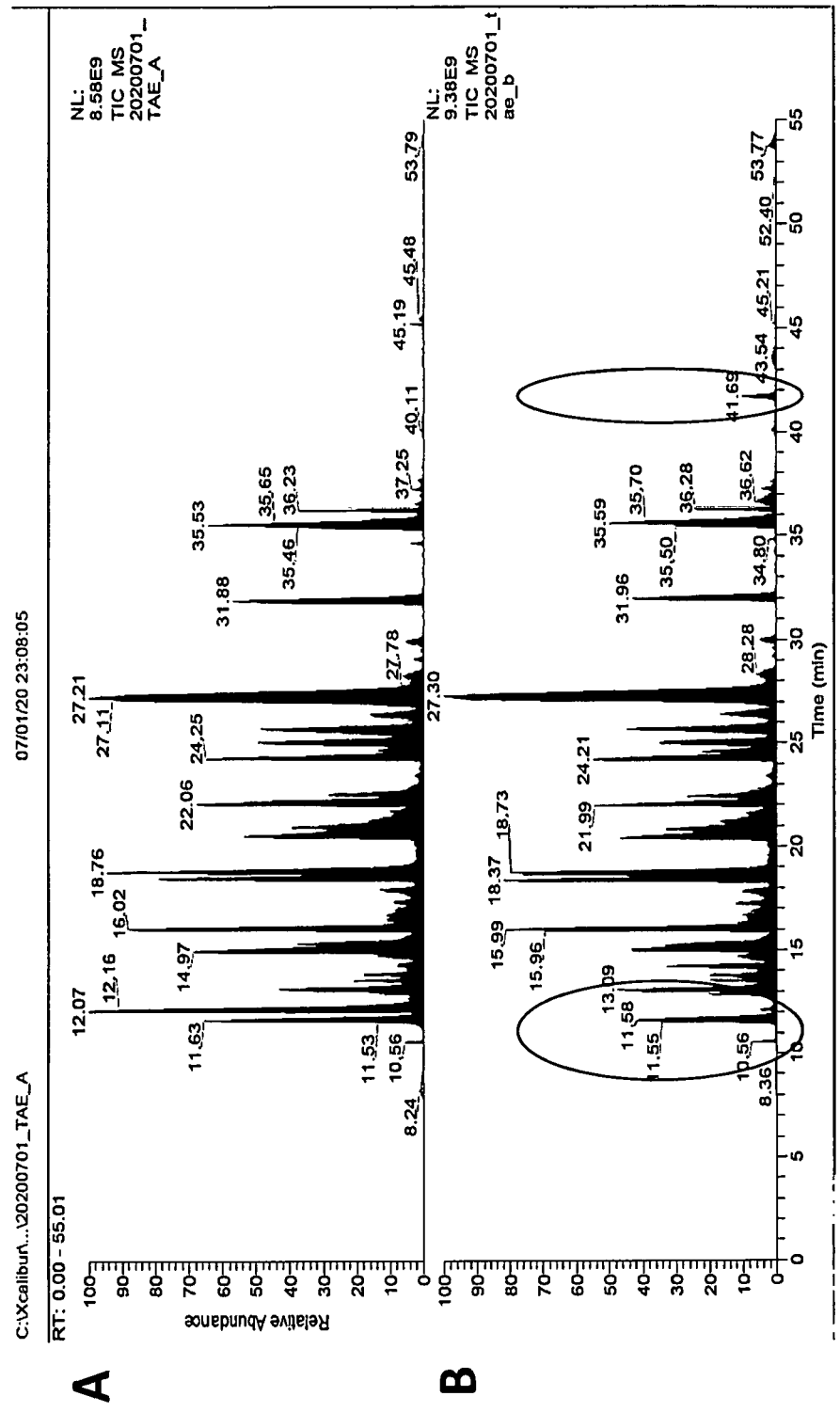
Figure 53. TIC Chromatograms of peptides following digestion with trypsin.

Figure 54. Conjugation site for anti-EGFR antibody No. 1 with triple mutation.
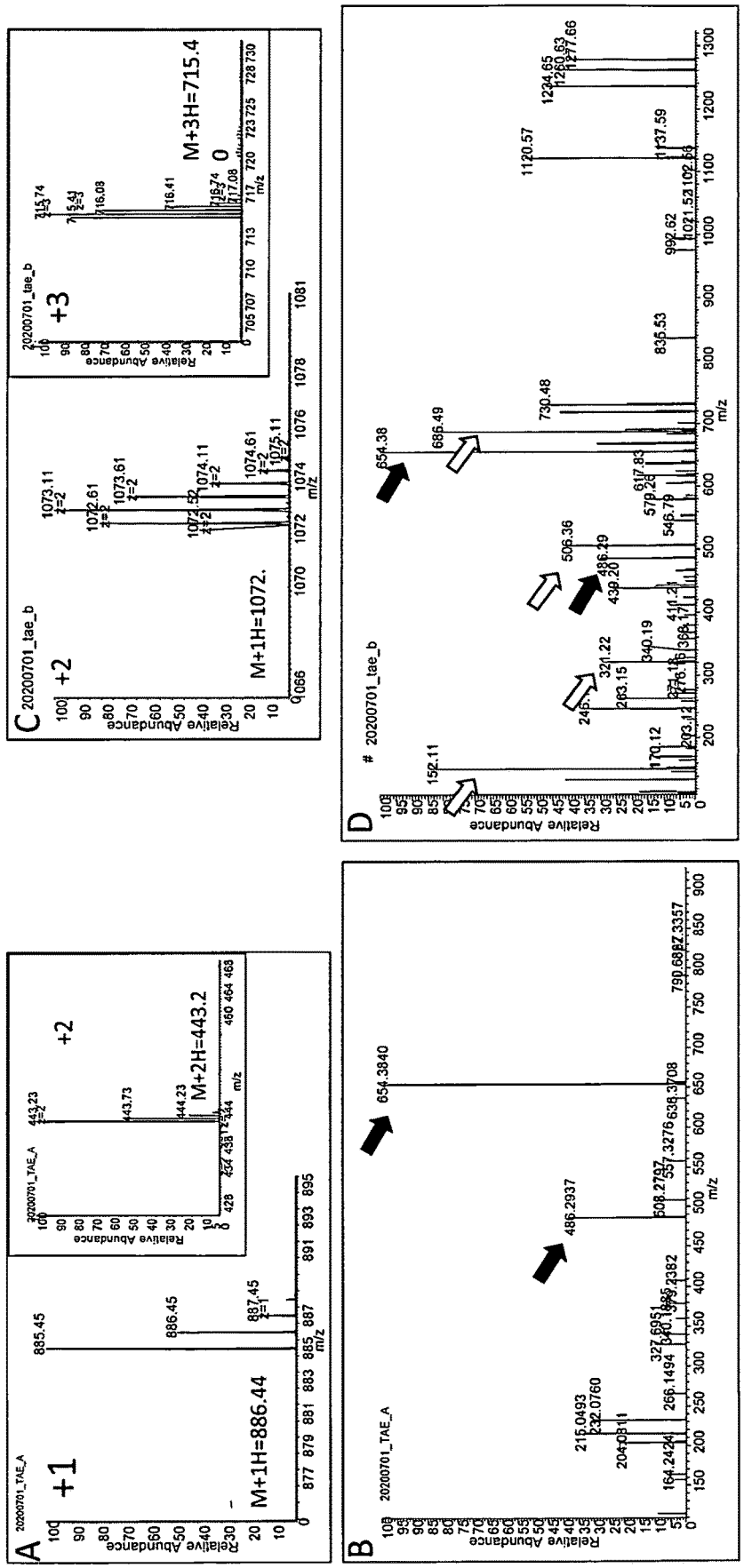

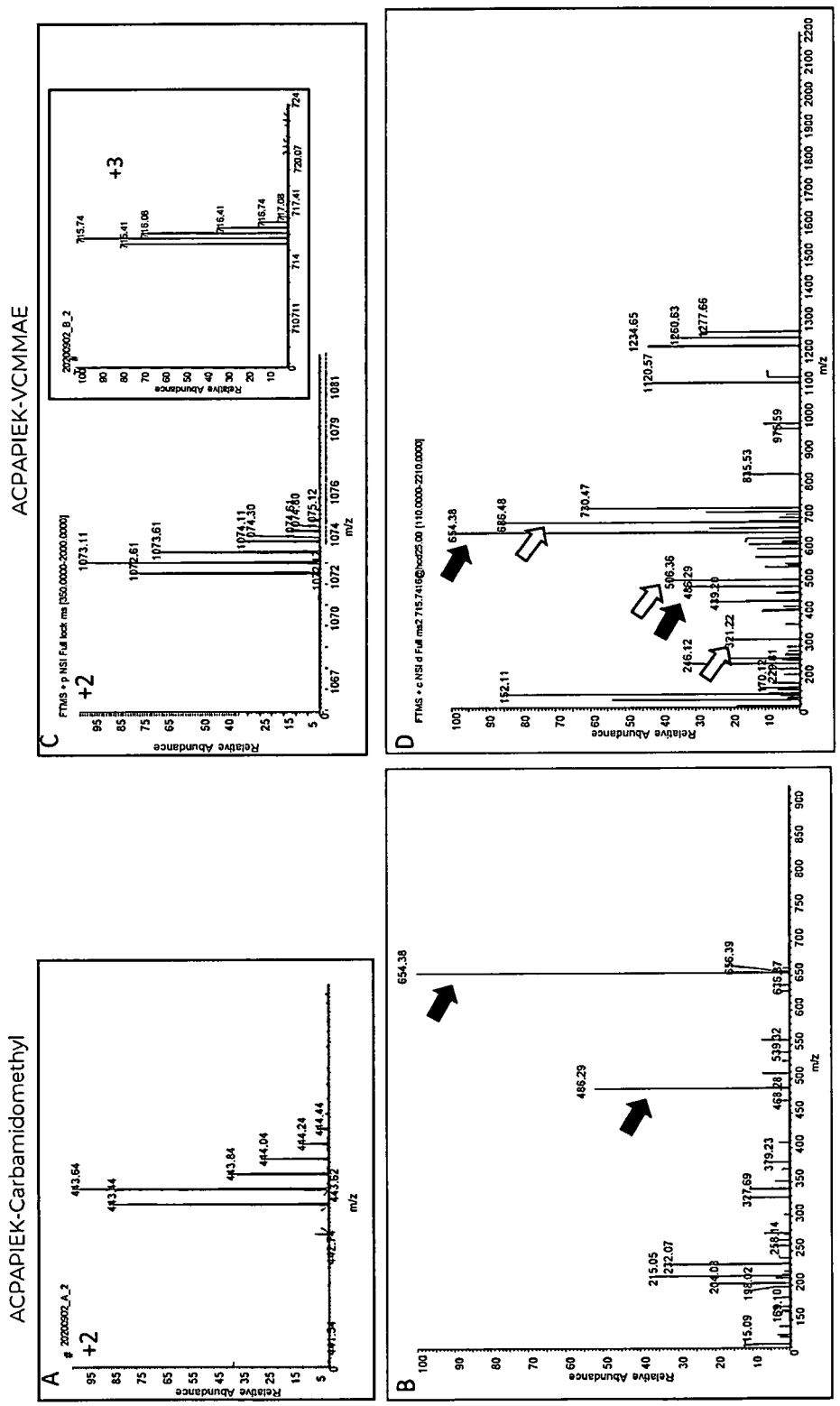
Figure 55: Confirmation of site of conjugation in anti-EGFR antibody No. 1 with single mutation ADC.

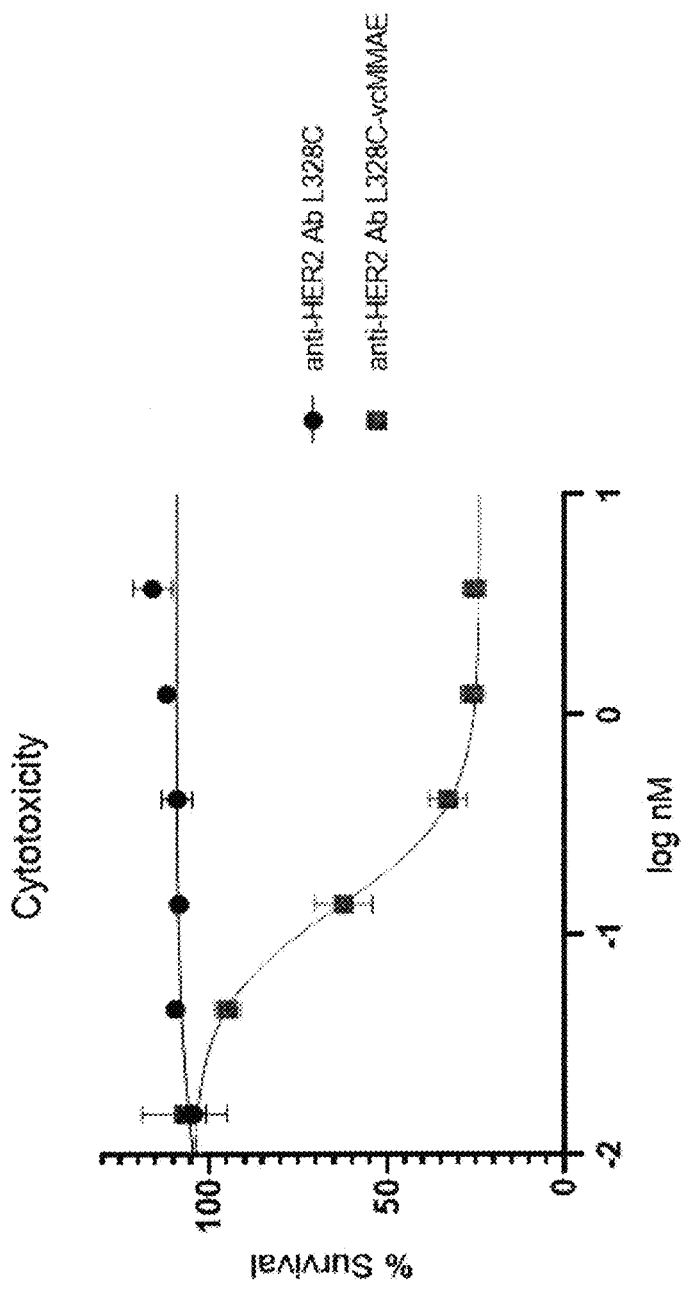
Figure 56. Cytotoxicity mediated by L328C variant of anti-HER2 antibody conjugated with vcMMAE.

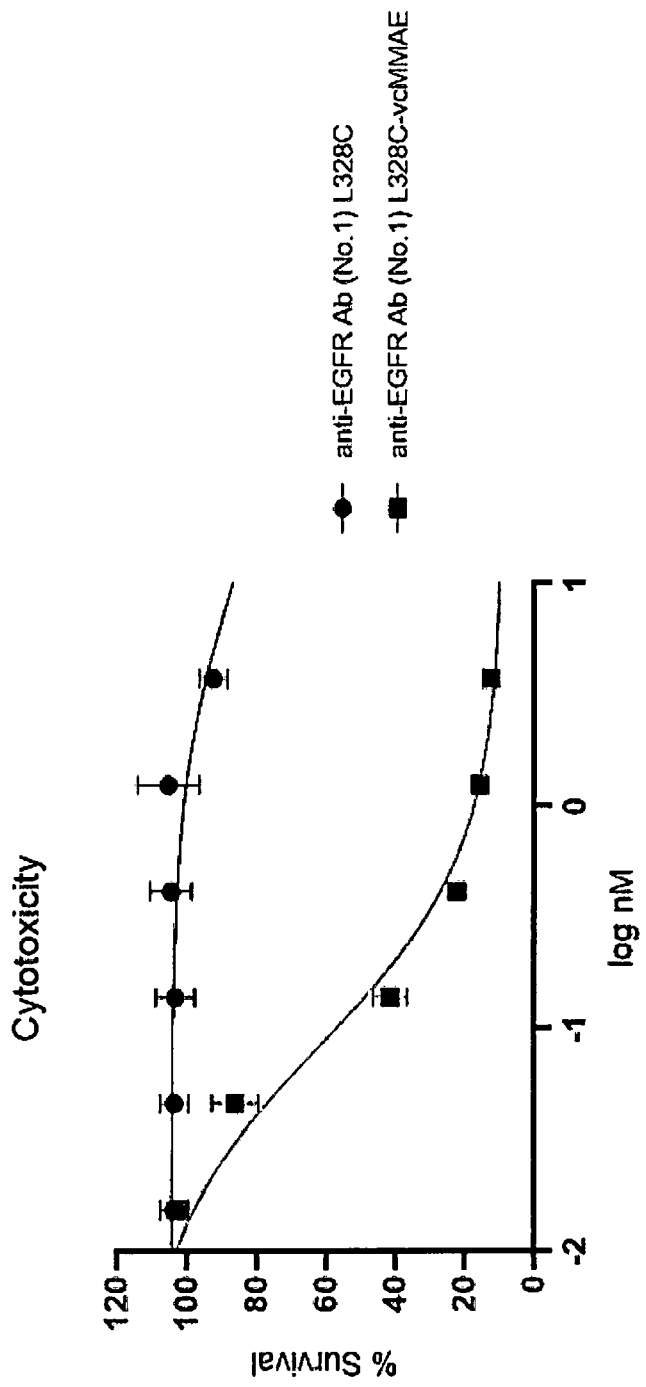
Figure 57. Cytotoxicity mediated by L328C variant of anti-EGFR antibody No. 1 conjugated with vcMMAE.

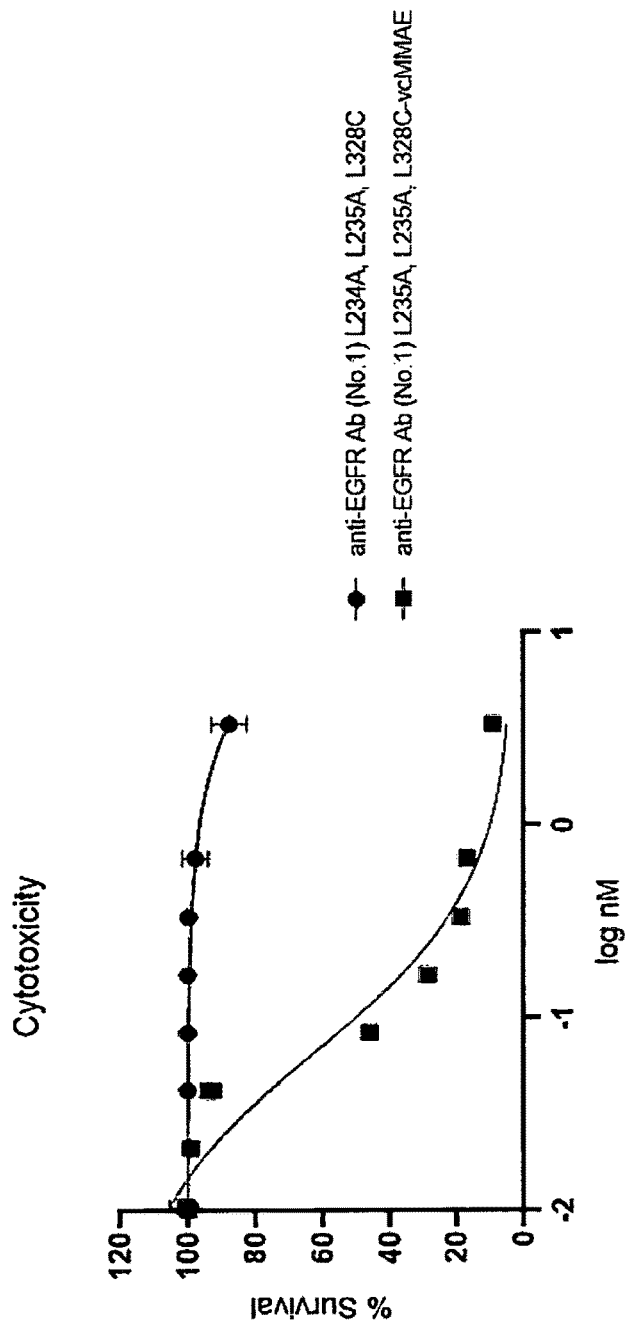
Figure 58. Cytotoxicity mediated by L234A, L235A, L328C variant of anti-EGFR antibody No. 1 conjugated to vcMMAE.

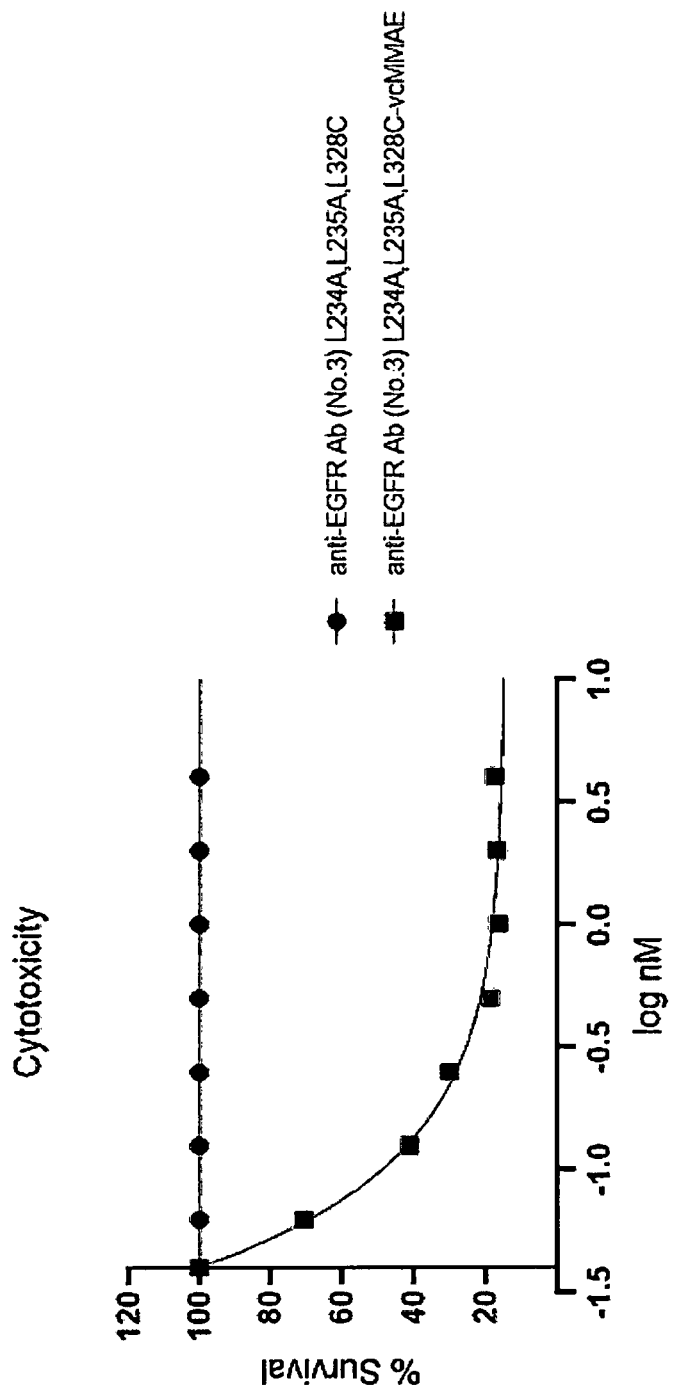
Figure 59. Cytotoxicity mediated by L234A, L235A, L328C variant of anti-EGFR antibody No. 3 conjugated with vcMMAE.

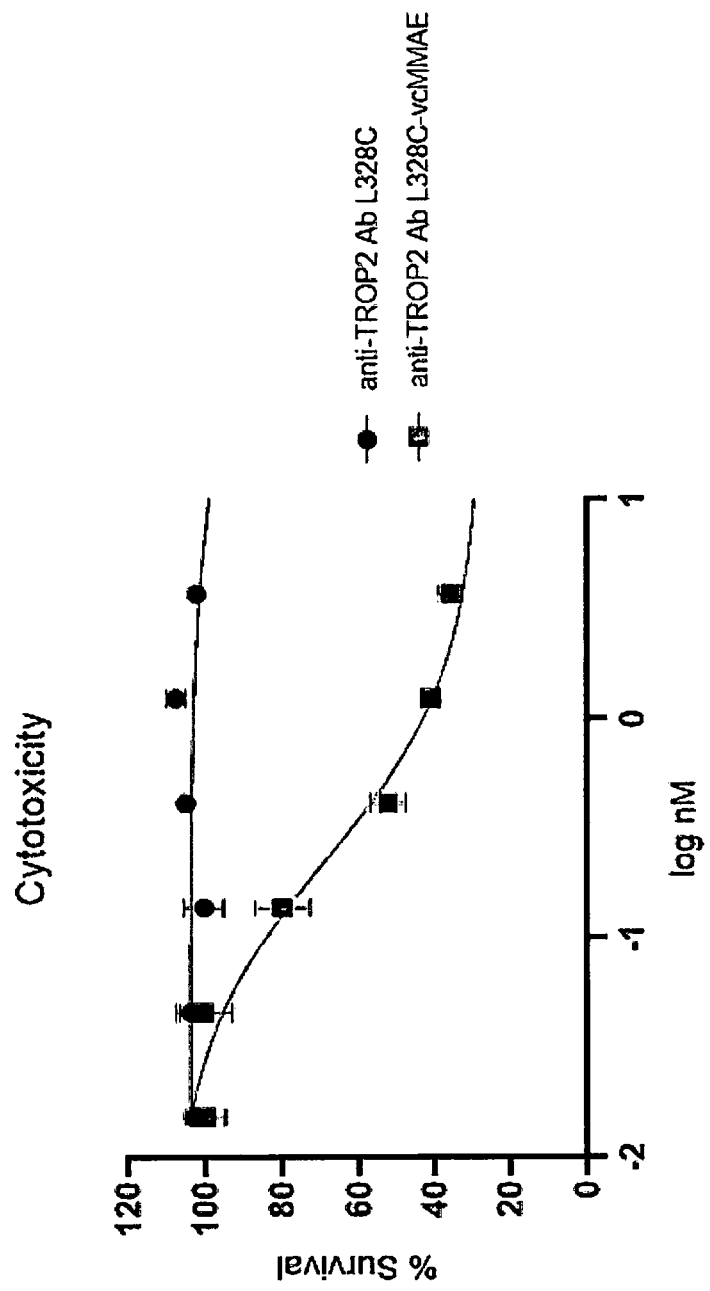
Figure 60. Cytotoxicity mediated by L328C variant of anti-TROP2 antibody conjugated with vcMMAE.

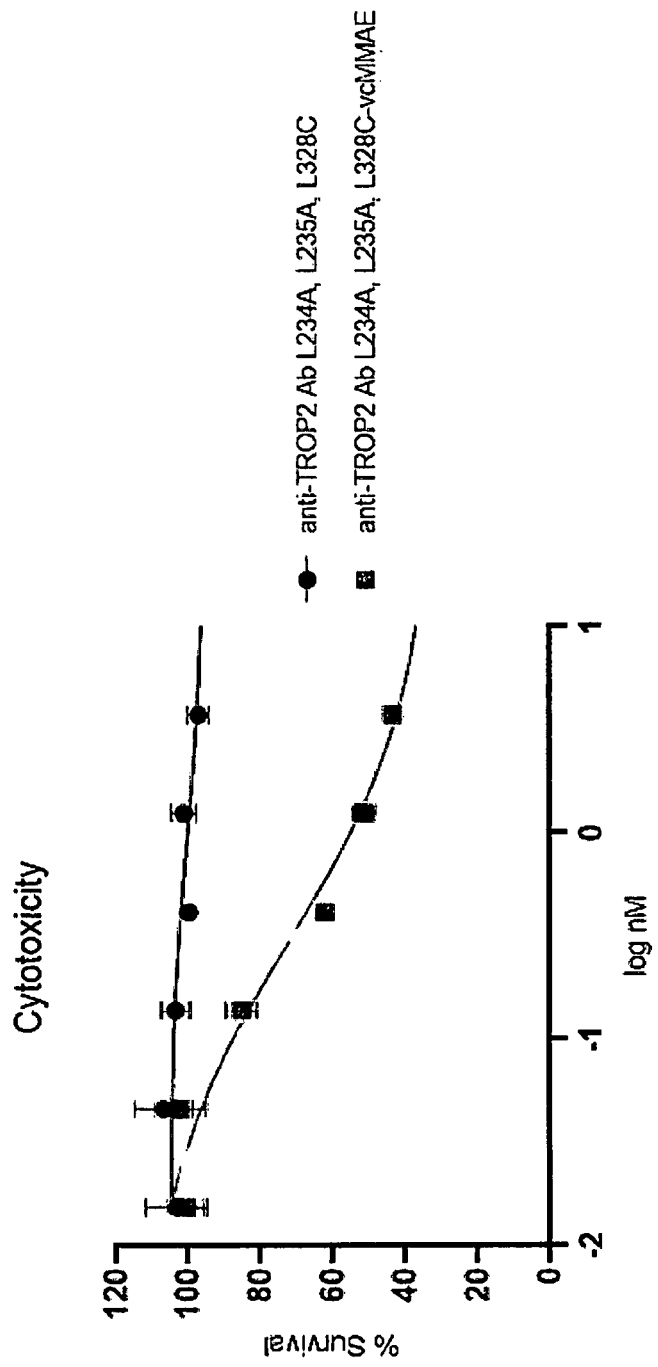
Figure 61. Cytotoxicity mediated by L234A, L235A, L328C variant of anti-Trop2 antibody conjugated with vcMMAE.

SEQUENCE LISTING

<160> NUMBER OF SEQ ID NOS: 30

<210> SEQ ID NO 1
<211> LENGTH: 450
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 450
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Cys Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 450
<212> TYPE: PRT
<213> ORGANISM: Homo sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 4
<211> LENGTH: 450
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                  35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Cys Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 5
<211> LENGTH: 214
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 449
<212> TYPE: PRT
<213> ORGANISM: Homo sapiens

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

```
Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 7
<211> LENGTH: 449
<212> TYPE: PRT
<213> ORGANISM: Homo sapiens

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30
```

```
Asp Tyr Tyr Trp Thr Trp Ile Arg Gln Ser Pro Gly Lys Gly Leu Glu
            35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
 65                  70                  75                  80

Ser Leu Lys Leu Ser Ser Val Thr Ala Ala Asp Thr Ala Ile Tyr Tyr
                 85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Cys Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

Lys

<210> SEQ ID NO 8
<211> LENGTH: 449
<212> TYPE: PRT
<213> ORGANISM: Homo sapiens

<400> SEQUENCE: 8

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

-continued

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 9
<211> LENGTH: 449
<212> TYPE: PRT
<213> ORGANISM: Homo sapiens

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Cys Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 10
<211> LENGTH: 214
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
50                  55                  60
Ser Gly Ser Gly Thr Asp Phe Thr Phe Thr Ile Ser Ser Leu Gln Pro
65                  70                  75                  80
Glu Asp Ile Ala Thr Tyr Phe Cys Gln His Phe Asp His Leu Pro Leu
                85                  90                  95
Ala Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
```

Phe Asn Arg Gly Glu Cys
210

<210> SEQ ID NO 11
<211> LENGTH: 449
<212> TYPE: PRT
<213> ORGANISM: Homo sapiens

<400> SEQUENCE: 11

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

```
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 12
<211> LENGTH: 449
<212> TYPE: PRT
<213> ORGANISM: Homo sapiens

<400> SEQUENCE: 12

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Cys Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 13
<211> LENGTH: 449
<212> TYPE: PRT
<213> ORGANISM: Homo sapiens

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Val Glu Pro Lys Ser Cys Asp Lys
              210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
              260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
              340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
              420                 425                 430

Ala Leu His Asn His Tyr Thr Gln Lys Ser Leu Ser Leu Ser Pro Gly
            435                 440                 445

Lys

<210> SEQ ID NO 14
<211> LENGTH: 449
<212> TYPE: PRT
<213> ORGANISM: Homo sapiens

<400> SEQUENCE: 14

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
              20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
              100                 105                 110

Thr Leu Val Thr Val Ser Ala Ala Ser Thr Lys Gly Pro Ser Val Phe
            115                 120                 125

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Cys Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 15
<211> LENGTH: 214
<212> TYPE: PRT
<213> ORGANISM: Homo sapiens

<400> SEQUENCE: 15

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45
```

```
Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 16
<211> LENGTH: 453
<212> TYPE: PRT
<213> ORGANISM: Homo sapiens

<400> SEQUENCE: 16

Gln Val Gln Leu Gln Gln Ser Gly Ala Glu Val Lys Lys Pro Gly Ser
 1                5                  10                  15

Ser Val Lys Val Ser Cys Lys Ala Ser Gly Tyr Thr Phe Thr Asn Tyr
                 20                  25                  30

Tyr Ile Tyr Trp Val Arg Gln Ala Pro Gly Gln Gly Leu Glu Trp Ile
             35                  40                  45

Gly Gly Ile Asn Pro Thr Ser Gly Gly Ser Asn Phe Asn Glu Lys Phe
 50                  55                  60

Lys Thr Arg Val Thr Ile Thr Ala Asp Glu Ser Ser Thr Thr Ala Tyr
 65                  70                  75                  80

Met Glu Leu Ser Ser Leu Arg Ser Glu Asp Thr Ala Phe Tyr Phe Cys
                 85                  90                  95

Thr Arg Gln Gly Leu Trp Phe Asp Ser Asp Gly Arg Gly Phe Asp Phe
                100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

```
              195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 17
<211> LENGTH: 453
<212> TYPE: PRT
<213> ORGANISM: Homo sapiens

<400> SEQUENCE: 17

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110
```

```
Trp Gly Gln Gly Thr Thr Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Cys Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
        450

<210> SEQ ID NO 18
<211> LENGTH: 453
<212> TYPE: PRT
<213> ORGANISM: Homo sapiens

<400> SEQUENCE: 18

Gln Val Gln Leu Gln Gln Ser Gly Ala Glu Val Lys Lys Pro Gly Ser
1               5                   10                  15
Ser Val Lys Val Ser Cys Lys Ala Ser Gly Tyr Thr Phe Thr Asn Tyr
            20                  25                  30
```

-continued

Tyr Ile Tyr Trp Val Arg Gln Ala Pro Gly Gln Gly Leu Glu Trp Ile
            35                  40                  45

Gly Gly Ile Asn Pro Thr Ser Gly Gly Ser Asn Phe Asn Glu Lys Phe
 50                      55                  60

Lys Thr Arg Val Thr Ile Thr Ala Asp Glu Ser Ser Thr Thr Ala Tyr
 65                  70                  75                  80

Met Glu Leu Ser Ser Leu Arg Ser Glu Asp Thr Ala Phe Tyr Phe Cys
                 85                  90                  95

Thr Arg Gln Gly Leu Trp Phe Asp Ser Asp Gly Arg Gly Phe Asp Phe
                100                 105                 110

Trp Gly Gln Gly Thr Thr Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
           450

<210> SEQ ID NO 19
<211> LENGTH: 453
<212> TYPE: PRT
<213> ORGANISM: Homo sapiens

<400> SEQUENCE: 19

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Cys Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

```
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 20
<211> LENGTH: 219
<212> TYPE: PRT
<213> ORGANISM: Homo sapiens
<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Glu Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 21
<211> LENGTH: 451
<212> TYPE: PRT
<213> ORGANISM: Homo sapiens
<400> SEQUENCE: 21

```
Gln Val Gln Leu Gln Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Tyr
            20                  25                  30
Gly Met Asn Trp Val Lys Gln Ala Pro Gly Gln Gly Leu Lys Trp Met
            35                  40                  45
Gly Trp Ile Asn Thr Tyr Thr Gly Glu Pro Thr Tyr Thr Asp Asp Phe
 50                  55                  60
Lys Gly Arg Phe Ala Phe Ser Leu Asp Thr Ser Val Ser Thr Ala Tyr
 65                  70                  75                  80
Leu Gln Ile Ser Ser Leu Lys Ala Asp Asp Thr Ala Val Tyr Phe Cys
                85                  90                  95
Ala Arg Gly Gly Phe Gly Ser Ser Tyr Trp Tyr Phe Asp Val Trp Gly
                100                 105                 110
Gln Gly Ser Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 22
<211> LENGTH: 451
<212> TYPE: PRT
<213> ORGANISM: Homo sapiens

<400> SEQUENCE: 22

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Cys Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 23
<211> LENGTH: 451
<212> TYPE: PRT
<213> ORGANISM: Homo sapiens

<400> SEQUENCE: 23

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                        260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 24
<211> LENGTH: 451
<212> TYPE: PRT
<213> ORGANISM: Homo sapiens

<400> SEQUENCE: 24

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Cys Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 25
<211> LENGTH: 214
<212> TYPE: PRT
<213> ORGANISM: Homo sapiens

<400> SEQUENCE: 25

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95
```

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 26
<211> LENGTH: 453
<212> TYPE: PRT
<213> ORGANISM: Homo sapiens

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr

```
              245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
450

<210> SEQ ID NO 27
<211> LENGTH: 453
<212> TYPE: PRT
<213> ORGANISM: Homo sapiens

<400> SEQUENCE: 27

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Cys Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 28
<211> LENGTH: 453
<212> TYPE: PRT
<213> ORGANISM: Homo sapiens

<400> SEQUENCE: 28

Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Gln
            20                  25                  30
Ser Ala Ala Trp Asn Trp Ile Arg Gln Ser Pro Ser Arg Gly Leu Glu
        35                  40                  45
Trp Leu Gly Arg Ile Tyr Tyr Arg Ser Lys Trp Tyr Asn Asp Tyr Ala
    50                  55                  60
Leu Ser Val Lys Ser Arg Ile Thr Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 29
<211> LENGTH: 453
<212> TYPE: PRT
<213> ORGANISM: Homo sapiens
```

```
<400> SEQUENCE: 29

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Cys Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

-continued

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 30
<211> LENGTH: 213
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Thr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Ser Trp Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

ANTIBODY COMPOSITIONS COMPRISING Fc MUTATIONS AND SITE-SPECIFIC CONJUGATION PROPERTIES FOR USE IN TREATING CANCER, IMMUNOLOGICAL DISORDERS, AND METHODS THEREOF

CROSS-REFERENCE TO RELATED APPLICATIONS

This application claims priority to U.S. Provisional Patent Application No. 62/973,475 filed 4 Oct. 2019, the contents of which are fully incorporated by reference herein.

SUBMISSION OF SEQUENCE LISTING

The content of the following submissions are fully incorporated by reference herein in its entirety: a paper copy of the Sequence Listing recorded Oct. 2, 2020. Additionally, the content of a computer readable form (CRF) of the Sequence Listing entitled COPY 1 REPLACEMENT on ASCII text file (file name: 1221-20004.00—SEQ LIST—As-Filed 02-Oct-2020.txt, date recorded Oct. 5, 2021, size: 104 KB) and the content of a computer readable form (CRF) of the Sequence Listing entitled COPY 2 REPLACEMENT on ASCII text file (file name: 1221-20004.00—SEQ LIST—As-Filed 02-Oct-2020.txt, date recorded Oct. 5, 2021, size: 104 KB).

STATEMENT OF RIGHTS TO INVENTIONS MADE UNDER FEDERALLY SPONSORED RESEARCH

Not applicable.

FIELD OF THE INVENTION

The invention described herein relates to antibodies, antigen-binding fragments thereof, antibody drug conjugates (ADCs), and antibody boron conjugates (ABCs) that have been engineered to include a plurality of functional properties, including Fc silencing and site-specific conjugation. The invention further relates to prognostic, prophylactic and therapeutic methods and compositions useful in the treatment of cancers and immunological and neurological disorders.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. By 2040 it is estimated that each year there will be over 16 million cancer deaths worldwide (source; International Agency for Research on Cancer, 2018) thus surpassing heart disease as the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both genders in all ages worldwide (GLOBOCAN 2018). These and virtually all other carcinomas share a common lethal feature in that they metastasize to sites distant from the primary tumor and with very few exceptions. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

In fighting cancer and other medical conditions, the therapeutic utility of monoclonal antibodies (mAbs) (G. KOHLER and C. MILSTEIN, Nature 256:495-497 (1975)) is being realized. MAbs have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. ALZARI et al., Annual Rev. Immunol., 6:555-580 (1988)).

In general, antibodies act by a number of mechanisms, most of which engage other arms of the immune system. Antibodies can simply block interactions of molecules or they can activate the classical complement pathway (known as complement dependent cytotoxicity or CDC) by interaction of the C1q on the C1 complex with clustered antibodies. Critically antibodies also act as a link between the antibody-mediated and cell-mediated immune responses through engagement of Fc receptors.

Fc engineering approaches have been used to determine the key interaction sites for the Fc domain with Fc gamma receptors and C1q and then mutate these positions to reduce or abolish binding in an effort to improve therapeutic properties such as modulating the effector function and reduced toxicity, etc. See, HEZAREH, et. al., J. Virol. 75(24): 12161-8 (December 2001) and OGANESYAN, et. al., Acta Crystallographica. D. Biol Crystallogr, 64:(Pt. 6):700-4 (June 2008).

In addition, antibody-drug conjugates (ADCs) are an emerging class of targeted therapeutics having an improved therapeutic index over traditional chemotherapy. Drugs and linkers have been the focus of ADC development, in addition to (monoclonal) antibody (mAb) and target selection. Recently, however, the importance of conjugate homogeneity has been explored. It has been reported that the pharmacological profile of ADCs may be improved by applying site-specific conjugation technologies that make use of surface-exposed cysteine residues engineered into antibodies that are then conjugated to a linker drug, resulting in site-specifically conjugated ADCs with defined drug-to-antibody ratios (DARs). Relative to the heterogeneous mixtures created using conventional lysine and cysteine conjugation methodologies, site-specifically conjugated ADCs have generally demonstrated at least equivalent in vivo potency, improved PK, and an expanded therapeutic window.

The prior art discloses several approaches to obtaining site specific conjugation and resulting ADCs. See, for example, WO2006/034488 (Genentech), SUTHERLAND, et. al., Blood 122(8):1455-1463 (2013), WO2014/124316 (Novartis), and US2017/0080103 (Synthon Biopharmaceuticals), etc.

In all of the prior art methods disclosed thus far, the emphasis was put on site conjugating linker drugs at surface/solvent-exposed positions, at positions showing high thiol reactivity, and at positions in specifically the constant regions of monoclonal antibodies, with the aim of improving homogeneity and pharmacokinetic properties.

Even though the above-described conventional lysine and cysteine conjugation methods have led to FDA-approved antibody-drug conjugates and they are being used for constructing most of a large number of ADCs currently in preclinical and clinical trials, there is still a need for new conjugation strategies with the aim to (further) improve the physicochemical, pharmacokinetic, pharmacological, and/or toxicological properties of ADCs to obtain ADCs having acceptable antigen binding properties, in vivo efficacy, therapeutic index, and/or stability.

From the aforementioned, it will be readily apparent to those skilled in the art that a new treatment paradigm is needed in the treatment of cancers and immunological diseases. By using modern antibody engineering techniques as well as new conjugation methodologies, a new class of antibodies can be achieved with the overall goal of more effective treatment, reduced side effects, and lower production costs.

Given the current deficiencies known in the art, it is an object of the present invention to provide new and improved antibodies and binding ligands and methods of treating cancer(s), immunological disorders, and other diseases utilizing antibodies engineered with triple mutations to reduce antibody effector function and include site specific conjugations points.

SUMMARY OF THE INVENTION

The invention provides antibodies, antigen-binding fragments, antibody drug conjugates (ADCs), antibody immune modifying conjugates, and antibody boron conjugates (ABCs) that bind to proteins, including but not limited to Her2, EGFR, Trop2, CDH3, and polypeptide fragments of proteins including but not limited to Her2, EGFR, Trop2, CDH3, and. In some embodiments, the invention comprises fully human antibodies conjugated with a therapeutic agent. In some embodiments, the invention comprises fully human antibodies conjugated with a borylated compound. In some embodiments, the antibodies have been engineering to reduce effector function via Fc silencing. In some embodiments, the antibodies contain a site-specific mutation capable of conjugation to a drug moiety. In some embodiments, the antibodies comprise a triple mutation whereby the Fc is silenced, and a site-specific mutation is inserted for conjugation to a drug moiety. In a further embodiment, the triple mutation comprises L234A, L235A, L328C.

The invention further provides various immunogenic or therapeutic compositions, such as antibodies, antibody drug conjugates, and strategies for treating cancers that express Her2, EGFR, Trop2, CDH3, and other Tumor Associated Antigens (TAAs) such as those listed in Table IV.

In another embodiment, the present disclosure teaches methods of synthesizing triple mutant antibodies.

In another embodiment, the present disclosure teaches methods of synthesizing triple mutant antibodies and conjugating a drug moiety at a site-specific location thereto.

In another embodiment, the present disclosure teaches methods of synthesizing single mutant antibodies.

In another embodiment, the present disclosure teaches methods of synthesizing single mutant antibodies and conjugating a drug moiety at a site-specific location thereto.

In another embodiment, the present disclosure teaches methods of treating cancer(s), immunological disorders and other diseases in humans.

BRIEF DESCRIPTION OF THE FIGURES

FIG. 1. Anti-Her2 Mab and Fc Variants: Fc variants do not affect target binding.

FIG. 2. Anti-EGFR Mab No. 1 and Fc Variants: Fc variants do not affect target binding.

FIG. 3. Anti-EGFR Mab No. 2 and Fc Variants: Fc variants do not affect target binding.

FIG. 4. Anti-EGFR Mab No. 3 and Fc Variants: Fc variants do not affect target binding.

FIG. 5. Anti-Trop2 Mab and Fc Variants: Fc variants do not affect target binding.

FIG. 6. Anti-CDH3 Mab and Fc Variants: Fc variants do not affect target binding.

FIG. 7. Anti-Her2 Mab and Fc Variants: A complete inhibition of FcγRI binding is observed for the triple mutant.

FIG. 8. Anti-EGFR Mab No. 1 and Fc Variants: A complete inhibition of FcγRI binding is observed for the triple mutant.

FIG. 9. Anti-EGFR Mab No. 2 and Fc Variants: A complete inhibition of FcγRI binding is observed for the triple mutant.

FIG. 10. Anti-EGFR Mab No. 3 and Fc Variants: A near complete inhibition of FcγRI binding is observed for the triple mutant.

FIG. 11. Anti-Trop2 Mab and Fc Variants: A complete inhibition of FcγRI binding is observed for the triple mutant.

FIG. 12. Anti-CDH3 Mab and Fc Variants: A near complete inhibition of FcγRI binding is observed for the triple mutant.

FIG. 13. Anti-Her2 Mab and Fc Variants: Suppression of FcγRIIA binding is observed for the single and triple mutant.

FIG. 14. Anti-EGFR Mab No. 1 and Fc Variants: Suppression of FcγRIIA binding is observed for the single and triple mutant.

FIG. 15. Anti-Trop2 Mab and Fc Variants: Suppression of FcγRIIA binding is observed for the single and triple mutant.

FIG. 16. Anti-CDH3 Mab and Fc Variants: Suppression of FcγRIIA binding is observed for the single and triple mutant.

FIG. 17. Anti-Her2 Mab and Fc Variants: An inhibition of FcγRIIIa binding is observed for the single and triple mutant.

FIG. 18. Anti-EGFR Mab No. 1 and Fc Variants: An inhibition of FcγRIIIa binding is observed for the single and triple mutant.

FIG. 19. Anti-EGFR Mab No. 2 and Fc Variants: An inhibition of FcγRIIIa binding is observed for the single and triple mutant.

FIG. 20. Anti-EGFR Mab No. 3 and Fc Variants: An inhibition of FcγRIIIa binding is observed for the single and triple mutant.

FIG. 21. Anti-Trop2 Mab and Fc Variants: An inhibition of FcγRIIIa binding is observed for the single and triple mutant.

FIG. 22. Anti-CDH3 Mab and Fc Variants: An inhibition of FcγRIIIa binding is observed for the single and triple mutant.

FIG. 23. Anti-Her2 Mab and Fc Variants: A substantial reduction in FcRn binding is not observed with Fc variants.

FIG. 24. Anti-EGFR Mab No. 1 and Fc Variants: A substantial reduction in FcRn binding is not observed with Fc variants.

FIG. 25. Anti-EGFR Mab No. 2 and Fc Variants: A substantial reduction in FcRn binding is not observed with Fc variants.

FIG. 26. Anti-EGFR Mab No. 3 and Fc Variants: A substantial reduction in FcRn binding is not observed with Fc variants.

FIG. 27. Anti-Trop2 Mab and Fc Variants: A substantial reduction in FcRn binding is not observed with Fc variants.

FIG. 28. Anti-CDH3 Mab and Fc Variants: A substantial reduction in FcRn binding is not observed with Fc variants.

FIG. 29. Binding kinetic analysis of anti-Her2 antibody and Fc variants for FcγRI, IIA, IIB, IIIA, IIIB and FcRn. The Triple Mutant exhibits substantial binding inhibition to all FcγR isoforms but not for FcRn FIG. 30. Binding kinetic analysis of anti-Her2 antibody and Fc variants for FcγRI. The dissociation rate is faster for the triple mutation as compared to wild-type and single mutation.

FIG. 31. Anti-HER2 mAb and Fc variants: Reduction in ADCC is observed with Fc variants.

FIG. 32. Anti-EGFR mAb No. 1 and Fc variants: Reduction in ADCC is observed with Fc variants.

FIG. 33. Anti-Trop2 mAb and Fc variants: Reduction in ADCC is observed with Fc variants.

FIG. 34. Anti-CDH3 mAb and Fc variants: Reduction in ADCC is observed with Fc variants.

FIG. 35. Anti-HER2 mAb and Fc variants: Reduction in CDC is observed with Fc variants.

FIG. 36. Anti-EGFR mAb No. 1 and Fc variants: Reduction in CDC is observed with Fc variants.

FIG. 37. Anti-Trop2 mAb and Fc variants: Reduction in CDC is observed with Fc variants.

FIG. 38. Anti-CDH3 mAb and Fc variants: Reduction in CDC is observed with Fc variants.

FIG. 39. Anti-HER2 mAb and Fc variants: Reduction in C1q Binding is observed with Fc variants.

FIG. 40. Anti-EGFR mAb No. 1 and Fc variants: Reduction in C1q Binding is observed with Fc variants.

FIG. 41. Anti-Trop2 mAb and Fc variants: Reduction in C1q Binding is observed with Fc variants.

FIG. 42. Anti-CDH3 mAb and Fc variants: Reduction in C1q Binding is observed with Fc variants.

FIG. 43. Reverse-Phase Column Chromatography Profile of anti-Her2 Mab triple mutant conjugated with a proprietary payload (LOL1). Superimposed UV traces of unconjugated triple mutant anti-HER2 mAb (Peak 1) conjugated triple mutant anti-HER2 mAb (Peak 2).

FIG. 44. Intact mass analysis of LOL1-conjugated triple mutant anti-HER2 mAb Confirmed That the Conjugate is 100% Site-Specific. (A). Full spectrum, (B). Zoomed LC region, (C). Zoomed HC region.

FIG. 45. Reverse-Phase Column Chromatography Profile for L328C variants of anti-HER2 (A) and anti-EGFR mAbs (B) conjugated with vcMMAE. The heavy chain with a single payload (H1) is the principle species suggesting that the conjugation is site-specific, and the payload resides on the Cys328 and not within the hinge region.

FIG. 46. Reverse-Phase Column Chromatography Profile for L328C variant of anti-TROP2 mAb conjugated with vcMMAE. (A). Light Chain (Peak 1), Unconjugated heavy chain (Peak 2), conjugated heavy chain with 1 payload (Peak 3); Conjugated heavy chains with 2 and 3 payloads (Peaks 4-5). (B). Superimposed UV214 nm traces of mAb and ADC. Unconjugated L328C variant of anti-TROP2 antibody (black); vcMMAE conjugated L328C variant of anti-TROP2 antibody (red).

FIG. 47. Reverse-Phase HPLC analysis of triple mutant anti-TROP2 mAb conjugated with vcMMAE. (A). Light Chain (Peak 1), Unconjugated heavy chain (Peak 2), conjugated heavy chain with 1 payload (Peak 3); Conjugated heavy chains with 2 and 3 payloads, respectively (Peaks 4-5). (B). Superimposed UV214 nm traces of mAb and ADC. Unconjugated L328C variant of anti-TROP2 antibody (black); vcMMAE conjugated L328C variant of anti-TROP2 antibody (red)

FIG. 48. Reverse-Phase Column Chromatography Profiles for L234A, L235A, L328C variants of anti-EGFR mAbs conjugated with vcMMAE. (A). Profile for unconjugated anti-EGFR mAb No. 3 with triple Fc mutation. (B). Profile for unconjugated anti-EGFR mAb No. 1 with triple Fc mutation. (C). Profile for vcMMAE conjugated anti-EGFR mAb No. 3 with triple Fc mutation. (D). Profile for vcMMAE conjugated anti-EGFR mAb No. 1 with triple Fc mutation FIG. 49. An example of the peak assignment and DAR calculation based on Reverse-Phase column chromatography data (provided in FIG. 48). The unconjugated mAbs (control) were used to identify both the retention time and the UV250/280 ratio for both the heavy and the light chain. These parameters were required for correct peak assignment and DAR determination.

FIG. 50. A summary of analytical attributes of the resulting ADCs: Average DAR, percent monomer by size exclusion chromatography (SEC), and percent of DAR1 heavy chain is shown for vcMMAE or LOL1 conjugated mAbs with single or triple Fc variants.

FIG. 51. Characteristic daughter ions following fragmentation of a vcMMAE-peptide.

FIG. 52. Sequence coverage of anti-EGFR antibody No. 1 with triple mutant conjugated with vcMMAE. (A). Heavy Chain, (B). Light Chain.

FIG. 53. Representative TIC Chromatograms of peptides following digestion with trypsin for (A). non-conjugated anti-EGFR antibody No. 1 with triple mutation, (B) vcMMAE-conjugated anti-EGFR antibody No. 1 with triple mutation.

FIG. 54. Conjugation site for anti-EGFR antibody No. 1 with triple mutation was confirmed through MS/MS of the ACPAPIEK heavy chain peptide. Full MS (A, C) and fragmentation by MS/MS (B, D) of the ACPAPIEK-Carbamidomethyl (e.g. alkylated mAb, A, B) and ACPAPIEK-vcMMAE (C,D) peptide is shown. The fragments representing the peptide or vcMMAE are indicated by filled or hollow arrows, respectively.

FIG. 55. Confirmation of site of conjugation in anti-EGFR antibody No. 1 with single mutation ADC via MS/MS of the ACPAPIEK heavy chain peptide. Full MS (A, C) and fragmentation by MS/MS (B, D) of the ACPAPIEK-Carbamidomethyl (e.g. alkylated mAb, A,B) and ACPAPIEK-vcMMAE (C,D) peptide is shown. The fragments representing the peptide or vcMMAE are indicated by filled or hollow arrows, respectively.

FIG. 56. Cytotoxicity mediated by L328C variant of anti-HER2 antibody conjugated with vcMMAE. HCC1954 (Her2/neu positive) cells were incubated for 72 to 96 hours and the percent of surviving cells was measured using CellTiter-Glo cell viability assay.

FIG. 57. Cytotoxicity mediated by L328C variant of anti-EGFR antibody No. 1 conjugated with vcMMAE. MDA-MB-468 (EGFR positive) cells were incubated for 72 to 96 hours and the percent of surviving cells was measured using CellTiter-Glo cell viability assay.

FIG. 58. Cytotoxicity mediated by L234A, L235A, L328C variant of anti-EGFR antibody No. 1 conjugated with vcMMAE. MDA-MB-468 (EGFR positive) cells were incubated for 72 to 96 hours and the percent of surviving cells was measured using CellTiter-Glo cell viability assay.

FIG. 59. Cytotoxicity mediated by L234A, L235A, L328C variant of anti-EGFR antibody No. 3 conjugated with vcMMAE. MDA-MB-468 (EGFR positive) cells were incubated for 72 to 96 hours and the percent of surviving cells was measured using CellTiter-Glo cell viability assay FIG. 60. Cytotoxicity mediated by L328C variant of anti-Trop2 antibody conjugated with vcMMAE. SK BR3 (TROP2 positive) cells were incubated for 72 to 96 hours and the percent of surviving cells was measured using CellTiter-Glo cell viability assay.

FIG. 61. Cytotoxicity mediated by L234A, L235A, L328C variant of anti-Trop2 antibody conjugated with vcMMAE. SK BR3 (TROP2 positive) cells were incubated for 72 to 96 hours and the percent of surviving cells was measured using CellTiter-Glo cell viability assay

DETAILED DESCRIPTION OF THE INVENTION

Outline of Sections
I.) Definitions
II.) Antibodies
III.) Fc Mutations to Modify Effector Function
IV.) Antibody-Drug-Conjugates
V.) Site-Specific Conjugation Formats for ADCs
VI.) Linker Units
VII.) The Stretcher Unit
VIII.) The Amino Acid Unit
IX.) The Spacer Unit
X.) The Drug Unit
XI.) Methods of Determining Cytotoxic Effect of ADCs
XII.) Treatment of Cancer(s) Expressing Her2, EGFR, Trop2, CDH3, and TAAs
XIII.) Combination Therapy
XIV.) KITS/Articles of Manufacture

I. Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "antibody" is used in the broadest sense unless clearly indicated otherwise. Therefore, an "antibody" can be naturally occurring or man-made such as monoclonal antibodies produced by conventional hybridoma or transgenic mice technology. Her2, EGFR, Trop2, CDH3, and/or TAA antibodies comprise monoclonal and polyclonal antibodies as well as fragments containing the antigen-binding domain and/or one or more complementarity determining regions of these antibodies. As used herein, the term "antibody" refers to any form of antibody or fragment thereof that specifically binds Her2, EGFR, Trop2, CDH3, and/or any TAA and/or exhibits the desired biological activity and specifically covers monoclonal antibodies (including full length monoclonal antibodies), polyclonal antibodies, multispecific antibodies (e.g., bispecific antibodies), and antibody fragments so long as they specifically bind Her2, EGFR, Trop2, CDH3, and/or exhibit the desired biological activity. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is an IgG1, IgG2, IgG3, or IgG4 antibody. The antibodies useful in the present methods and compositions can be generated in cell culture, in phage, in yeast or in various animals, including but not limited to cows, rabbits, goats, mice, rats, hamsters, guinea pigs, sheep, dogs, cats, monkeys, chimpanzees, and apes. Therefore, in one embodiment, an antibody of the present invention is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and at least one VH region in the host cell. Exemplary descriptions of recombinant means of antibody generation and production include Delves, ANTIBODY PRODUCTION: ESSENTIAL TECHNIQUES (Wiley, 1997); SHEPARD, et al., MONOCLONAL ANTIBODIES (Oxford University Press, 2000); GODING, MONOCLONAL ANTIBODIES: PRINCIPLES AND PRACTICE (Academic Press, 1993); and CURRENT PROTOCOLS IN IMMUNOLOGY (John Wiley & Sons, most recent edition). An antibody of the present invention can be modified by recombinant means to increase efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and ANGAL, et al., Mol. Immunol. 30: 105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to normal or defective FLT3. See e.g., ANTIBODY ENGINEERING: A PRACTICAL APPROACH (Oxford University Press, 1996). Suitable antibodies with the desired biologic activities can be identified using the following in vitro assays including but not limited to proliferation, migration, adhesion, soft agar growth, angiogenesis, cell-cell communication, apoptosis, transport, signal transduction, and the following in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays. They can also be used to quantify the Her2, EGFR, Trop2, and/or CDH3 or its receptor.

The term "antigen-binding fragment" or "antibody fragment" of an antibody (or simply "antibody portion"), as used herein, refers to one or more fragments of a Her2, EGFR, Trop2, CDH3, and/or a TAA antibody that retain the ability to specifically bind to an antigen (e.g., Her2, EGFR, Trop2, CDH3, and/or variants). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (WARD et al., (1989) Nature 341:544-546), which consists of a $V_H$ domain; and (vi) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., BIRD et. al. (1988) Science 242:423-426; and HUSTON et. al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

The term "Fc", as used herein, refers to a region comprising a hinge region, $CH_2$ and/or $CH_3$ domains.

As used herein, any form of the "antigen" can be used to generate an antibody that is specific for Her2, EGFR, Trop2, CDH3, and/or any TAA of the invention. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may be genomic or non-genomic (e.g., cDNA) and encodes at least a portion of the extracellular domain. As used herein, the term "portion", in the context of an antigen, refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids. In one embodiment, the antibody of the methods and compositions herein specifically bind at least a portion of the extracellular domain of the target of interest.

The antibodies or antigen binding fragments thereof provided herein may constitute or be part of a "bioactive agent." As used herein, the term "bioactive agent" refers to any synthetic or naturally occurring compound that binds the antigen and/or enhances or mediates a desired biological effect to enhance cell-killing toxins. In one embodiment, the binding fragments useful in the present invention are biologically active fragments. As used herein, the term "biologically active" refers to an antibody or antibody fragment that is capable of binding the desired antigenic epitope and directly or indirectly exerting a biologic effect. Direct effects include, but are not limited to the modulation, stimulation, and/or inhibition of a growth signal, the modulation, stimulation, and/or inhibition of an anti-apoptotic signal, the modulation, stimulation, and/or inhibition of an apoptotic or necrotic signal, modulation, stimulation, and/or inhibition the ADCC cascade, and modulation, stimulation, and/or inhibition the CDC cascade and/or Fc silencing.

The term "specifically binds", as used herein in relation to antigen binding, proteins means that the antigen binding protein binds to the target as well as a discrete domain, or discrete amino acid sequence, within the target with no or insignificant binding to other (for example, unrelated) proteins. This term, however, does not exclude the fact that the antibodies or binding fragments thereof may also be cross-reactive with closely related molecules. The antibodies and fragments thereof as well as antibody drug conjugates comprising these described herein may specifically bind to Her2, EGFR, Trop2, CDH3, and/or a TAA disclosed herein, with at least 2, 5, 10, 50, 100, or 1000-fold greater affinity than they bind to closely related molecules.

"Bispecific" antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., MILSTEIN et. al., Nature 305:537-39 (1983). Alternatively, bispecific antibodies can be prepared using chemical linkage. See, e.g., BRENNAN, et. al., Science 229:81 (1985). Bispecific antibodies include bispecific antibody fragments. See, e.g., HOLLINGER, et. al., Proc. Natl. Acad. Sci. U.S.A. 90:6444-48 (1993), GRUBER, et. al., J. Immunol. 152:5368 (1994).

The monoclonal antibodies described herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity (U.S. Pat. No. 4,816,567; and MORRISON et. al., Proc. Natl. Acad. Sci. USA 81: 6851-6855 (1984)).

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Tumors may be hematopoietic tumor, for example, tumors of blood cells or the like, meaning liquid tumors. Specific examples of clinical conditions based on such a tumor include leukemia such as chronic myelocytic leukemia or acute myelocytic leukemia; myeloma such as multiple myeloma; lymphoma and the like.

The term "therapeutic agent" refers to all agents that provide a therapeutic benefit and/or are therapeutically effective as defined herein. A therapeutic agent may, for example, reverse, ameliorate, alleviate, inhibit or limit the progress of, or lessen the severity of, a disease, disorder, or condition, or affect or improve or ameliorate one or more symptoms of disease, such as cancer. Such an agent may be cytotoxic or cytostatic. The term includes, but is not limited to, chemotherapeutic agents, anti-neoplastic agents and "Drug Unit" agents as defined herein.

The term "anti-neoplastic agent" refers to all agents that provide a therapeutic benefit and/or are therapeutically effective, as defined herein, in the treatment of a neoplasm or cancer.

The term "Chemotherapeutic Agent" refers to all chemical compounds that are effective in inhibiting tumor growth. Non-limiting examples of chemotherapeutic agents include alkylating agents; for example, nitrogen mustards, ethyleneimine compounds and alkyl sulphonates; antimetabolites, for example, folic acid, purine or pyrimidine antagonists; mitotic inhibitors, for example, anti-tubulin agents such as vinca alkaloids, auristatins and derivatives of podophyllotoxin; cytotoxic antibiotics; compounds that damage or interfere with DNA expression or replication, for example, DNA minor groove binders; and growth factor receptor antagonists. In addition, chemotherapeutic agents include cytotoxic agents (as defined herein), antibodies, biological molecules and small molecules.

The terms "complementarity determining region," and "CDR," are known in the art to refer to non-contiguous sequences of amino acids within antibody variable regions, which confer antigen specificity and binding affinity. In general, there are three (3) CDRs in each heavy chain variable region (CDR-H1, CDR-H2, CDR-H3) and three (3) CDRs in each light chain variable region (CDR-L1, CDR-L2, CDR-L3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), AL-LAZIKANI et. al., (1997) JMB 273, 927-948 ("Chothia" numbering scheme), MACCALLUM et. al., *J. Mol. Biol.* 262:732-745 (1996), "Antibody-antigen interactions: Contact analysis and binding site topography," *J. Mol. Biol.* 262, 732-745." (Contact" numbering scheme), LEFRANC M. P. et. al., "IMGT unique numbering for immunoglobulin and T cell receptor variable domains and Ig superfamily V-like domains," *Dev Comp Immunol*, 2003 January; 27(1):55-77 ("IMGT" numbering scheme), and HONEGGER A. and PLICKTHUN A., "Yet another numbering scheme for immunoglobulin variable domains: an automatic modeling and analysis tool," *J Mol Biol*, 2001 Jun. 8; 309(3):657-70, (AHo numbering scheme).

The boundaries of a given CDR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method.

As used herein, the term "conservative substitution" refers to substitutions of amino acids and/or amino acid sequences that are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., WATSON, et. al., MOLECU- LAR BIOLOGY OF THE GENE, The Benjamin/Cummings Pub. Co., p. 224 (4th Edition 1987)). Such exemplary substitutions are preferably made in accordance with those set forth in Table II and Table(s) Ill. For example, such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" 2nd ED. Lubert Stryer ed (Stanford University); HENIKOFF et. al., PNAS 1992 Vol 8910915-10919; LEI et. al., J Biol Chem 1995 May 19; 270(20):11882-6). Other substitutions are also permissible and may be determined empirically or in accord with known conservative substitutions.

The term "cytotoxic agent" refers to a substance that inhibits or prevents the expression activity of cells, function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, ricin, ricin A-chain, combrestatin, duocarmycins, dolastatins, doxorubicin, daunorubicin, taxols, cisplatin, cc1065, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Sapaonaria officinalis* inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$, and radioactive isotopes of Lu including $Lu^{177}$.

Antibodies, including antibodies of the invention, may also be conjugated to any of the aforementioned cytotoxic agents and also to an anti-cancer pro-drug activating enzyme capable of converting the pro-drug to its active form.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and HOLLINGER et. al., Proc. Natl. Acad. Sci. USA 90:6444-48 (1993).

The term "homolog" refers to a molecule which exhibits homology to another molecule, by for example, having sequences of chemical residues that are the same or similar at corresponding positions.

The term "identical" or "sequence identity" indicates the degree of identity between two nucleic acid or two amino acid sequences when optimally aligned and compared with appropriate insertions or deletions.

The "percent identity" between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below. The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers, et al., Comput. Appi. Biosci., 4:11-17 (1988), which has been incorporated into the ALIGN program (version 2.0), using a PAM120 weight residue table, a gap length penalty of 12 and a gap penalty of 4. In addition, the percent identity between two amino acid sequences can be determined using the NEEDLEMAN, et. al., J. Mol. Biol. 48:444-453 (1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence that is 100% identical to the reference sequence, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein by the numerical percent of the respective percent identity (divided by 100) and subtracting that product from said total number of nucleotides in the reference polynucleotide sequence, or: $n_n \leq x_n - (x_{ny})$, wherein $n_n$ is the number of nucleotide alterations, $x_n$ is the total number of nucleotides in the reference polynucleotide sequence as described herein (see the nucleic acid sequences in the "Sequence Listing" for exemplary reference polynucleotides sequences), and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, is the symbol for the multiplication operator, and wherein any non-integer product of $x_n$ and y is rounded down to the nearest integer prior to subtracting it from $x_n$. Similarly, a polypeptide sequence may be identical to a polypeptide reference sequence as described herein, that is 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence by the numerical percent of the respective percent identity (divided by 100) and then subtracting that product from said total number of amino acids in the polypeptide reference sequence as described herein, or: $n_a \leq x_a - (x_{ay})$, wherein $n_a$ is the number of amino acid alterations, $x_a$ is the total number of amino acids in the reference polypeptide sequence, and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, is the symbol for the multiplication operator, and wherein any non-integer product of $x_a$ and y is rounded down to the nearest integer prior to subtracting it from $x_a$. The percent identity may be determined across the length of the sequence. As defined herein the term "over 75% identical" includes over 75%, 80%, 85%, 95% and 99% identity as well as all discrete values, and discrete subranges, with in this range.

In one embodiment, the antibody provided herein is a "human antibody." As used herein, the term "human antibody" refers to an antibody in which essentially the entire sequences of the light chain and heavy chain sequences, including the complementary determining regions (CDRs), are from human genes. In one embodiment, human monoclonal antibodies are prepared by the trioma technique, the human B-cell technique (see, e.g., KOZBOR, et. al., Immunol. Today 4: 72 (1983), EBV transformation technique (see, e.g., COLE et. al. MONOCLONAL ANTIBODIES AND CANCER THERAPY 77-96 (1985)), or using phage display (see, e.g., MARKS et. al., J. Mol. Biol. 222:581 (1991)). In a specific embodiment, the human antibody is generated in a transgenic mouse. Techniques for making such partially to fully human antibodies are known in the art and any such techniques can be used. According to one particularly preferred embodiment, fully human antibody sequences are made in a transgenic mouse engineered to express human heavy and light chain antibody genes. An exemplary description of preparing transgenic mice that produce human antibodies found in Application No. WO 02/43478 and U.S. Pat. No. 6,657,103 (Abgenix) and its progeny. B cells from transgenic mice that produce the desired antibody can then be fused to make hybridoma cell lines for continuous production of the antibody. See, e.g., U.S. Pat. Nos. 5,569, 825; 5,625,126; 5,633,425; 5,661,016; and 5,545,806; and JAKOBOVITS, Adv. Drug Del. Rev. 31:33-42 (1998); GREEN, et. al., J. Exp. Med. 188:483-95 (1998).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., CABILLY, U.S. Pat. No. 4,816, 567; QUEEN, et. al. (1989) Proc. Nat'l Acad. Sci. USA 86:10029-10033; and ANTIBODY ENGINEERING: A PRACTICAL APPROACH (Oxford University Press 1996).

The terms "inhibit" or "inhibition of" as used herein means to reduce by a measurable amount, or to prevent entirely.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites and are meant to include stage D disease under the AUA system and stage T×N×M+ under the TNM system.

The term "modified", as used herein refers to the presence of a change to a natural amino acid, a non-natural amino acid, a natural amino acid polypeptide or a non-natural amino acid polypeptide. Such changes, or modifications, may be obtained by post synthesis modifications of natural amino acids, non-natural amino acids, natural amino acid polypeptide or a non-natural amino acid polypeptide, or by co-translation, or by post-translational modifications of a natural amino acid, a non-natural amino acid, a natural amino acid polypeptide or a non-natural amino acid polypeptide.

"Molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. In one embodiment, the polyclonal antibody contains a plurality of monoclonal antibodies with different epitope specificities, affinities, or avidities within a single antigen that contains multiple antigenic epitopes. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by KOHLER et. al., Nature 256: 495 (1975), or may be made by recombinant DNA methods (see, e.g., U.S. Pat. No. 4,816,567). The "monoclonal antibodies" may also be isolated from phage antibody libraries using the techniques described in CLACKSON et. al., Nature 352: 624-628 (1991) and MARKS et. al., J. Mol. Biol. 222: 581-597 (1991), for example. These monoclonal antibodies will usually bind with at least a Kd of about 1 μM, more usually at least about 300 nM, typically at least about 30 nM, preferably at least about 10 nM, more preferably at least about 3 nM or better, usually determined by ELISA.

A "non-natural amino acid" or otherwise written as "nnAA" refers to an amino acid that is not one of the twenty (20) common amino acids or pyrolysine or selenocysteine. Other terms that may by used synonymously with the term nnAA is "non-natural encoded amino acid", "unnatural amino acid", "non-naturally occurring amino acid". Additionally, the term nnAA includes, but is not limited to, amino acids which do not occur naturally and may be obtained synthetically or may be obtained by modification of non-natural amino acids.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polypeptide" means a polymer of at least about 4, 5, 6, 7, or 8 amino acids. Throughout the specification, standard three letter (See, Table II) or single letter designations for amino acids are used. In the art, this term is often used interchangeably with "peptide" or "protein".

As used herein, the term "single-chain Fv" or "scFv" or "single chain" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see PLUCKTHUN, THE PHARMACOLOGY OF MONOCLONAL ANTIBODIES, vol. 113, Rosenburg and Moore eds. Springer-Verlag, New York, pp. 269-315 (1994).

As used herein, the terms "specific", "specifically binds" and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific. In one embodiment, a specific antibody is one that only binds the Her2, EGFR, Trop2, CDH3, antigen, but does not bind to the irrelevant antigen. In another embodiment, a specific antibody is one that binds human Her2, EGFR, Trop2, CDH3-4 antigen but does not bind a non-human Her2, EGFR, Trop2, CDH3 antigen with 70%, 75%, 80%, 85%, 90%, 91%, 92%, 93%, 94%, 95%, 96%, 97%, 98%, 99% or greater amino acid homology with the Her2, EGFR, Trop2, CDH3 antigen. In another embodiment, a specific antibody is one that binds human Her2, EGFR, Trop2, CDH3 antigen but does not bind a non-human Her2, EGFR, Trop2, CDH3 antigen with 70%, 75%, 80%, 85%, 90%, 91%, 92%, 93%, 94%, 95%, 96%, 97%, 98%, 99% or greater percent identity with the amino acid sequence of the Her2, EGFR, Trop2, CDH3 antigen. In another embodiment, a specific antibody is one that binds human Her2, EGFR, Trop2, CDH3 antigen and binds murine Her2, EGFR, Trop2, CDH3 antigen, but with a higher degree of binding the human antigen. In another embodiment, a specific antibody is one that binds human Her2, EGFR, Trop2, CDH3 antigen and binds primate Her2, EGFR, Trop2, CDH3 antigen, but with a higher degree of binding the human antigen. In another embodiment, the specific antibody binds to human Her2, EGFR, Trop2, CDH3 antigen and any non-human Her2, EGFR, Trop2, CDH3 antigen, but with a higher degree of binding the human antigen or any combination thereof.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "variant" refers to a molecule that exhibits a variation from a described type or norm, such as a protein that has one or more different amino acid residues in the corresponding position(s) of a specifically described protein (e.g. the Her2, EGFR, Trop2, CDH3 protein) An analog is an example of a variant protein. Splice isoforms and single nucleotides polymorphisms (SNPs) are further examples of variants.

II.) Antibodies

Another aspect of the invention provides antibodies that bind to Her2, EGFR, Trop2, CDH3, and other TAAs disclosed herein. In one embodiment, the antibody that binds to Her2, EGFR, Trop2, CDH3 and other TAA-related proteins.

As is known in the art, Her2, EGFR, Trop2, CDH3 and other TAA antibodies of the invention are particularly useful in cancer (see, e.g., Table I), for prognostic assays, imaging, diagnostic, and therapeutic methodologies. In one embodiment is a Her2, EGFR, Trop2, CDH3, and other TAA binding assay disclosed herein for use in detection of cancer, for example, in an immunoassay. Similarly, such antibodies are useful (e.g. when combined with a therapeutic agent, in an ADC, in the treatment, and/or prognosis of cancer (for example, the cancers set forth in Table I) to the extent Her2, EGFR, Trop2, CDH3, and/or other TAA are also expressed or overexpressed in these other cancers. Moreover, intracellularly expressed antibodies (e.g., single chain antibodies) are therapeutically useful in treating cancers in which the expression of Her2, EGFR, Trop2, CDH3, and other targets are involved.

Various methods for the preparation of antibodies, specifically monoclonal antibodies, are well known in the art. For example, antibodies can be prepared by immunizing a suitable mammalian host using a Her2, EGFR, Trop2, CDH3, and other TAA-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of Her2, EGFR, Trop2, CDH3, and other TAAs can also be used, such as a Her2, EGFR, Trop2, CDH3 GST-fusion protein. In a particular embodiment, a GST fusion protein comprising all or most of the amino acid sequence of Her2, EGFR, Trop2, CDH3 is produced, and then used as an immunogen to generate appropriate antibodies. In another embodiment, a Her2, EGFR, Trop2, CDH3, and other TAA-related protein is synthesized and used as an immunogen.

In addition, naked DNA immunization techniques known in the art are used (with or without purified Her2, EGFR, and other TAA-related protein or Her2, EGFR, Trop2, CDH3, and other TAA expressing cells) to generate an immune response to the encoded immunogen (for review, see DONNELLY et. al., 1997, Ann. Rev. Immunol. 15: 617-648).

Preferred methods for the generation of Her2, EGFR, Trop2, CDH3, and other TAA antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or another carrier protein. In some circumstances, direct conjugation using, for example, carbodiimide reagents are used; in other instances, linking reagents such as those supplied by Pierce Chemical Co., Rockford, Ill., are effective. Administration of a Her2, EGFR, Trop2, CDH3, and other TAA immunogen is often conducted by injection over a suitable time period and with use of a suitable adjuvant, as is understood in the art. During the immunization schedule, titers of antibodies can be taken to determine adequacy of antibody formation.

Her2, EGFR, Trop2, CDH3, and other TAA monoclonal antibodies can be produced by various means well known in the art. For example, immortalized cell lines that secrete a desired monoclonal antibody are prepared using the standard hybridoma technology of Kohler and Milstein or modifications that Immortalize antibody-producing B cells, as is generally known. Immortalized cell lines that secrete the desired antibodies are screened by immunoassay in which the antigen is a Her2, EGFR, Trop2, CDH3, and other TAA-related protein. When the appropriate immortalized cell culture is identified, the cells can be expanded, and antibodies produced either from in vitro cultures or from ascites fluid.

The antibodies or fragments of the invention can also be produced by recombinant means. Regions that bind specifically to the desired regions of a Her2, EGFR, Trop2, CDH3, and other TAA protein can also be produced in the context of chimeric or complementarity-determining region (CDR) grafted antibodies of multiple species origin. Humanized or human Her2, EGFR, Trop2, CDH3, and other TAA antibodies can also be produced and are preferred for use in therapeutic contexts. Methods for humanizing murine and other non-human antibodies, by substituting one or more of the non-human antibody CDRs for corresponding human antibody sequences, are well known (see for example, JONES et. al., 1986, Nature 321: 522-525; RIECHMANN et. al., 1988, Nature 332: 323-327; VERHOEYEN et. al., 1988, Science 239: 1534-1536). See also, CARTER et. al., 1993, Proc. Natl. Acad. Sci. USA 89: 4285 and SIMS et. al., 1993, J. Immunol. 151: 2296.

In one embodiment, human monoclonal antibodies of the invention can be prepared using VelocImmune mice into which genomic sequences bearing endogenous mouse variable segments at the immunoglobulin heavy chain (VH, DH, and JH segments) and/or kappa light chain (VK and JK) loci have been replaced, in whole or in part, with human genomic sequences bearing unrearranged germline variable segments of the human immunoglobulin heavy chain (VH, DH, and JH) and/or kappa light chain (VK and JK) loci (Regeneron, Tarrytown, N.Y.). See, for example, U.S. Pat. Nos. 6,586, 251, 6,596,541, 7,105,348, 6,528,313, 6,638,768, and 6,528, 314.

In addition, human antibodies of the invention can be generated using the HuMAb mouse (Medarex, Inc.) which contains human immunoglobulin gene miniloci that encode unrearranged human heavy (mu and gamma) and kappa light chain immunoglobulin sequences, together with targeted mutations that inactivate the endogenous mu and kappa chain loci (see e.g., LONBERG, et. al. (1994) Nature 368(6474): 856-859).

In another embodiment, fully human antibodies of the invention can be raised using a mouse that carries human immunoglobulin sequences on transgenes and transchromosomes, such as a mouse that carries a human heavy chain transgene and a human light chain transchromosome. Such mice, referred to herein as "KM mice", such mice are described in TOMIZUKA et. al. (2000) Proc. Natl. Acad. Sci. USA 97:722-727 and PCT Publication WO 02/43478 to TOMIZUKA, et. al.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to LADNER et. al.; U.S. Pat. Nos. 5,427,908 and 5,580,717 to DOWER et. al.; U.S. Pat. Nos. 5,969,108 and 6,172,197 to MCCAFFERTY et. al.; and U.S. Pat. Nos. 5,885,793; 6,521,404; 6,544,731; 6,555,313; 6,582,915 and 6,593,081 to GRIFFITHS et. al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to WILSON, et. al.

Additionally, human antibodies of the present invention can be made with techniques using transgenic mice, inactivated for antibody production, engineered with human heavy and light chains loci referred to as Xenomouse (Amgen Fremont, Inc., formerly Abgenix, Inc.). An exemplary description of preparing transgenic mice that produce human antibodies can be found in U.S. Pat. No. 6,657,103. See, also, U.S. Pat. Nos. 5,569,825; 5,625,126; 5,633,425; 5,661,016; and 5,545,806; and MENDEZ, et. al. Nature Genetics, 15: 146-156 (1998); KELLERMAN, S. A. & GREEN, L. L., Curr. Opin. Biotechnol 13, 593-597 (2002).

Any of the methods of production above result in antibodies that have a certain ability to bind Her2, EGFR, Trop2, CDH3, and other TAA, or homologs or fragments or polypeptide sequences having 85, 90, 91, 92, 93, 94, 95, 96, 9, 98, or 99% sequence identity to Her2, EGFR, Trop2, CDH3, and other TAAs.

The binding affinity ($K_D$) of the antibodies, binding fragments thereof, and antibody drug conjugates comprising the same for Her2, EGFR, Trop2, CDH3, and other TAAs may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 micromolar and 500 micromolar or between 500 micromolar and 1 nM.

The binding affinity of the antigen binding protein is determined by the association constant (Ka) and the dissociation constant (Kd) (KD=Kd/Ka). The binding affinity may be measured by BIACORE for example, by capture of the test antibody onto a protein-A coated sensor surface and flowing Her2, EGFR, Trop2, CDH3, and other TAAs over this surface. Alternatively, the binding affinity can be measured by FORTEBIO for example, with the test antibody receptor captured onto a protein-A coated needle and flowing Her2, EGFR, Trop2, CDH3, and other TAAs over this surface. One of skill in the art can identify other suitable assays known in the art to measure binding affinity.

Engineered antibodies of the invention include those in which modifications have been made to framework residues within $V_H$ and/or $V_L$ (e.g. to improve the properties of the antibody). Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis (e.g., "backmutated" from leucine to methionine). Such "backmutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by CARR, et. al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, a Her2, EGFR, Trop2, CDH3, and other TAAs MAb of the invention may be chemically modified (e.g., one or more chemical moieties can be attached to the antibody) or be modified to alter its glycosylation, again to alter one or more functional properties of the MAb. Each of these embodiments is described in further detail below. In one embodiment, the hinge region of CH1 is modified such that the number of cysteine residues in the hinge region is altered, e.g., increased or decreased. This approach is described further in U.S. Pat. No. 5,677,425 by BODMER, et. al. The number of cysteine residues in the hinge region of CH1 is altered to, for example, facilitate assembly of the light and heavy chains or to increase or decrease the stability of the Her2, EGFR, Trop2, CDH3, and other TAA MAb.

In another embodiment, the Fc hinge region of an antibody is mutated to decrease the biological half-life of the Her2, EGFR, Trop2, CDH3, and other TAA MAb. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by WARD, et. al.

In another embodiment, the Her2, EGFR, Trop2, CDH3, and other TAA MAb is modified to increase its biological half-life. Various approaches are possible. For example, mutations can be introduced as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by PRESTA et. al.

In yet other embodiments, the Fc region is altered by replacing at least one amino acid residue with a different amino acid residue to alter the effector function(s) of the Her2, EGFR, Trop2, CDH3, and other TAA MAb. For example, one or more amino acids selected from amino acid specific residues can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter, et al.

In a preferred embodiment, the Her2, EGFR, Trop2, CDH3, and other TAA Mab comprises a triple substitution at the following positions: L234A, L235A, L328C.

In a preferred embodiment, a Her2 Mab comprises a triple substitution at the following positions: L234A, L235A, L328C.

In a preferred embodiment, an EGFR Mab comprises a triple substitution at the following positions: L234A, L235A, L328C.

In a preferred embodiment, a Trop2 Mab comprises a triple substitution at the following positions: L234A, L235A, L328C.

In a preferred embodiment, a CDH3 Mab comprises a triple substitution at the following positions: L234A, L235A, L328C.

In another preferred embodiment, a TAA Mab comprises a triple substitution at the following positions: L234A, L235A, L328C.

In another embodiment, the Her2, EGFR, Trop2, CDH3, and other TAA Mab comprises a single substitution at the following positions: L328C.

In another embodiment, a Her2 Mab comprises a single substitution at the following positions: L328C.

In another embodiment, an EGFR Mab comprises a single substitution at the following positions: L328C.

In another embodiment, a Trop2 Mab comprises a single substitution at the following positions:

In another embodiment, a CDH3 Mab comprises a single substitution at the following positions: L328C.

In another embodiment, a TAA Mab of the disclosure comprises a single substitution at the following positions: L328C.

In another embodiment, the Her2, EGFR, Trop2, CDH3, and other TAA Mab comprises a double substitution at the following positions: L234A, L235A.

In another embodiment, a Her2 Mab comprises a double substitution at the following positions: L234A, L235A.

In another embodiment, an EGFR Mab comprises a double substitution at the following positions: L234A, L235A.

In another embodiment, a Trop2 Mab comprises a double substitution at the following positions: L234A, L235A.

In another embodiment, a CDH3 Mab comprises a double substitution at the following positions: L234A, L235A.

In another embodiment, a TAA Mab of the disclosure comprises a double substitution at the following positions: L234A, L235A.

Reactivity of the Her2, EGFR, Trop2, CDH3, and other TAA antibodies can be established by a number of well-known means, including Western blot, immunoprecipitation, ELISA, and FACS analyses using, as appropriate, Her2, EGFR, Trop2, CDH3, and other TAA-related proteins, Her2, EGFR, Trop2, CDH3, and other TAA-expressing cells or extracts thereof. A Her2, EGFR, Trop2, CDH3, and other TAA antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme.

III.) Fc Mutations to Modify Effector Function

The Fc region of an antibody (i.e., the terminal ends of the heavy chains of antibody spanning domains CH2, CH3 and a portion of the hinge region) is limited in variability and is involved in effecting the physiological roles played by the antibody. The effector functions attributable to the Fc region of an antibody vary with the class and subclass of antibody and include binding of the antibody via the Fc region to a specific Fc receptor ("FcR") on a cell which triggers various biological responses.

These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (See, RAVETCH, et al., Annu. Rev. Immunol. 19 (2001) 275-290). The cell-mediated reaction wherein non-specific cytotoxic cells that express FcγRs recognize bound antibody on a target cell and subsequently cause phagocytosis of the target cell is referred to as antibody dependent cell-mediated phagocytosis (ADCP). In addition, an overlapping site on the Fc region of the molecule also controls the activation of a cell independent cytotoxic function mediated by complement, otherwise known as complement dependent cytotoxicity (CDC).

Additionally, the complement inflammatory cascade is a part of the innate immune response and is crucial to the ability for an individual to ward off infection. Another important Fc ligand is the complement protein C1q. Fc binding to C1q mediates a process called complement dependent cytotoxicity (CDC). C1q is capable of binding six antibodies, although binding to two IgGs is sufficient to activate the complement cascade. C1q forms a complex with the C1r and C1s serine proteases to form the C1 complex of the complement pathway.

In many circumstances, the binding and stimulation of effector functions mediated by the Fc region of immunoglobulins is highly beneficial. However, in certain instances it may be more advantageous to decrease or even to eliminate the effector function. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (See, HUTCHINS, et al., PNAS USA 92 (1995) 11980-11984. In these cases, the use of antibodies that poorly recruit complement or effector cells would be of a tremendous benefit (See also, U.S. Pat. Nos. 6,194,551; 5,885,573 and PCT publication WO 04/029207).

In other instances, for example, where blocking the interaction of a widely expressed receptor with its cognate ligand is the objective, it would be advantageous to decrease or eliminate all antibody effector function to reduce unwanted toxicity. Additionally, in the instance where a therapeutic antibody exhibited promiscuous binding across a number of human tissues it would be prudent to limit the targeting of effector function to a diverse set of tissues to limit toxicity. Lastly, reduced affinity of antibodies to the FcγRII receptor in particular would be advantageous for antibodies inducing platelet activation and aggregation via FcγRII receptor binding, which would be a serious side-effect of such antibodies. See, T A M, et. al., Antibodies 6:12 (2017). See, also WEBER et. al., Pharm Res 35:169 (2018).

Although there are certain subclasses of human immunoglobulins that lack specific effector functions, there are no known naturally occurring immunoglobulins that lack all effector functions. An alternate approach would be to engineer or mutate the critical residues in the Fc region that are responsible for effector function. See, SCHLOTHAUER, et. al., Protein Eng. Design, and Selection, vol. 29, no. 10 pp 457-466 (2016) & WANG, et. al, Protein Cell, 9(1) pp 63-73 (2018). Indeed, several researching entities have attempted such endeavors. See, for example, PCT publications WO 2009/100309 (Medimmune), WO 2006/076594 (Xencor), WO 1999/58572 (Univ. Cambridge), US 2006/0134709 (Macrogenics), WO 2006/047350 (Xencor), WO 2006/053301 (Xencor), U.S. Pat. No. 6,737,056 (Genentech), U.S. Pat. No. 5,624,821 (Scotgen Pharmaceuticals), US 2010/0166740 (Roche), and U.S. Pat. No. 8,969,526 (Roche Glycart AG).

The binding of IgG to activating and inhibitory Fcγ receptors or the first component of complement (C1q) depends on residues located in the hinge region and the CH2 domain. Two regions of the CH2 domain are critical for FcγRs and complement C1q binding and have unique sequences. Substitution of human IgG1 and IgG2 residues at positions 233-236 and IgG4 residues at positions 327, 330 and 331 have greatly reduced ADCC and CDC (See, ARMOUR, et al., Eur. J. Immunol. 29(8) (1999) 2613-2624; SHIELDS, et al., J. Biol. Chem. 276(9) (2001) 6591-6604).

In addition, IDUSOGIE, et al., J. Immunol. 166 (2000) 2571-2575, mapped the C1q binding site for RITUXAN and showed that Pro329Ala reduced the ability of Rituximab to bind C1q and activate complement. In addition, substitution of Pro329 with Ala has been reported to lead to a reduced binding to the FcγRI, FcγRII and FcγRIIIA receptors (See, SHIELDS, et al., J. Biol. Chem. 276(9) (2001) 6591-6604). However, this mutation has also been described as exhibiting a wildtype-like binding to the FcγRI and FcγRII and only a very small decrease in binding to the FcγRIIIA receptor (See, EP 1,068,241, Genentech).

Additionally, OGANESYAN, et al., Acta Cristallographica D64 (2008) 700-704 introduced the triple mutation L234F/L235E/P331S into the lower hinge and C2H domain and showed a decrease in binding activity to human IgG1 molecules to human C1q receptor, FcγRI, FcγRII and FcγRIIIA.

Against the foregoing backdrop, the invention herein relates to a method for making a polypeptide comprising a Fc variant wherein the Fc is silenced and/or inhibited. The "parent", "starting", "nonvariant" or "wildtype" polypeptide is prepared using techniques available in the art for generating polypeptides or antibodies comprising an Fc region. In the preferred embodiment of the invention, the parent polypeptide is an antibody and exemplary methods for generating antibodies are described in more detail in the disclosure. In a further preferred embodiment, the wildtype polypeptide is an antibody which binds Her2, EGFR, Trop2, CDH3, and/or any TAA of the disclosure (See, Table IV).

One embodiment of the invention encompasses polypeptides comprising an Fc region of an antibody, comprising the addition, substitution, or deletion of at least one amino acid residue to the Fc region resulting in reduced or ablated affinity for at least one Fc receptor. The Fc region interacts with a number of receptors or ligands including but not limited to Fc Receptors (e.g., FcγRI, FcγRIIA, FcγRIIIA), the complement protein C1q, and other molecules such as proteins A and G. As noted in the disclosure, these interactions are essential for a variety of effector functions and downstream signaling events including, but not limited to, antibody dependent cell-mediated cytotoxicity (ADCC), Antibody-dependent cellular phagocytosis (ADCP) and complement dependent cytotoxicity (CDC).

Accordingly, in certain embodiments the variants of the invention have reduced or ablated affinity for an Fc receptor responsible for an effector function compared to a polypeptide having the same amino acid sequence as the polypeptide comprising a Fc variant of the invention but not comprising the addition, substitution, or deletion of at least one amino acid residue to the Fc region (also referred to herein as an "wildtype polypeptide"). In certain embodiments, polypeptide comprising a Fc variant of the invention comprise at least one or more of the following properties: reduced or ablated effector (ADCC and/or CDC and/or ADCP) function, reduced or ablated binding to Fc receptors, reduced or ablated binding to C1q or reduced or ablated toxicities. More specifically, embodiments of the invention provide anti-Her2, anti-EGFR, anti-Trop2, anti-CDH3, and anti-TAA (tumor associated antigens (Table IV)) antibodies with reduced affinity for Fcγ receptors (e.g. FcγRI, FcγRIIA, FcγRIIB, FcγRIIIA, FcγRIIIB) and/or the complement protein C1q.

In one embodiment, the invention comprises Her2, EGFR, Trop2, CDH3, and TAA MAbs comprising a triple mutation.

In one embodiment, antibodies of the invention comprise an Fc region comprising at least one addition, substitution, or deletion of an amino acid residue at position 328, wherein the numbering system of the constant region is that of the EU index as set forth in KABAT, et. al., NIH Publication 91 (1991) 3242, National Technical Information Service, Springfield, Va.

In one embodiment, antibodies of the invention comprise an Fc region comprising at least one addition, substitution, or deletion of an amino acid residue at position 234, wherein the numbering system of the constant region is that of the EU index as set forth in KABAT, et. al., NIH Publication 91 (1991) 3242, National Technical Information Service, Springfield, Va.

In one embodiment, antibodies of the invention comprise an Fc region comprising at least one addition, substitution, or deletion of an amino acid residue at position 235, wherein the numbering system of the constant region is that of the EU index as set forth in KABAT, et. al., NIH Publication 91 (1991) 3242, National Technical Information Service, Springfield, Va.

In a certain aspect of the invention the polypeptide comprising a Fc variant comprises an antibody. In still another aspect of the invention the polypeptide comprising a Fc variant comprises a human IgG1, IgG2, IgG3, or IgG4 Fc region. In still a further aspect of the invention the variants are IgG1, IgG2, IgG3, or IgG4 antibodies.

In a further specific embodiment, the above-mentioned polypeptides comprise a human IgG1 region.

In a specific embodiment, polypeptides of the invention comprise an Fc variant of a wild-type human Fc polypeptide said variant comprising an amino acid substitution at position L328C, where the numbering of the residues in the IgG Fc region is that of the EU index as in Kabat. In still another embodiment, said variant comprises at least one further amino acid substitution. In still another embodiment, said variant comprises at least one further amino acid substitution. In still another embodiment, said variant comprises three (3) amino acid substitution(s) at L234A, L235A, and L328C.

In a specific embodiment, an anti-Her2 MAb of the invention comprises an Fc variant of a wild-type human Fc Her2 Mab comprising three (3) amino acid substitutions at L234A, L235A, and L328C.

In a specific embodiment, an anti-EGFR MAb of the invention comprises an Fc variant of a wild-type human Fc EGFR Mab comprising three (3) amino acid substitutions at L234A, L235A, and L328C.

In a specific embodiment, an anti-Trop2 MAb of the invention comprises an Fc variant of a wild-type human Fc Trop2 Mab comprising three (3) amino acid substitutions at L234A, L235A, and L328C.

In a specific embodiment, an anti-CDH3 MAb of the invention comprises an Fc variant of a wild-type human Fc CDH3 Mab comprising three (3) amino acid substitutions at L234A, L235A, and L328C.

In a specific embodiment, a TAA MAb of the invention comprises an Fc variant of a wild-type human Fc TAA Mab comprising three (3) amino acid substitutions at L234A, L235A, and L328C.

In one aspect polypeptides comprising an Fc variant do not affect target binding as compared to an unmodified antibody.

In one aspect polypeptides comprising an Fc variant of the invention exhibit inhibition of FcγRI binding as compared to an unmodified antibody.

In one aspect polypeptides comprising an Fc variant of the invention exhibit inhibition of FcγRII binding as compared to an unmodified antibody.

In one aspect polypeptides comprising an Fc variant of the invention exhibit inhibition of FcγRIIIa binding as compared to an unmodified antibody.

In one aspect polypeptides comprising an Fc variant of the invention do not substantially affect FcRn binding as compared to an unmodified antibody.

As one of ordinary skill in the art will appreciate and a surprising realization discovered by this invention found that the need of a triple mutation and specifically the addition of an amino acid substitution(s) at L234A, and L235A was due to the following observation(s). First, L328C by itself exhibit(s) only partial reduction of Fc effector function. A greater extent of Fc silencing can be achieved by combining additional mutations. L234 and L235 were selected as these residues are located close to the hinge area and can partially reduce FcγR binding when mutated to alanine. A combination of L234A and L235A with L328C exhibited a near complete inhibition of FcγR interaction for all isoforms tested.

As observed, despite complete abrogation of FcγR binding, the triple mutation (L328C in combination with L234A/L235A) did not affect target antigen binding, as comparable binding activity was observed when compared to the wild-type counterpart. Antibody stability and expression also remained comparable to the wild-type antibodies. Thus, the triple mutation allows a complete inhibition of Fc effector function without compromising target specificity, antibody quality, and yield.

In addition, as discussed, infra, the specific triple mutation, can facilitate efficient site-specific conjugation.

IV.) Antibody Drug Conjugates

In another aspect, the invention provides antibody-drug conjugates (ADCs), comprising an antibody conjugated to a therapeutic agent. The therapeutic agent maybe a cytotoxic agent, a cytostatic agent, a chemotherapeutic agent, a drug, a growth inhibitory agent, a toxin (e.g., an enzymatically active toxin of bacterial, fungal, plant, or animal origin, or fragments thereof), or a radioactive isotope (i.e., a radio-conjugate). In another aspect, the invention further provides methods of using the ADCs. In one aspect, an ADC comprises any of the above Her2, EGFR, Trop2, CDH3, and other TAA MAbs covalently attached or attached via oxime bond to a cytotoxic agent or a detectable agent.

In a further embodiment, an ADC comprises a Her2, EGFR, Trop2, CDH3, and other TAA Mab further comprising a triple substitution at the following positions: L234A, L235A, L328C.

In a preferred embodiment, an ADC comprises a Her2, EGFR, Trop2, CDH3, and other TAA Mab further comprising a triple substitution at the following positions: L234A, L235A, L328C and further comprising a site-specific conjugation at L328C.

By way of background, the use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; NICULESCU-DUVAZ and SPRINGER (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (BALDWIN et. al., (1986) Lancet pp. (Mar. 15, 1986):603-05; Thorpe, (1985) "Antibody Carriers of Cytotoxic Agents in Cancer Therapy: A Review," in Monoclonal Antibodies '84: Biological and Clinical Applications, A. PINCHERA et. al. (ed.), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (ROWLAND et. al., (1986) supra). Toxins used in antibody-toxin conjugates include bacterial toxins such as diphtheria toxin, plant toxins such as ricin, small molecule toxins such as geldanamycin (MANDLER et. al. (2000) Jour. of the Nat. Cancer Inst. 92(19):1573-1581; MANDLER et. al. (2000) Bioorganic & Med. Chem. Letters 10:1025-1028; MANDLER et. al. (2002) Bioconjugate Chem. 13:786-791), maytansinoids (EP 1391213; LIU et. al., (1996) Proc. Natl. Acad. Sci. USA 93:8618-8623), and calicheamicin (LODE et. al. (1998) Cancer Res. 58:2928; HINMAN et. al. (1993) Cancer Res. 53:3336-3342). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Examples of antibody drug conjugates are, ADCETRIS (brentuximab vedotin, Seattle Genetics,), ZEVALIN® (ibritumomab tiuxetan, Biogen/Idec), MYLOTARG™ (gemtuzumab ozogamicin, Wyeth Pharmaceuticals), KADCYLA® (ado-trastuzumab emtansine, Genentech), BESPONSA® (inotuzumab ozogamicin, Pfizer/Wyeth), POLIVY (polatuzumab vedotin, Genentech/Roche), Cantuzumab mertansine (Immunogen, Inc.), and MLN-2704 (Millennium Pharm., BZL Biologics, Immunogen Inc.).

Further, therapeutic agents including but not limited to chemotherapeutic agents useful in the generation of ADCs are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radio-conjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987) Science, 238:1098. Carbon-14-labeled 1-isothiocyanatobenzyl-3-methyldiethylene triaminepentaacetic acid (MX-DTPA) is an exemplary chelating agent for conjugation of radionucleotide to the antibody (WO94/11026). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 (published Oct. 28, 1993).

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radio-conjugated antibodies. Examples include $At^{211}$, $I^{131}$, $I^{125}$, $Y^{90}$, $Re^{186}$, $Re^{88}$, $Sm^{53}$, $Bi^{212}$, $P^{32}$, $Pb^{212}$ and radioactive isotopes of Lu. When the conjugate is used for detection, it may comprise a radioactive atom for scintigraphic studies, for example $tC^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tC^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (FRAKER et. al. (1978) Biochem. Biophys. Res. Commun. 80: 49-57 can be used to incorporate iodine-123. "Monoclonal Antibodies in Immunoscintigraphy" (CHATAL, CRC Press 1989) describes other methods in detail.

The present invention provides, inter alia, antibody-drug conjugate compounds for targeted delivery of therapeutic agents. The inventors have made the discovery that the antibody-drug conjugate compounds have potent cytotoxic and/or cytostatic activity against cells expressing Her2, EGFR, Trop2, CDH3, and other TAAs.

The antibody-drug conjugate compounds comprise an Antibody unit covalently linked to at least one Drug unit. The Drug units can be covalently linked directly to the Antibody unit or via a Linker unit (-LU-). Additionally, the drug unit is conjugated at a site-specific location at L328C.

In some embodiments, the antibody drug conjugate compound has the following formula:

$$L\text{-}(LU\text{-}D)_p \qquad (I)$$

or a pharmaceutically acceptable salt or solvate thereof; wherein:
 L is the Antibody unit, e.g., a Her2, EGFR, Trop2, CDH3, or another TAA MAb of the present invention; and wherein the MAb comprises a triple mutation at the following locations: L234A, L235A, and L328C;
 (LU-D) is a Linker Unit-Drug unit moiety, wherein:
 LU- is a Linker unit, and
 -D is a drug unit having cytostatic or cytotoxic activity against a target cell; and
 p ranges from 1 to 20 or alternatively 1-50.
Additionally, the Drug unit moiety is conjugated at a site-specific location on the MAb at L328C.

In some embodiments, the antibody drug conjugate compound has the following formula:

$$L\text{-}(A_a\text{-}W_w\text{-}Y_y D)_p \qquad (II)$$

or a pharmaceutically acceptable salt or solvate thereof, wherein:
 L is the Antibody unit, e.g., Her2, EGFR, Trop2, CDH3, or another TAA MAb and wherein the MAb comprises a triple mutation at the following locations: L234A, L235A, and L328C; and
 -$A_a$-$W_w$-$Y_y$- is a Linker unit (LU), wherein:
 -A- is a Stretcher unit,
 a is 0 or 1 or 2 or 3,
 each -W- is independently an Amino Acid unit,
 w is an integer ranging from 0 to 12,
 -Y- is a self-immolative spacer unit,
 y is 0, 1 or 2;
 -D is a drug unit having cytostatic or cytotoxic activity against the target cell; and
 p is an integer from 1 to 20 or alternatively 1-50.
Additionally, the Drug unit moiety is conjugated at a site-specific location on the MAb at L328C.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined. In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is from 2 to 8.

The generation of Antibody-drug conjugate compounds can be accomplished by any technique known to the skilled artisan. Briefly, the Antibody-drug conjugate compounds comprise Her2, EGFR, Trop2, CDH3, or another TAA MAb and wherein the MAb comprises a triple mutation at the following locations: L234A, L235A, and L328C as the Antibody unit, a drug, and optionally a linker that joins the drug and the binding agent. In a preferred embodiment, the drug unit is conjugated at a site-specific location at L328C.

A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the Her2, EGFR, Trop2, CDH3, or other TAA MAb under appropriate conditions.

V.) Site-Specific Conjugation Formats for ADCs

As one of ordinary skill in the art will appreciate, the ability to optimize payload placement and conjugate composition in the context of an ADC is an advantageous endeavor. See, ABHIJIIT, et al., Bioprocess Int., Mab Upstream Processing (October 2014).

Generally speaking, bio-conjugation strategies involve covalently linking a protein or peptide (biologic) with a small molecule, carbohydrate, oligonucleotide, synthetic polymer, or another protein/peptide. This approach can be crucial to create differentiation and drive product development in the highly competitive biologics market. These strategies were fundamental to development of highly successful conjugate vaccines such as Prevnar 13, Menactra, Menomune, and HibTITER. Those four (4) were created by conjugating bacterial polysaccharides to immunogenic carrier proteins. Similarly, bioconjugation to half-life-extending polymeric carriers such as polyethylene glycol (PEG) is applied to create current commercial drugs—e.g., certozilumab (Cimzia), pegfilgrastim (Neulasta), and pegvisomant (Somavert)—that have longer duration of action than their unconjugated counterparts and dosing regimens that facilitate patient compliance.

As is known in the art, the choice of linkers and conjugation chemistry for making first-generation ADCs was dictated by limitations of working with proteins. Thus, linkers were functionalized with reactive groups designed to specifically react with surface-accessible nucleophilic amino-acid side chains belonging to native amino acids such as cysteine (thiol) or lysine (amine).

However, treatment of an antibody with reducing agents such as dithiothreitol (DTT) or tris(2-carboxyethyl) phosphine (TCEP) can break those disulfide bonds and expose free thiols, which then can be readily conjugated with maleimide-containing linkers. Up to four interchain disulfide bonds can be reduced, thereby exposing up to eight reactive thiol groups for conjugation. Conditions developed for thiol chemical conjugation lead to either complete or partial reduction of disulfide bonds, and conjugates made using this method can contain either zero, two, four, six, or eight drugs per antibody molecule.

It is important to note that beyond the number of drugs per antibody molecule, another level of heterogeneity comes from the site of conjugation. Thus, an ADC with a specific drug-to-antibody ratio (DAR) generated by cysteine conjugation is still a heterogeneous mixture of conjugates with different sites of conjugation. However, it is fair to say that because only eight sites are available for cysteine conjugation (compared with up to 80 available for lysine-directed chemistries), the cysteine conjugation approach provides greater control over the site of conjugation, facilitating better characterization. The controlled reduction-alkylation strategy has been used successfully for making the approved ADCETRIS (Seattle Genetics, Bothell, Wash.) product along with a number of other ADCs currently undergoing clinical trials.

Researchers have studied the in vivo effects of ADCs targeting CD30+ tumor cells—with two, four, and eight monomethyl auristatin E (MMAE) toxins per antibody molecule—and demonstrated that the stoichiometry of drug loading significantly influenced the drug's pharmacokinetics (PKs), efficacy, and toxicity. HAMBLETT et. al. found that in their system, ADCs with four drugs per antibody were more potent than those with two but had comparable efficacy and better tolerability than those with eight drugs/antibody. The results indicated that, in general, ADCs with higher drug loadings have greater clearance, more efficacy, and increased toxicity. That implied that each ADC would have an optimal drug loading with the right balance of efficacy and toxicity.

That seminal work established the concept that the DAR is a key design parameter for ADCs. It became apparent that chemical conjugations to native cysteine or lysine residues would be suboptimal because they produce heterogeneous ADC mixtures. Heterogeneity comes from differences in DAR and conjugation sites, resulting in ADC subpopulations that may be less potent, more toxic, and have differing disposition and PK properties. In addition, analytical characterization and controlling batch-to-batch variability during manufacturing remains a significant challenge with such nonselective conjugation methods. To overcome those limitations, the concept of site-specific conjugations has evolved, initially with a goal of producing homogeneous ADCs and controlling DAR and sites of conjugation.

Several site-specific conjugation technologies were borne out optimizing payload placement using a variety of techniques (See, for example, ThioMab (Genentech), Seattle Genetics, and Ambrx, Inc.).

The reported work on ThioMab revealed another fundamental concept: Not only is ADC homogeneity key to improved biophysical and therapeutic properties, but the actual site of conjugation on the antibody backbone also has a major influence on in vivo behavior of an ADC molecule. SHEN, et. al., made multiple homogeneous TDC conjugates with a HER2-targeting antibody using a MMAE payload, wherein the engineered cysteine for conjugation was located in either the light chain (LC), heavy chain (HC), or Fc region of the antibody. All conjugates demonstrated comparable in vitro potencies, but the authors report significant differences in their in vivo efficacy and PK properties.

The LC conjugate demonstrated the greatest efficacy when studied in a mouse xenograft model, in which the HC conjugate had moderate and the Fc conjugate had little to no activity. A mouse PK study revealed a similar trend with the LC conjugate demonstrating the greatest stability and lowest clearance followed by the HC conjugate, and the Fc-conjugated ADC was cleared fastest and provided the lowest ADC exposure. These results were attributed to differences in the local microenvironment and solvent accessibility contributing to differential stability of the linker system at different sites.

Several additional site-specific bioconjugation methods have been reported with the goal of delivering homogeneous ADCs relative to the first-generation lysine and cysteine conjugations, but only a subset of these technologies offer greater versatility in finding the optimal conjugation site for a given antibody-payload combination. Those include, conjugation by nonnatural amino acids (nnAAs) introduced by genetic-code modification (Ambrx, LaJolla, Calif.; Sutro Biopharma, South San Francisco, Calif.; Allozyne, acquired by Medimmune, Seattle, Wash.). Also, transglutaminase (TG) mediated conjugations to engineered glutamine tags (Pfizer, New York, N.Y.). Also, conjugations with aldehydr-tagged antibodies generated by coexpressed formylglycine-generating enzyme (FGE) (Redwood Bioscience, acquired by Catalent Pharma Solutions, Emeryville, Calif.).

Based on the foregoing, studies with technologies that offer the option of flexible site-specific conjugation have firmly established that the site of conjugation significantly influences the pharmacological properties of an ADC. Thus, it should be considered as a critical parameter in product design and the ability to find an optimal site for a particular payload-antibody combination can be critical to the success of the development of the product or product(s). See, SCHUMACHER, et. al., J. Clin. Immunol, 36 (Suppl 1):S100-S107 (2016); DEONARAIN, et. al., Expert Opin. Drug Discov, 10(5) (2015); ZHOU, Biomedicines, 5:64 (2017); PANOWSKI, et. al., mAbs 6:1 pp 34-45 (January/February 2014); PCT Patent publication WO2018/20081, and United States Patent Publication No.: 2017/0080103.

In one embodiment, the site-specific conjugation approach via the conversion of Leu-328 to Cys in the Fc domain of a monoclonal antibody allows controlled conjugation without affecting target binding. Moreover, it is shown that neither the expression level nor the stability of the antibody is compromised by the introduction of L328C.

In a further embodiment, the site-specific conjugation approach via the conversion of Leu-328 to Cys in the Fc domain of a Her2 antibody allows controlled conjugation without affecting target binding. Moreover, it is shown that neither the expression level nor the stability of the antibody is compromised by the introduction of L328C.

In a further embodiment, the site-specific conjugation approach via the conversion of Leu-328 to Cys in the Fc domain of an EGFR antibody allows controlled conjugation without affecting target binding. Moreover, it is shown that neither the expression level nor the stability of the antibody is compromised by the introduction of L328C.

In a further embodiment, the site-specific conjugation approach via the conversion of Leu-328 to Cys in the Fc domain of an Trop2 antibody allows controlled conjugation without affecting target binding. Moreover, it can be shown that neither the expression level nor the stability of the antibody is compromised by the introduction of L328C.

In a further embodiment, the site-specific conjugation approach via the conversion of Leu-328 to Cys in the Fc domain of an CDH3 antibody allows controlled conjugation without affecting target binding. Moreover, it is shown that neither the expression level nor the stability of the antibody is compromised by the introduction of L328C.

In a further embodiment, the site-specific conjugation approach via the conversion of Leu-328 to Cys in the Fc domain of a TAA antibody (such as a TAA set forth in Table IV) allows controlled conjugation without affecting target binding. Moreover, it is shown that neither the expression level nor the stability of the antibody is compromised by the introduction of L328C.

The site-specific conjugation approach mediated by L328C was chosen to allow more homogeneous drug product and improved conjugation efficiency. Various therapeutic modalities including antibody drug conjugates (ADCs) can benefit from site-specific conjugation as it can prevent formation of heterogeneous mixture, which can have negative effect on in vivo efficacy and therapeutic index. Similarly, attachment of boron-containing entities to specifically defined sites of antibody molecules could improve efficacy of Boron Neutron Capture Therapy (BNCT), a noninvasive therapeutic modality for treating cancer.

The conversion of Leu-328 to Cys in the Fc domain of monoclonal antibody allows controlled conjugation without affecting target binding. Moreover, neither the expression level nor the stability of antibody is compromised by introduction of L328C. Quality assessment via size-exclusion chromatography shows >99% main peak, comparable to the wild-type counterpart. Thus, aggregation propensity often associated with introduction of unpaired cysteine is not observed for L328C. The uniform product formation with 100% conjugation efficiency mediated by L328C implicates simpler manufacturing process as compared to complicated and inefficient production process required for non-specifically conjugated counterparts. Defined and homogeneous composition mediated through L328C conjugation, with much reduced therapeutic liabilities and simpler manufacturing process, enable accelerated discovery and development of ADCs and antibody boron conjugates for the application of BNCT.

Additionally, L328C also exhibits added benefit of reducing Fc effector function. Safety liabilities associated with infusion reactions triggered by therapeutic monoclonal antibodies and their interaction with FcγRs have been reported. The ability to partially silence Fc effector function without compromise in antibody stability is an attractive feature of L328C. Potential mitigation strategies for improved clinical safety profile can be further developed for L328C-mediated conjugation or as a naked antibody, with possible combination with other variance previously shown to reduce Fc effector function.

VI.) Linker Units

Typically, the antibody-drug conjugate compounds comprise a Linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable, and the drug is released, for example, by antibody degradation.

In a preferred embodiment, the linker is conjugated at a site-specific position L328C.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. The linker can also be cleaved by a cleaving agent that is present in the extracellular environment (e.g. in the vicinity to the cellular membrane or tissue space). The linker can be, e.g., a peptidyl linker that is cleaved by an extracellular peptidase or protease enzyme, including, but not limited to, a cathepsin family enzymes or matrix metalloproteinases).

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., an oxime, hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; DUBOWCHIK AND WALKER, 1999, Pharm. Therapeutics 83:67-123; NEVILLE et. al., 1989, Biol. Chem. 264:14653-14661.)

In yet other embodiments, the linker is cleavable under reducing conditions known in the art. (See, e.g., Thorpe et al., 1987, Cancer Res. 47:5924-5931; WAWRZYNCZAK et. al., In *Immunoconjugates: Antibody Conjugates in Radioimagery and Therapy of Cancer* (C. W. VOGEL ed., Oxford U. Press, 1987. See also U.S. Pat. No. 4,880,935.). The linker can also be cleaved under reducing conditions found intra-cellularly (or extra-cellularly). For example, in a preferred embodiment, the specific linker N—O bond may be formally reduced and broken to result in a cleavage of the linker.

In yet other embodiments, the linker unit is not cleavable, and the drug is released by antibody degradation. (See PCT Publication No. WO2012/166560 (Ambrx, Inc.) incorporated by reference herein in its entirety and for all purposes).

In other, non-mutually exclusive embodiments, the linker promotes cellular internalization as known in the art.

A variety of exemplary linkers that can be used with the present compositions and methods are described in WO 2004/010957, U.S. Publication No. 2006/0074008, U.S. Publication No. 20050238649, and U.S. Publication No. 2006/0024317 (each of which is incorporated by reference herein in its entirety and for all purposes).

VII.) The Stretcher Unit

The Stretcher unit (A), when present, is capable of linking an Antibody unit to an Amino Acid unit (-W-), if present, to a Spacer unit (-Y-), if present; or to a Drug unit (-D). Useful functional groups that can be present on a Her2, EGFR, Trop2, CDH3, or other TAA MAb, either naturally or via chemical manipulation include, but are not limited to, keto, aldehyde, sulfhydryl, amino, hydroxyl, the anomeric hydroxyl group of a carbohydrate, and carboxyl. Suitable functional groups are keto, aldehyde, sulfhydryl, and amino. In one example, the keto group is on a non-natural amino acid (nnAA) incorporated into the Mab of the invention. In a further example, the aldehyde group is on a nnAA incorporated into the Mab of the invention. In another example, sulfhydryl groups can be generated by reduction of the intramolecular disulfide bonds of a Her2, EGFR, Trop2, CDH3, or other TAA MAb. In another embodiment, sulfhydryl groups can be generated by reaction of an amino group of a lysine moiety of a Her2, EGFR, Trop2, CDH3, or other TAA MAb with 2-iminothiolane (Traut's reagent) or other sulfhydryl generating reagents. In certain embodiments, the Her2, EGFR, Trop2, CDH3, or other TAA MAb is a recombinant antibody and is engineered to carry one or more lysines. In certain other embodiments, the recombinant Her2, EGFR, Trop2, CDH3, or other TAA MAb is engineered to carry additional sulfhydryl groups, e.g., additional cysteines.

In a preferred embodiment, a Her2, EGFR, Trop2, CDH3, or other TAA MAb comprises Fc modifications at L234A, L235A and further comprises another modification at L328C and further comprises a site-specific conjugation at L328C.

In a preferred embodiment, the Stretcher Unit is located at L328C.

VIII.) The Amino Acid Unit

The Amino Acid unit (-W-), when present, links the Stretcher unit to the Spacer unit if the Spacer unit is present, links the Stretcher unit to the Drug moiety if the Spacer unit is absent, and links the Antibody unit to the Drug unit if the Stretcher unit and Spacer unit are absent.

In certain embodiments, the Amino Acid unit can comprise natural amino acids. In other embodiments, the Amino Acid unit can comprise non-natural amino acids.

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In a preferred embodiment, the Amino Acid Unit is located at L328C.

IX.) The Spacer Unit

The Spacer unit (-Y-), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent. Spacer units are of two general types: non self-immolative or self-immolative. Examples of possible spacers of the invention are known in the art. See, TOKI et. al., 2002, J. Org. Chem. 67:1866-1872 and Nature Biotechnology 21(7):778-784).

Other examples of self-immolative spacers include, but are not limited to, aromatic compounds that are electronically similar to the PAB group such as 2-aminoimidazol-5-methanol derivatives (HAY et. al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (RODRIGUES et. al., 1995, Chemistry Biology 2:223), appropriately substituted bicyclo [2.2.1] and bicyclo[2.2.2] ring systems (STORM et. al., 1972, J. Amer. Chem. Soc. 94:5815) and 2-aminophenylpropionic acid amides (AMSBERRY et. al., 1990, J. Org. Chem. 55:5867). Elimination of amine-containing drugs that are substituted at the a-position of glycine (KINGSBURY et. al., 1984, J. Med. Chem. 27:1447) are also examples of self-immolative spacers.

In a preferred embodiment, the Amino Acid Unit is located at L328C.

X.) The Drug Unit

The Drug Unit (D) can be any therapeutic agent. For example, the Drug Unit may be a moiety that is cytotoxic, cytostatic or immunomodulatory (e.g., immunosuppressive) or chemotherapeutic agent. D is a Drug unit (moiety) having an atom that can form a bond with the Spacer unit (if present), with the Amino Acid unit (if present), with the Stretcher unit (if present) or with the Antibody unit. In some embodiments, the Drug unit D has a nitrogen atom that can form a bond with the Spacer unit (if used). As used herein, the terms "Drug unit" and "Drug moiety" are synonymous and used interchangeably.

XI.) Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an ADC can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an ADC exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the ADC.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an ADC is useful in the treatment of cancers.

Cell viability can be measured by determining in a cell the uptake of a dye such as neutral red, trypan blue, or ALAMAR™ blue (see, e.g., PAGE et. al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (SKEHAN et. al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., MOSMANN, 1983, J. Immunol. Methods 65:55-63).

Apoptosis can be quantitated by measuring, for example, DNA fragmentation.

Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (COLIGAN et. al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., PIAZZA et. al., 1995, *Cancer Research* 55:3110-16).

In vivo, the effect of a Her2, EGFR, Trop2, CDH3, or other TAA MAb therapeutic composition can be evaluated in a suitable animal model. For example, xenogeneic cancer models can be used, wherein cancer explants or passaged xenograft tissues are introduced into immune compromised animals, such as nude or SCID mice (KLEIN et. al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (See, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intra-organ, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

In one embodiment, the pharmaceutical composition of the present invention may comprise more than one species of ADC of the invention due to modification of a Her2, EGFR, Trop2, CDH3, or other TAA MAb. For example, the present invention includes a pharmaceutical composition comprising the ADC of the invention, wherein the Her2, EGFR, Trop2, CDH3, or other TAA MAb is an antibody with a C-terminal lysine partially removed or completely removed an antibody having N-terminal post-translational modification, an antibody lacking heavy chain C-terminal lysine and having N-terminal post-translational modification, and/or an antibody having heavy chain C-terminal lysine and not having N-terminal post-translational modification.

In a preferred embodiment, Her2, EGFR, Trop2, CDH3, or other TAA MAb is a triple mutation at L234A, L235A, and L328C, wherein L328C is a location for site-specific conjugation.

XII.) Treatment of Cancer(s) Expressing Her2, EGFR, Trop2, CDH3, and TAAs

The identification of Her2, EGFR, Trop2, CDH3, or other TAAs as protein(s) that are normally expressed in a restricted set of tissues or cells, but which is also expressed in cancers such as those listed in Table I, opens a number of therapeutic approaches to the treatment of such cancers.

Of note, targeted antitumor therapies have been useful even when the targeted protein is expressed on normal tissues or cells, even vital normal organ tissues. A vital organ is one that is necessary to sustain life, such as the heart or colon. A non-vital organ is one that can be removed whereupon the individual is still able to survive. Examples of non-vital organs are ovary, breast, and prostate.

Expression of a target protein in normal tissue, even vital normal tissue, does not defeat the utility of a targeting agent for the protein as a therapeutic for certain tumors in which the protein is also overexpressed. For example, expression in vital organs is not in and of itself detrimental. In addition, organs regarded as dispensable, such as the prostate and ovary, can be removed without affecting mortality. Finally, some vital organs are not affected by normal organ expression because of an immunoprivilege. Immunoprivileged organs are organs that are protected from blood by a blood-organ barrier and thus are not accessible to immunotherapy. Examples of immunoprivileged organs are the brain and testis.

Accordingly, therapeutic approaches that inhibit the activity of a Her2, EGFR, Trop2, CDH3, or other TAA protein are useful for patients suffering from a cancer that expresses Her2, EGFR, Trop2, CDH3, or other TAA (such as, for example, those cancers set forth in Table I). These therapeutic approaches generally fall into three classes. The first class modulates Her2, EGFR, Trop2, CDH3, or other TAA function as it relates to tumor cell growth leading to inhibition or retardation of tumor cell growth or inducing its killing. The second class comprises various methods for inhibiting the binding or association of a Her2, EGFR, Trop2, CDH3, or other TAA protein with its binding partner or with other proteins. The third class comprises a variety of methods for inhibiting the transcription of a Her2, EGFR, Trop2, CDH3, or other TAA gene or translation of Her2, EGFR, Trop2, CDH3 or other TAA mRNA.

Accordingly, Cancer patients can be evaluated for the presence and level of Her2, EGFR, Trop2, CDH3, or other TAA expression, preferably using immunohistochemical assessments of tumor tissue, quantitative Her2, EGFR, Trop2, CDH3, or other TAA imaging, or other techniques that reliably indicate the presence and degree of Her2, EGFR, Trop2, CDH3, or other TAA expression. Immunohistochemical analysis of tumor biopsies or surgical specimens is preferred for this purpose, if applicable. Methods for immunohistochemical analysis of tumor tissues are well known in the art.

XIII.) Combination Therapy

In one embodiment, there is synergy when tumors, including human tumors, are treated with Her2, EGFR, Trop2, CDH3, or other TAA ADCs in conjunction with chemotherapeutic agents or radiation or combinations thereof. In other words, the inhibition of tumor growth by a Her2, EGFR, Trop2, CDH3, or other TAA ADC is enhanced more than expected when combined with chemotherapeutic agents or radiation or combinations thereof. Synergy may be shown, for example, by greater inhibition of tumor growth with combined treatment than would be expected from a treatment of only Her2, EGFR, Trop2, CDH3, or other TAA ADC or the additive effect of treatment with a Her2, EGFR, Trop2, CDH3, or other TAA ADC and a chemotherapeutic agent or radiation. Preferably, synergy is demonstrated by remission of the cancer where remission is not expected from treatment either from a Her2, EGFR, Trop2, CDH3, or other TAA ADC with treatment using an additive combination of a Her2, EGFR, Trop2, CDH3, or other TAA ADC and a chemotherapeutic agent or radiation.

The method for inhibiting growth of tumor cells using a Her2, EGFR, Trop2, CDH3, or other TAA ADC and a combination of chemotherapy or radiation or both comprises administering the Her2, EGFR, Trop2, CDH3, or other TAA ADC before, during, or after commencing chemotherapy or radiation therapy, as well as any combination thereof (i.e. before and during, before and after, during and after, or before, during, and after commencing the chemotherapy and/or radiation therapy). For example, the Her2, EGFR, Trop2, CDH3, or other TAA ADC is typically administered between 1 and 60 days, preferably between 3 and 40 days, more preferably between 5 and 12 days before commencing radiation therapy and/or chemotherapy. However, depending on the treatment protocol and the specific patient needs, the method is performed in a manner that will provide the most efficacious treatment and ultimately prolong the life of the patient.

The administration of chemotherapeutic agents can be accomplished in a variety of ways including systemically by the parenteral and enteral routes. In one embodiment, the Her2, EGFR, Trop2, CDH3, or other TAA ADCs and the chemotherapeutic agent are administered as separate molecules. Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, gemcitabine, chlorambucil, taxol and combinations thereof.

The source of radiation, used in combination with a Her2, EGFR, Trop2, CDH3, or other TAA ADC, can be either external or internal to the patient being treated. When the source is external to the patient, the therapy is known as external beam radiation therapy (EBRT). When the source of radiation is internal to the patient, the treatment is called brachytherapy (BT). In one embodiment, the radiation therapy is boron neutron capture therapy. In one embodiment, the radiation is Proton Boron Fusion Therapy.

The above described therapeutic regimens may be further combined with additional cancer treating agents and/or regimes, for example additional chemotherapy, cancer vaccines, signal transduction inhibitors, agents useful in treating abnormal cell growth or cancer, antibodies (e.g. Anti-CTLA-4 antibodies as described in WO/2005/092380 (Pfizer)) or other ligands that inhibit tumor growth by binding to IGF-1R, and cytokines.

When the mammal is subjected to additional chemotherapy, chemotherapeutic agents described above may be used. Additionally, growth factor inhibitors, biological response modifiers, anti-hormonal therapy, selective estrogen receptor modulators (SERMs), angiogenesis inhibitors, and anti-androgens may be used. For example, anti-hormones, for example anti-estrogens such as Nolvadex (tamoxifen) or, anti-androgens such as Casodex (4'-cyano-3-(4-fluorophenylsulphonyl)-2-hydroxy-2-methyl-3-'-(trifluoromethyl)propionanilide) may be used.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

XIV.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a Her2, EGFR, Trop2, CDH3, or other TAA Mab or several Her2, EGFR, Trop2, CDH3, or other TAA MAbs of the disclosure. Kits can comprise a container comprising a drug unit. The kit can include all or part of the Her2, EGFR, Trop2, CDH3, or other TAA ADCs and/or diagnostic assays for detecting cancer and/or other immunological disorders.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as Her2, EGFR, Trop2, CDH3, or other TAA ADCs of the disclosure. The article of manufacture typically comprises at least one container and at least one label. Suitable containers include, for example, bottles, vials, syringes, and test tubes. The containers can be formed from a variety of materials such as glass, metal or plastic. The container can hold one or several Her2, EGFR, Trop2, CDH3, or other TAA ADCs and/or one or more therapeutics doses of Her2, EGFR, Trop2, CDH3, or other TAA ADCs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a Her2, EGFR, Trop2, CDH3, or other TAA Mab or ADC of the present disclosure.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Exemplary Embodiments

Among the provided embodiments are:
1) An antibody composition comprising, a triple mutation, wherein the triple mutation comprises a L234A modification, a L235A modification, and a L328C modification, and wherein said triple mutation modifies the Fcγ Receptor binding and antibody effector function.
2) The antibody of claim 1, wherein the antibody comprises an EGFR antibody.
3) The antibody of claim 1, wherein the antibody comprises a Her2 antibody.
4) The antibody of claim 1, wherein the antibody comprises a Trop2 antibody.
5) The antibody of claim 1, wherein the antibody comprises a CDH3 antibody.
6) The antibody of claim 1, wherein the antibody comprises a GPNMB antibody.
7) The antibody of claim 1, wherein the antibody comprises a DLL3 antibody.
8) The antibody of claim 1, wherein the antibody comprises a ENPP3 antibody.
9) The antibody of claim 1, wherein the antibody comprises a SLITRK6 antibody.
10) The antibody of claim 1, wherein the antibody comprises a CA9 antibody.
11) The antibody of claim 1, wherein the antibody comprises a PSMA antibody.
12) The antibody of claim 1, wherein the antibody comprises a CDH6 antibody.
13) The antibody of claim 1, wherein the antibody comprises a Glypican 3 antibody.
14) The antibody of claim 1, wherein the antibody comprises a EDNRB antibody.
15) The antibody of claim 1, wherein the antibody comprises a NECTIN-4 antibody.
16) The antibody of claim 1, wherein the antibody comprises a SLC34A2 antibody.
17) The antibody of claim 1, wherein the antibody comprises a Her3 antibody.
18) The antibody of claim 1, wherein the antibody comprises a NRP1 antibody.
19) The antibody of claim 1, wherein the antibody comprises a tumor associated antigen (TAA) antibody.
20) The Her2 antibody of claim 3, further comprising the antibody heavy chain comprising SEQ ID NO: 2.
21) The Her2 antibody of claim 3, further comprising the antibody heavy chain comprising SEQ ID NO: 3.
22) The Her2 antibody of claim 3, further comprising the antibody heavy chain comprising SEQ ID NO: 4.
23) The EGFR antibody of claim 2, further comprising the antibody heavy chain comprising SEQ ID NO: 7.
24) The EGFR antibody of claim 2, further comprising the antibody heavy chain comprising SEQ ID NO: 8.
25) The EGFR antibody of claim 2, further comprising the antibody heavy chain comprising SEQ ID NO: 9.
26) The EGFR antibody of claim 2, further comprising the antibody heavy chain comprising SEQ ID NO: 12.
27) The EGFR antibody of claim 2, further comprising the antibody heavy chain comprising SEQ ID NO: 13.
28) The EGFR antibody of claim 2, further comprising the antibody heavy chain comprising SEQ ID NO: 14.
29) The EGFR antibody of claim 2, further comprising the antibody heavy chain comprising SEQ ID NO: 17.
30) The EGFR antibody of claim 2, further comprising the antibody heavy chain comprising SEQ ID NO: 18.
31) The EGFR antibody of claim 2, further comprising the antibody heavy chain comprising SEQ ID NO: 19.
32) The Trop2 antibody of claim 4, further comprising the antibody heavy chain comprising SEQ ID NO: 22.
33) The Trop2 antibody of claim 4, further comprising the antibody heavy chain comprising SEQ ID NO: 23.
34) The Trop2 antibody of claim 4, further comprising the antibody heavy chain comprising SEQ ID NO: 24.
35) The CDH3 antibody of claim 5, further comprising the antibody heavy chain comprising SEQ ID NO: 27.

36) The CDH3 antibody of claim 5, further comprising the antibody heavy chain comprising SEQ ID NO: 28.
37) The CDH3 antibody of claim 5, further comprising the antibody heavy chain comprising SEQ ID NO: 29.
38) An antibody-drug-conjugate (ADC) comprising,
    (i) antibody composition comprising, a triple mutation, wherein the triple mutation comprises a L234A modification, a L235A modification, and a L328C modification, and wherein said triple mutation modifies the antibody effector function;
    (ii) a linker; and
    (iii) a drug unit, wherein said drug unit is conjugated specifically at site L328C.
39) The ADC of claim 38, wherein the antibody composition comprises an EGFR antibody.
40) The ADC of claim 38, wherein the antibody composition comprises an Her2 antibody.
41) The ADC of claim 38, wherein the antibody composition comprises an Trop2 antibody.
42) The antibody of claim 38, wherein the antibody comprises a CDH3 antibody.
43) The ADC of claim 38, wherein the antibody composition comprises a tumor associated antigen (TAA) antibody.
44) The ADC of claim 38, wherein the TAA antibody is set forth in Table IV.
45) The ADC of claim 38, further comprising a stretcher unit.
46) The ADC of claim 38, further comprising a spacer unit.
47) The ADC of claim 38, further comprising an amino acid unit.
48) An article of manufacture comprising the antibody of claim 1.
49) An article of manufacture comprising the ADC of claim 38.
50) A pharmaceutical composition comprising a therapeutically effective amount of the ADC of claim 38, and a pharmaceutically acceptable excipient.
51) A pharmaceutical composition comprising a therapeutically effective amount of the antibody of claim 1, and a pharmaceutically acceptable excipient.
52) A method of treating cancer in an individual comprising,
    (i) administering to said individual a therapeutic effective amount of the ADC of claim 38, wherein the cancer comprises cells that express the cancers set forth in Table I.
53) A method of treating cancer in an individual comprising,
    (i) administering to said individual a therapeutic effective amount of the antibody of claim 1, wherein the cancer comprises cells that express the cancers set forth in Table I.
54) A method of treating a disease in an individual comprising,
    (i) administering to said individual a therapeutic effective amount of the ADC of claim 38, wherein the disease comprises cells that express the cancers set forth in Table V.
55) A method of treating a disease in an individual comprising,
    (i) administering to said individual a therapeutic effective amount of the antibody of claim 1, wherein the disease comprises cells that express the cancers set forth in Table V.
56) An antibody-boron-conjugate (ABC) comprising,
    (i) antibody composition comprising, a triple mutation, wherein the triple mutation comprises a L234A modification, a L235A modification, and a L328C modification, and wherein said triple mutation modifies the antibody effector function;
    (ii) a linker; and
    (iii) a drug unit, wherein said drug unit comprises a borylated composition, and wherein said drug unit is conjugated specifically at site L328C.
57) The ABC of claim 56, wherein the antibody composition comprises an EGFR antibody.
58) The ABC of claim 56, wherein the antibody composition comprises an Her2 antibody.
59) The ABC of claim 56, wherein the antibody composition comprises a Trop2 antibody.
60) The ABC of claim 56, wherein the antibody composition comprises a CDH3 antibody.
61) The antibody of claim 56, wherein the antibody comprises a GPNMB antibody.
62) The antibody of claim 56, wherein the antibody comprises a DLL3 antibody.
63) The antibody of claim 56, wherein the antibody comprises a ENPP3 antibody.
64) The antibody of claim 56, wherein the antibody comprises a SLITRK6 antibody.
65) The antibody of claim 56, wherein the antibody comprises a CA9 antibody.
66) The antibody of claim 56, wherein the antibody comprises a PSMA antibody.
67) The antibody of claim 56, wherein the antibody comprises a CDH6 antibody.
68) The antibody of claim 56, wherein the antibody comprises a Glypican 3 antibody.
69) The antibody of claim 56, wherein the antibody comprises a EDNRB antibody.
70) The antibody of claim 56, wherein the antibody comprises a NECTIN-4 antibody.
71) The antibody of claim 56, wherein the antibody comprises a SLC34A2 antibody.
72) The antibody of claim 56, wherein the antibody comprises a Her3 antibody.
73) The antibody of claim 56, wherein the antibody comprises a NRP1 antibody.
74) The ABC of claim 56, wherein the antibody composition comprises a tumor associated antigen (TAA) antibody.
75) The ABC of claim 56, further comprising the antibody heavy chain comprising SEQ ID NO: 2.
76) The ABC of claim 56, further comprising the antibody heavy chain comprising SEQ ID NO: 3.
77) The ABC of claim 56, further comprising the antibody heavy chain comprising SEQ ID NO: 4.
78) The ABC of claim 56, further comprising the antibody heavy chain comprising SEQ ID NO: 7.
79) The ABC of claim 56, further comprising the antibody heavy chain comprising SEQ ID NO: 8.
80) The ABC of claim 56, further comprising the antibody heavy chain comprising SEQ ID NO: 9.
81) The ABC of claim 56, further comprising the antibody heavy chain comprising SEQ ID NO: 12.
82) The ABC of claim 56, further comprising the antibody heavy chain comprising SEQ ID NO: 13.
83) The ABC of claim 56, further comprising the antibody heavy chain comprising SEQ ID NO: 14.
84) The ABC of claim 56, further comprising the antibody heavy chain comprising SEQ ID NO: 17.

85) The ABC of claim 56, further comprising the antibody heavy chain comprising SEQ ID NO: 18.
86) The ABC of claim 56, further comprising the antibody heavy chain comprising SEQ ID NO: 19.
87) The ABC of claim 56, further comprising the antibody heavy chain comprising SEQ ID NO: 22.
88) The ABC of claim 56, further comprising the antibody heavy chain comprising SEQ ID NO: 23.
89) The ABC of claim 56, further comprising the antibody heavy chain comprising SEQ ID NO: 24.
90) The ABC of claim 56, further comprising the antibody heavy chain comprising SEQ ID NO: 27.
91) The ABC of claim 56, further comprising the antibody heavy chain comprising SEQ ID NO: 28.
92) The ABC of claim 56, further comprising the antibody heavy chain comprising SEQ ID NO: 29.
93) The ABC of claim 56, further comprising a stretcher unit.
94) The ABC of claim 56, further comprising a spacer unit.
95) The ABC of claim 56, further comprising an amino acid unit.
96) A pharmaceutical composition comprising a therapeutically effective amount of the ABC of claim 56, and a pharmaceutically acceptable excipient.
97) A method of treating cancer in an individual comprising,
   (i) administering to said individual a therapeutic effective amount of the ABC of claim 56, wherein the cancer comprises cells that express the cancers set forth in Table I.

EXAMPLES

Various aspects of the invention are further described and illustrated by way of the several examples that follow, none of which is intended to limit the scope of the invention.

Example 1: Methods of Generating Antibodies

The anti-Her2, anti-EGFR, anti-Trop2, and anti-CDH3 MAbs were generated by obtaining the amino acid sequences and performing codon optimization for the corresponding nucleotide sequences. (See, Table VI—Antibody Sequences 1-30). Gene fragments were synthesized and cloned into the restriction enzyme sites of the dual HC and LC expression vector cassettes for stable expression. For transient constructs, separate expression vectors for HC and LC were generated and co-transfected with HC to LC ratio of 1 to 3. The Fc variants were constructed either via site-directed mutagenesis or partial gene fragment synthesis followed by subcloning using techniques known in the art. Stable or transient expression vectors were constructed and purified with endotoxin-free DNA purification kit prior to transfection. Stably transfected Chinese Hamster Ovary (CHO) cells underwent selection and recovery process for the generation of stable pools expressing recombinant antibodies and Fc variants. For the antibody generation, fed-batch production process with typical culture duration of 8 to 12 days was used for stably transfected pools, for transient expression, transfected cells were cultured for 6-8 days post transfection prior to harvest. Subsequently, Protein-A affinity purification was performed for harvested cell culture fluid and purified materials were buffer exchanged into phosphate-buffered saline (PBS). Quality of recombinant antibodies can be assessed by size-exclusion chromatography, SDS-PAGE and other methods known in the art.

Example 2: Single and/or Triple Mutant MAbs do not Affect Target Binding

Target antigen binding was evaluated using an enzyme linked immunoassay (ELISA). Briefly, 96-well ELISA plates were coated with 0.05-0.075 ug of recombinant human soluble extracellular domain (ECD) of Her2/ErbB2 or EGFR or Trop2 (Sino Biologicals, Inc, Beijing, China) or 0.075 ug of recombinant human CDH3 full-length (Abnova, Taiwan). Subsequently, the plates were washed and blocked with ELISA blocking buffer. The plates were then incubated with testing samples (i.e., the wild-type or the Fc variants of anti-HER2, anti-EGFR, anti-TROP2 and anti-CDH3 mAbs at the concentration ranges of 0.0001-6.667 nM for the anti-HER2 and anti-EGFR mAbs and 0.0003-20 nM for anti-TROP2 and anti-CDH3 mAbs, serially diluted 3-fold in 1×PBS containing 1% BSA, 0.05% tween-20, for two (2) hours at room temperature. After washing to remove unbound antibodies, the bound antibodies were detected with horseradish peroxidase (HRP) conjugated goat anti-human-Fc-specific polyclonal antibody (Jackson ImmunoResearch, West Grove, Pa.). After washing to remove unbound detection antibody, a slow kinetic substrate solution of tetramethylbenzidine (TMB) was added to the wells where color develops in proportion to the amount of testing samples. The optical density (OD) of the color was measured at 650 nm and was used for determination of the amount of testing samples bound to the target antigen. Detectable binding of antibodies over the range of test concentrations was analyzed using the one-site binding, nonlinear regression analysis with GraphPad Prism.

The results show that when compared to the wild-type, the mAbs with the single mutation L328C, double mutation L234A and L235A, and the triple mutation L234A, L235A, and L328C bind the target, and the triple mutation does not affect target binding (FIGS. 1, 2, 3, 4, 5, and 6), as is the case with the single and double mutation.

Example 3: Inhibition of FcγRI Binding is Observed for Triple Mutant MAbs

FcγRI binding was evaluated using an enzyme linked immunoassay (ELISA). Briefly, 96-well ELISA plates were coated with recombinant human soluble ECD of CD64/FCGRIA (Sino Biological, Inc. Beijing, China) in 1×PBS (pH7.4) coating buffer. Subsequently the plates were washed and blocked with ELISA blocking buffer. The plates were incubated with testing samples (i.e., the wild-type or the Fc variants of trastuzumab, panitumumab cetuximab, nimotuzumab, sacituzumab, or anti-CDH3 (5836)) at the concentrations ranges of 0.005-80 ug/ml (or 0.002-30 ug/ml), serially diluted 4-fold in 1×PBS containing 1% BSA, 0.05% tween-20, for two (2) hours at room temperature. After washing to remove unbound antibodies, the bound antibodies were detected with horseradish peroxidase (HRP) conjugated goat anti-human Fc-specific polyclonal antibody (Jackson ImmunoResearch, West Grove, Pa.). After washing to remove the unbound detection antibody, a slow kinetic substrate solution of tetramethylbenzidine (TMB) was added to the wells where color develops in proportion to the amount of testing samples. The optical density (OD) of the color was measured at 650 nm and was used for determination of the amount of testing samples bound to FcγRI. Detectable binding of antibodies over the range of test concentrations was analyzed using the one-site binding, nonlinear regression analysis with GraphPad Prism.

The results show that a substantial inhibition of FcγRI binding was observed for the triple mutant as compared to the wild-type, single mutant L328C, and double mutant L234A & L235A (FIGS. 7, 8, 9, 10, 11 and 12).

Example 4: Suppression of FcγRIIA (CD32) Binding is Observed for Triple Mutant MAbs Binding of antibodies to the low affinity FcγRIIA receptor was determined by a modified sandwich format ELISA. Briefly, microtiter plates were coated with an anti-his tag antibody (Novus, NBP1-25939 lot #A4) 100 ul/well at 4 ug/ml. Wells were then blocked with PBS containing BSA. Then, serial dilutions of Fc variants mixed with FcγRIIa at different ratios (CD32) (Sino Biological, Inc. Beijing, China, cat #10374-H08H) were added and plates were incubated at 4° C. for overnight. After washing with PBS, a 1:3,000 dilution of horseradish peroxidase (HRP)-labeled goat anti-hIgG Fc, JacksonImmunoResearch) in PBS-T plus 1% BSA was added to detect His-tag captured FcγRIIA and Mab complexes. The results were visualized by the addition of tetramethylbenzidine (TMB) and the optical density (OD) measured at 650 nm. Data representing detectable binding of antibodies to FcγRIIA and captured by anti-his tag Abs over the range of Fc variant test concentrations was analyzed by one-site binding nonlinear regression analysis using Graph-Pad Prism software.

The results show that suppression of FcγRIIA binding is observed for the triple mutant and the single mutant L328C as compared to the wild-type and double mutant L234A & L235A for all antibodies tested (FIGS. 13, 14, 15, and 16).

Example 5: Inhibition of FcγRIIIa Binding is Observed for Triple Mutant MAbs

FcγRIIIa binding was evaluated using an enzyme linked immunoassay (ELISA). Briefly, 96-well ELISA plates were coated with of recombinant human soluble ECD of hCD16a/ FCGRIIIA (Sino Biological, Inc, Beijing, China) in 1×PBS (pH7.4) coating buffer. Subsequently the plates were washed and blocked with ELISA blocking buffer. The plates were incubated with testing samples (i.e., the wild-type or the Fc variants of trastuzumab, panitumumab cetuximab or nimotuzumab) at the concentrations ranges of 0.005-80 ug/ml, serially diluted 4-fold in 1×PBS containing 1% BSA, 0.05% tween-20, for two (2) hours at room temperature. After washing to remove unbound antibodies, the bound antibodies were detected with horseradish peroxidase (HRP) conjugated goat anti-human Fc-specific polyclonal antibody (Jackson ImmunoResearch, West Grove, Pa.). After washing to remove unbound detection antibody, a slow kinetic substrate solution of tetramethylbenzidine (TMB) was added to the wells where color develops in proportion to the amount of testing samples. The optical density (OD) of the color was measured at 650 nm and was used for determination of the amount of testing samples bound to FcγRIIa. Detectable binding of antibodies over the range of test concentrations was analyzed using the one-site binding, nonlinear regression analysis with GraphPad Prism.

The results show that a substantial inhibition of FcγRIIIa binding was observed for the triple mutant and the single mutant L328C as compared to the wild-type and double mutant L234A & L235A for all antibodies tested (FIGS. 17, 18, 19, 20, 21, and 22).

Example 6: Inhibition of FcRn Binding is Not Substantially Affected by Fc Variants and/or Triple Mutant MAbs FcRn binding was evaluated using an enzyme linked immunoassay (ELISA). Briefly, 96-well ELISA plates were coated with of recombinant human FcRn (Sino Biological, Inc, Beijing, China) in 1×PBS (pH 6.0) coating buffer. Subsequently, the plates were washed and blocked with ELISA blocking buffer. The plates were incubated with testing samples (i.e., the wild-type or the Fc variants of trastuzumab, panitumumab cetuximab or nimotuzumab, sacituzumab, or anti-CDH3 (5836)) at the concentrations ranges of 0.04-90 ug/ml (or 0.04-30 ug/ml), serially diluted 3-fold in 1×PBS (pH 6.0) containing 1% BSA, 0.05% tween-20, for two (2) hours at room temperature. After washing to remove unbound antibodies, the bound antibodies were detected with horseradish peroxidase (HRP) conjugated goat anti-human Fc-specific polyclonal antibody (Jackson ImmunoResearch, West Grove, Pa.). After washing to remove unbound detection antibody, a slow kinetic substrate solution of tetramethylbenzidine (TMB) was added to the wells where color develops in proportion to the amount of testing samples. The optical density (OD) of the color was measured at 650 nm and was used for determination of the amount of testing samples bound to FcRn. Detectable binding of antibodies over the range of test concentrations was analyzed using the one-site binding, nonlinear regression analysis with GraphPad Prism.

The results show that inhibition of FcRn binding was not substantially affected by the Fc variants including, but not limited to the triple mutant antibodies as compared to the wild-type antibodies (FIGS. 23, 24, 25, 26, 27, and 28).

Example 7: Kinetic and Affinity Analysis for FcγRI, FcγRIIa, FcγRIIb, FcγRIIIa, FcγRIIIb, and FcRn Using Octet HTX System Binding affinities of different Fc Receptors toward anti-Her2 antibody and Fc variants were measured using Octet HTX System (Molecular Devices) at 25° C. Briefly, a Human FcR His-tagged recombinant protein panel (FcγRI, FcγRIIA, FcγRIIB, FcγRIIIA-F, FcγRIIIA-V, FcγRIIIB, and FcRn) were loaded onto Anti-Penta His (H1S1K) biosensors. The loaded sensors were dipped into serial dilutions of Mab test samples (300 nM start, 1:2 dilution, 7 points) in a buffer composed of PBS with 0.1% BSA, 0.02% Tween-20 pH7.4 or for FcRn analysis, pH 6.0. Kinetic constants were calculated using a monovalent (1:1) binding model. An antibody known to bind to the FcR panel was used as positive control. The equilibrium dissociation constant (KO, defined as a ratio of $k_{dis}/k_{on}$, was determined by analyzing the sensogram curves obtained with several different concentrations.

The results, as summarized in FIG. 29, shows the effects of introducing a single or triple mutation in the Fc domain on binding to FcγRI, FcγRIIA, FcγRIIB, FcγRIIIA (F158 and V158 variants) and FcγRIIIB, as well as the effect on FcRn binding. For the FcγRI binding, a substantial reduction in the $K_D$ value observed for the triple mutant is mostly attributable toward the increase in the antibody dissociation rate ($k_d$) (FIG. 29). The quick dissociation from its antigen for the triple mutant is also depicted in the chromatogram (FIG. 30). Only a slight reduction in the association rate ($k_{on}$) was observed for the triple mutant as compared to the wild-type or single mutant antibody. No $K_d$ value could be determined for other Fcγ receptors due to the undetectable binding of the triple mutant (FIG. 29). In contrast, the $K_D$ value observed for the FcRn was not compromised for the triple mutant, implicating the reduction of binding affinity for the triple mutant is specific to Fc gamma receptor isoforms.

Example 8: Binding Kinetic Analysis for FcγRI (Dissociation Rate) Using Octet

Further binding experiments were performed on Octet HTX at 25° C. Briefly, a Human FcR His-tagged recombinant protein panel (FcRI) was loaded onto Anti-Penta His (H1S1K) biosensors. The loaded sensors were dipped into serial dilutions of Mab test samples (300 nM start, 1:2 dilution, 7 points) in a buffer composed of PBS with 0.1% BSA, 0.02% Tween-20 pH7.4 or for FcRn analysis, pH 6.0. Kinetic constants were calculated using a monovalent (1:1) binding model. An antibody known to bind to the FcR panel was used as positive control.

The results show that the triple mutant dissociation rate is faster for the FcγRI when compared to the wild-type and single mutant (FIG. 30).

Example 9: ADCC Analysis of Fc Variants Using Flow Cytometry

In order to evaluate Fc variant-mediated Antibody-dependent cellular cytotoxicity (ADCC), flow cytometric ADCC evaluation was employed. Briefly, human cancer cells were used as the target cells and frozen PBMCs were used as the effector cells. Human cancer cells were labeled with 8 uM carboxyfluorescein succinimidyl ester (CFSE) dye (Selleckchem, cat #S8269 lot #S826901) for 30 minutes, washed twice with cell culture medium, and added to U bottom 96 plate and a suitable concentration of Fc variant was added. ADCC was initiated by adding human PBMCs as effector cells (4-8:1 as the effector:target (E:T) ratio). The plate was further incubated overnight at 37° C. in a 5% CO2, humidified atmosphere. The cells were washed twice and stained with a 1:500 dilution of Fixable Viability Dye (FVD, eBioscience, CA) which stains dead cells. After 30 minutes of incubation, the cells were washed with PBS containing 2% FBS, and then subjected to flow cytometry analysis using an Attune Nxt. (Thermo Fisher Scientific). For each experiment, measurements were conducted in triplicate. The percentage of dead target cells (CFSE positive and FVD positive) in total target cells (CFSE positive) were used as to determine % cytotoxicity. Data are shown as % cytotoxicity bar graphs using GraphPad Prism software.

The results show that reduction in ADCC was observed with Fc variants with the triple mutant markedly reduced for each mAb as compared to the wild-type (FIGS. 31, 32, 33, and 34).

Example 10: CDC Analysis of Fc Variants Using Flow Cytometry

Complement-dependent cellular cytotoxicity (CDC) was determined by the lactate dehydrogenase (LDH) release assay using baby rabbit serum as complement source and human cancer cells as target cells. Briefly, target cells ($20\times10e^3$ per well) were distributed into 96-well U-bottomed plates and pre-incubated with Fc variants for 30 minutes on ice. Then diluted complement were added and further incubated at 37° C. (5% CO2, humidified atmosphere) for 4 hours. Assays were performed in triplicate with or without antibodies. The maximum release was prepared with target cells lysed with the lysis solution. The supernatant LDH activity was measured with a nonradioactive cytotoxicity assay kit (Promega cat #G1781). Released LDH activity indicative of cell death was determined by optical density readings at 490 nm suing a spectrophotometer (Cytation1 Biotek). Percentage cytotoxicity was calculated according to the formula: Cytotoxicity (%)=100×(Experimental release-Spontaneous release)/(Maximum release-Spontaneous release). Data are shown as cytotoxicity bar graphs created using GraphPad Prism software.

The results show that reduction in CDC was observed with Fc variants with the triple mutant markedly reduced for each MAb (FIGS. 35, 36, 37, and 38).

Example 11: C1q Binding of Fc Variants Using ELISA

C1q binding was evaluated using an enzyme linked immunoassay (ELISA). Briefly, 96-well ELISA plates were coated with 60 ul/well of 1 ug/ml testing samples (i.e., the wild-type or the Fc variants of trastuzumab, panitumumab sacituzumab & anti-CDH3-5836) in 1×PBS (pH7.4) coating buffer. Subsequently the plates were washed and blocked with ELISA blocking buffer (PBS containing 1% BSA). The plates were incubated with diluted human C1q (sigma Cat #C1740 lot #SCC6462) at the concentrations ranges of 0.625-40 ug/ml, serially diluted 2-fold in 1×PBS containing 1% BSA, 0.05% tween-20, for two (2) hours at room temperature. After washing plates, 60 ul/well of Rabbit anti-h C1q (Dako A0136 lot #20047640) at 5 ug/ml in 1% of BSA and 0.05% tween in PBS (PBS-T) was added and incubated at room temperature for 1.0 hour. After washing to remove unbound antibodies, the bound antibodies were detected with horseradish peroxidase (HRP) conjugated Goat anti Rabbit HRP-specific polyclonal antibody (Jackson ImmunoResearch, cat #111-036-046 West Grove, Pa.). A slow kinetic substrate solution of tetramethylbenzidine (TMB) was added and the optical density (OD) of the color was measured at 650 nm. The data representing detectable binding of antibodies over the range of test concentrations was analyzed by one-site binding nonlinear regression analysis using GraphPad Prism software.

The results show that reduction in C1q binding was observed with Fc variants and the triple mutant markedly reduced for each MAb (FIGS. 39, 40, 41, and 42).

Example 12: Generation of Site-Specific ADC and Characterization

Generation of Site-Specific Thiols

The hinge disulfides of Fc variants were reduced with DTT in PBS for fifteen (15) min. at room temperature and the antibody was purified from the excess of the reducing agent by desalting using PD-10 column into a pH 6.5 buffer. The expected free thiols were confirmed by the Ellman's test. The hinge disulfides were then reformed using a 35-fold excess of dehydroascorbic acid (DHA) with respect to the antibody concentration. The progress of reoxidation is monitored by the Ellman's test. The malemide-payload is added when the thiol-to-antibody ratio has reached approximately 2.0.

Conjugate Preparation

To generate a site-specific ADC of the invention, an antibody conjugate using a proprietary linker(s) denoted LOL1 was prepared by adding the maleimide-linker to the activated site-specific antibody. The process of activation (i.e. liberation of the free thiols) is described above (Generation of Site-Specific Thiols). The linker solution in DMSO is added at 1.2 mol eq. of the linker to thiol. The reaction is stirred at room temperature for 45-60 min. The resulting conjugate is purified into histidine formulation buffer (pH6) using PD-10 or similar desalting column and analyzed.

Conjugate Evaluation

In order to verify the ability to produce a site-specific ADC using either the single (i.e. L328C) or the triple mutant (i.e. L234A, L235A, L328C) antibody, three techniques were employed: (i) intact mass analysis, (ii) peptide mapping and (iii) reverse-phase HPLC. Reverse phase HPLC is the principal method for dissecting a cysteine-based conjugate and was employed to confirm that the payload is conjugated predominantly or solely to the heavy chain and only at a single position within the heavy chain and that the product is therefore, site-specific. The intact analysis by mass spectrometry was employed to confirm that the conjugated heavy chain has the correct and expected mass (i.e. HC+Payload) whereas peptide mapping confirms that the payload is tethered to the specific position within the heavy chain. Here, the intact mass analysis was utilized to prove that the LOL-1 conjugated anti-HER2 mAb with triple mutation is comprised of the singly conjugated heavy chain and non-conjugated light chain (FIG. 44). Peptide mapping of both single and triple mutant vcMMAE conjugated anti-EGFR mAb No. 1 with either single or triple mutations revealed the ACPAPIEK peptide within the heavy chain is both the site of the L328C mutation and the site of conjugation (FIGS. 54, 55).

While the mass analyses are low-throughput techniques, reverse-phase HPLC is a high throughput technique that shows the relative composition of ADC. It is particularly useful for conjugates and ADCs conjugated through cysteine side chain because with monoclonal antibodies there only eight (8) cysteines available for conjugation that are present in the wild-type human IgG1.

Generally, each Cys-based ADC carries a finite number of payloads that need to be known. It is generally accepted that ADCs which utilize vcMMAE as the payload should carry anywhere from two (2) to four (4) payloads to be efficient in tumor killing. Furthermore, their make-up is a distribution of payloads ranging from 0 (unconjugated) to 8 (fully conjugated). Antibodies engineered to carry a defined number (typically 2 per mAb) of the payload (i.e site-specific ADCs that lack the distribution and the high payload-to-mAb species) have been shown to be advantageous in clinical efficacy, safety or stability.

Accordingly, we use analytical methods, with reverse phase chromatography assay being the principal technique, to dissect the make-up of the ADCs resulting from conjugation of vcMMAE. Each species (i.e. heavy chain, light chain, and conjugated species) are identified based on both the retention time and the UV250/280 ratio and the DAR (drug-to mAb ratio) is calculated. Furthermore, we showed that the payload is tethered predominantly or fully to the heavy chain and that the heavy chain with a single payload is the principle species, a primary attribute of site-specific conjugation.

The materials and methods of the analysis were performed as follows:

Intact Mass Spectrometry Analysis

Briefly, the samples were prepared by adding 1/20 the volume of 200 mM DTT and incubating at 37° C. for 1 hour. Samples were analyzed using an Agilent 1260 LC and an Agilent 6520 Q-TOF mass spectrometer. The liquid chromatography column was a 2 mm ID×10 cm long column packed with 10 µm PLRPS polystyrene reverse phase packing. The solvents were 0.1% formic acid in water (A) and 0.1% formic acid in acetonitrile (B). The gradient was a 1-minute hold a 1% B, a 14-minute ramp to 70% B, 1-minute ramp to 90% B, 1-minute hold at 90% B, and 1-minute ramp back to 1% B. Data was acquired using Agilent Mass Hunter Data Acquisition software and analyzed using Agilent Mass Hunter Qualitative Analysis with Bioconfirm. Deconvolution used the Maximum Entropy model.

The results show that the LOL1-conjugated anti-HER2 antibody with triple mutation produced a distinct retention shift, suggesting only one positional isomer was formed and is highly indicative of a site-specific conjugation (FIG. 43). Further confirmation by intact mass analysis showed that the above LOL1 conjugated triple mutant anti-HER2 antibody is site-specific (FIG. 44). Only the unconjugated light chain (LC) with average mass of 23440 Dalton (Da) was detected (FIG. 44). The 23462 Da peak represents sodium adduct normally formed in the LC-MS systems. For the heavy chain (HC), the conjugated species are found with the average mass of 49487 Da (reflecting the c-terminal lysine deletion (-K) typically observed in Chinese Hamster Ovary (CHO) cell culture system utilized for antibody production) and 49613 Da product (reflecting the HC with intact unprocessed c-terminal lysine (+K)). Neither the unconjugated HC species nor the HC with the second conjugation site is found (FIG. 44). Taken together, the intact mass analysis confirmed that (i) only the single LOL1 payload is conjugated to the heavy chain; (ii) no conjugation to the light chain is detected and (iii) such a conjugated could form only with the engineered Cys-328 and not with any of the hinge-region cysteines.

The results in FIGS. 43 and 44 confirm that the ADCs conjugated with proprietary payload LOL-1 are 100% site-specific at L328C for the triple Fc mutant.

Reverse Phase Chromatography Analysis

Additionally, antibodies and/or antibody drug conjugates were analyzed by reverse phase chromatography using the following protocols. Briefly, An ADC or mAb was reduced with DTT and analyzed using Acquity C4 Wide Pore column (100×2.1 mm, 300 Å, Waters) using Waters H-class UPLC system. The column was maintained at 80° C. The mAb light and heavy chains were resolved in the acetonitrile (0.1% TFA) gradient.

The results in FIG. 45 show the heavy chain with a single payload (H1) is the principle species which suggests that the conjugation is site-specific, and the payload resides on the Cys328 and not within the hinge region. Additionally, FIG. 46 shows a reverse-phase column chromatography profile for L328C variant of anti-Trop2 Mab conjugated with vcMMAE. It is shown that greater than 80% of site-specific conjugation occurs on Cys328 heavy chain.

FIG. 47 shows a reverse-phase column chromatography profile for L234A, L235A, L328C triple mutant variant of anti-Trop2 Mab conjugated with vcMMAE. It is shown that greater than 70% of site-specific conjugation occurs on Cys328 heavy chain. FIG. 48 shows a reverse-phase column chromatography profile for L234A, L235A, L328C variant of anti-EGFR Mabs conjugated with vcMMAE. It is shown that DAR1 is the predominant species with greater than 80%-90% of site-specific conjugation occurring on Cys328 heavy chain.

FIG. 49 shows the peak assignment and DAR calculation based on RP-HPLC data provided in FIG. 49. The unconjugated Mab (control) was used to identify both the retention time and the UV250/280 ratio for both the heavy and light chain. It is noted that these parameters are required for both peak assignment as well as DAR determination. The DAR was calculated as follows:

$$DAR = \left( \frac{LC_1}{LC_0 + LC_1} + \frac{\sum_{n=0}^{3}(HC_n * n)}{HC_{Total}} \right) * 2$$

Where $LC_0$, $LC_1$ are the AUC of LC unconjugated and vcMMAE-conjugated, respectively $HC_n$ is the AUC of each heavy chain species and n is the multiple of the vcMMAE payload FIG. 50 shows a summary of analytical attributes including the average DAR, percent monomer peak as determined by SEC and percent of DAR1 species for vcMMAE or LOL1 conjugated mAbs with single or triple Fc variants.

Peptide Mapping

In order to confirm that the payload is tethered to the specific position within the heavy chain a peptide mapping analysis was performed using the following protocols.

(i) Sample Preparation:

Mab(s) or and ADC(s) were reduced with DTT and free thiols alkylated using iodoacetamide per published procedures known in the art. In order to obtain a trypsin digest peptide map, the above antibody was digested as follows: antibody was reduced with DTT under partially denaturing conditions using 5M guanidine. Iodoacetamide was added at a twice the concentration of DTT. The alkylated mAb was purified by desalinating using Zeba-Spin (Thermo) columns into 100 mM phosphate buffer. Trypsin was added to each sample and the samples were incubated overnight at 37° C., evaporated to dryness and resuspend pellets in 100 µL of 5% ACN, 95% water, 0.1% formic acid (ii) LC-MS:

After samples were prepared, a 5.0 µL sample was injected to an ultimate 3000 nano LC, which was equipped with a 75 µm×2 cm trap column packed with C18 3 µm bulk resins (Acclaim PepMap 100, Thermo Scientific) and a 75 µm×15 cm analytical column with C18 2 µm resins (Acclaim PepMap RSLC, Thermo Scientific). The nanoLC gradient was 3-35% solvent B (A=H2O with 0.1% formic acid; B=acetonitrile with 0.1% formic acid) over 40 min and from 35% to 85% solvent B in 5 min at flow rate 300 nL/min. The nannoLC was coupled with a Q Exactive Plus orbitrap mass spectrometer (Thermo Fisher Scientific, San Jose, Calif.). The ESI voltage was set at 1.9 kV, and the capillary temperature was set at 275° C. Full spectra (m/z 350-2000) were acquired in profile mode with resolution 70,000 at m/z 200 with an automated gain control (AGC) target of $3\times10^6$. The most abundance 15 ions were subjected to fragmentation by higher-energy collisional dissociation (HCD) with normalized collisional energy of 25. MS/MS spectra were acquired in centroid mode with resolution 17,500 at m/z 200. The AGC target for fragment ions are set at $2\times10^4$ with maximum injection time of 50 ms. Charge states 1, 7, 8, and unassigned were excluded from tandem MS experiments. Dynamic exclusion was set at 45.0 s.

The results in FIG. 51 show the characteristic daughter ions following fragmentation of a vcMMAE-peptide. In addition, FIG. 52 shows sequence coverage of anti-EGFR antibody No 1 with triple mutation conjugated with vcMMAE. FIG. 53 shows representative TIC chromatograms. The differences are shown in the circles. FIG. 54 shows the charge state of the peptide containing the conjugation site for anti-EGFR antibody No 1 with triple mutation. The unconjugated control mAb has the [M+1] ion with M/z of 886 that matches the ACPAPIEK peptide from the heavy chain (A). Its +2 ion is shown on the inset. The two prominent daughter ions with M/z of 486 and 654 are shown in (B). In the vcMMAE conjugate, this peptide is eluted off the reverse phase column in a different place due to conjugation to cysteine (see previous figure). The resulting product is identified in C (+2 and +3 charge state are shown). The fragments contain the same ions as above (D, filled arrows) that confirms that this is the same ACPAPIEK peptide. Additional fragments with M/z of 686, 506 and 321 (D, hollow arrows) belong to VCMMAE and correspond to those on FIG. 52. Finally, FIG. 55 shows that the conjugation site for anti-EGFR antibody No. 1 with single mutation (L328C) was also confirmed on the ACPAPIEK peptide of the heavy chain.

A list of antibody fragments and confidence scores for the peptide map for the single mutant of vcMMAE-conjugated anti-EGFR antibody No. 1 is shown in Table VII. A list of antibody fragments and confidence scores for the peptide map for the triple mutant of vcMMAE-conjugated anti-EGFR antibody No. 1 is shown in Table VIII.

Example 13: Cytotoxicity of Fc Single Mutant and/or Triple Mutant Conjugates of vcMMAE Cytotoxic effects of Fc single mutant or triple mutant antibodies conjugated with vcMMAE on tumor cell lines were measured using the CellTiter-GLo assay kit (Promega cat #G7571). The CellTiter-Glo® Luminescent Cell Viability Assay is a homogeneous method to determine the number of viable cells in culture based on quantitation of the ATP present, which signals the presence of metabolically active cells. Briefly, human tumor cells in opaque-walled multi-well plates (6000/well of human cancer cells in 100 µl cell culture medium) were incubated with serial dilutions of Fc single mutant or triple mutant antibody vcMMAE conjugates at 37° C. (5% CO2, humidified atmosphere) for 3 to 4 days. Following incubation, 100 µl of CellTiter-Glo® substrate was added to the wells. Luminescence was recorded after 10 min using Cytation1 (Biotek) plate reader. The percent survival was calculated according to the formula: Survival (%)=100×(Experimental RLU−Medium only RLU)/(Cell only RLU−Medium only RLU) and data was analyzed by a non-linear regression log(inhibitor) vs. response (three parameters) curve fit using GraphPad Prism software. The cell lines tested in the cytotoxicity assays have surface expression positive for the respective target of the mAb used in the assay. Specifically, HCC1954 cell line was tested for anti-HER2 mAb harboring single mutant (L328C). For anti-EGFR mAbs with either single or triple mutants, MDA MB468 cell line was tested. For anti-TROP2 antibodies with either single or triple mutants, SK BR3 cell line was evaluated.

The results in FIGS. 56, 57, 58, 59, 60, and 61 show that the in vitro cytotoxicity of the antibodies with single or triple Fc mutants were enhanced by their conjugation with vcMMAE, an MMAE derivative with cleavable dipeptide valine-citrulline (vc) linker which facilitates efficient and selective drug cleavage inside the target cells by lysosomal Cathepsin B after internalization. The results further showed that site-specific conjugated mAbs with vcMMAE exhibited potent and selective cytotoxic activity against the antigen-positive tumor cell lines in a dose-dependent manner. In contrast, unconjugated mAbs with single or triple mutants showed substantially less or no cytotoxic effect. Taken together, these results demonstrate in vitro efficacy of ADCs comprised of a monoclonal antibody covalently linked in a site-specific manner to a cytotoxin that enables release of the cytotoxic drug upon binding and internalization by the cell.

Example 14: Human Clinical Trials for the Treatment of Human Carcinomas Through the Use of Her2, EGFR, TROP2, CDH3, or other TAA Triple Mutant MAbs and Site-Specific Conjugated ADCs Her2, EGFR, Trop2, CDH3, or other TAA ADCs are synthesized in accordance with the present invention which specifically accumulate in a tumor cell and are used in the treatment of certain tumors and other immunological disorders and/or other diseases (See, Table I and Table V). In connection with each of these indications, two clinical approaches are successfully pursued.

I.) Adjunctive therapy: In adjunctive therapy, patients are treated with Her2, EGFR, Trop2, CDH3, or other TAA ADCs in combination with a chemotherapeutic or pharmaceutical or biopharmaceutical agent or a combination thereof. Primary cancer targets are treated under standard protocols by the addition of Her2, EGFR, Trop2, CDH3, or other TAA ADCs. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the Her2, EGFR, Trop2, CDH3, or other TAA ADCs in monotherapy of tumors, the Her2, EGFR, Trop2, CDH3, or other TAA ADCs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single Her2, EGFR, Trop2, CDH3, or other TAA ADC injection may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the Her2, EGFR, Trop2, CDH3, or other TAA ADC, the individual mechanics of the irradiation mechanism (reactor) and the particular therapeutic or prophylactic effect to be achieved, and (b) the limitations inherent in the art of compounding such an compound for the treatment of sensitivity in individuals.

Clinical Development Plan (CDP)

The CDP follows and develops treatments of cancer(s) and/or immunological disorders (See, Table I and Table V) using Her2, EGFR, Trop2, CDH3, or other TAA ADCs of the disclosure. Trials initially demonstrate safety and thereafter confirm efficacy in repeat doses. Trials are open label comparing standard chemotherapy with standard therapy plus Her2, EGFR, Trop2, CDH3, or other TAA ADCs. As will be appreciated, one non-limiting criteria that can be utilized in connection with enrollment of patients is concentration of Her2, EGFR, Trop2, CDH3, or other TAA ADCs in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE 1

List of Cancer(s) to be Treated.

| # | Cancers |
|---|---|
| 1 | Acute myeloid leukemia |
| 2 | Adrenocortical carcinoma |
| 3 | Adult T-cell leukemia/lymphoma |
| 4 | B-cell chronic lymphocytic leukemia |
| 5 | B-cell Hodgkin's lymphoma |
| 6 | B-cell non-Hodgkin's lymphoma |
| 7 | Bladder cancer |
| 8 | Breast cancer |
| 9 | Chronic lymphatic leukemia |
| 10 | Clear cell renal cell carcinoma |
| 11 | Colorectal cancer |
| 12 | Diffuse large B-cell lymphoma |
| 13 | Glioblastoma |
| 14 | Gastric cancer |
| 15 | Hairy cell leukemia |
| 16 | Head and neck cancer |
| 17 | Hematologic cancers |
| 18 | Hodgkin lymphoma |
| 19 | Melanoma |
| 20 | Metastatic Merkel cell carcinoma |
| 21 | Multiple myeloma |
| 20 | Neuroblastoma |
| 21 | Non-Hodgkin's lymphoma |
| 22 | Non-small cell lung cancer |
| 23 | Ovarian cancer |
| 24 | Pancreatic cancer |
| 25 | Prostate cancer |
| 26 | Small cell lung cancer |
| 27 | Stomach neoplasms |
| 28 | Squamous cell carcinoma |
| 29 | Triple-negative breast cancer |
| 30 | Urothelial cancer |
| 31 | Genital cancer |
| 32 | Cervical cancer |
| 33 | Esophageal cancer |
| 34 | Gastroesophageal junction adenocarcinoma |
| 35 | Glioma |

TABLE II

Amino Acid Abbreviations.

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix.
Adapted from the GCG Software 9.0 BLOSUM62 amino acid substitution matrix block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV

Tumor Associated Antigens (TAAs).

| Target |
|---|
| GPNMB |
| DLL3 |
| ENPP3 |
| SLITRK6 |
| CA9 |
| PSMA |
| CDH6 |
| Glypican 3 |
| EDNRB |
| NECTIN-4 |
| SLC34A2 |
| Her3 |
| NRP1 |

TABLE V

List of Diseases (Non-Cancer) to be Treated.

| | |
|---|---|
| 1 | angioedema |
| 2 | Arthritis, Rheumatoid arthritis |
| 3 | Asthma |
| 4 | atopic diseases |
| 5 | autoimmune diseases |
| 6 | autoimmune hepatitis |
| 7 | Colitis |
| 8 | *Clostridium difficile* colitis |
| 9 | Crohn's disease |
| 10 | Cryopyrin-associated periodic syndrome |
| 11 | Dermatitis |
| 12 | Dyslipidemias |
| 13 | Enterocolitis |
| 14 | Hemorrhage |
| 15 | Haemorrhagic shock |
| 16 | Haemophilia A |
| 17 | HIV infection |
| 14 | hyperimmunoglobulin D Syndrome |
| 15 | Immunologically mediated inflammatory disorders |
| 16 | inflammations of the airways, skin and gastrointestinal tract |
| 17 | migraine |
| 18 | Multiple sclerosis |
| 19 | ocular vascular diseases |

TABLE V-continued

List of Diseases (Non-Cancer) to be Treated.

| | |
|---|---|
| 20 | Osteoporosis |
| 21 | Pain* |
| 22 | Parkinson's Disease* |
| 23 | Paroxysmal nocturnal hemoglobinuria |
| 24 | Plaque psoriasis |
| 25 | Psoriasis |
| 26 | paroxysmal nocturnal hemaglobinuria |
| 27 | rheumatic diseases |
| 28 | Spondylitis |
| 29 | *Staphylococcus aureus* infection |
| 30 | Systemic lupus erythematosus (SLE) |
| 31 | Rheumatoid arthritis |
| 32 | thrombotic thrombocytopenic purpura, thrombosis |
| 33 | ulcerative Crohn's disease |
| 35 | X-linked hypophosphatemia |

TABLE VI

Antibody Sequences

Anti-HER2 Ab Heavy Chain Wild Type
EVQLVESGGGLVQPGGSLRLSCAASGFNIKDTYIHWVRQAPGKGLEWVARIYPTNGYTRYADSVKGRFTISADTSK
NTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 1)

Anti-HER2 Ab Heavy Chain L328C
EVQLVESGGGLVQPGGSLRLSCAASGFNIKDTYIHWVRQAPGKGLEWVARIYPTNGYTRYADSVKGRFTISADTSK
NTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKACPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
IS NO: 2)

Anti-HER2 Ab Heavy Chain L234A, L235A
EVQLVESGGGLVQPGGSLRLSCAASGFNIKDTYIHWVRQAPGKGLEWVARIYPTNGYTRYADSVKGRFTISADTSK
NTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPEAAGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
IS NO: 3)

Anti-HER2 Ab Heavy Chain L234A, L235A, L328C
EVQLVESGGGLVQPGGSLRLSCAASGFNIKDTYIHWVRQAPGKGLEWVARIYPTNGYTRYADSVKGRFTISADTSK
NTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPEAAGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKACPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 4)

Anti-HER2 Ab Light Chain Wild Type
DIQMTQSPSSLSASVGDRVTITCRASQDVNTAVAWYQQKPGKAPKLLIYSASFLYSGVPSRFSGSRSGTDFTLTISSL
QPEDFATYYCQQHYTTPPTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 5)

Anti-EGFR Ab No. 1 Heavy Chain Wild Type
QVQLQESGPGLVKPSETLSLTCTVSGGSVSSGDYYWTWIRQSPGKGLEWIGHIYYSGNTNYNPSLKSRLTISIDTSKT
QFSLKLSSVTAADTAIYYCVRDRVTGAFDIWGQGTMVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK (SEQ ID NO:
6)

Anti-EGFR Ab No. 1 Heavy Chain L328C
QVQLQESGPGLVKPSETLSLTCTVSGGSVSSGDYYWTWIRQSPGKGLEWIGHIYYSGNTNYNPSLKSRLTISIDTSKT
QFSLKLSSVTAADTAIYYCVRDRVTGAFDIWGQGTMVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKACPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK (SEQ ID NO:
7)

Anti-EGFR Ab No. 1 Heavy Chain L234A, L235A
QVQLQESGPGLVKPSETLSLTCTVSGGSVSSGDYYWTWIRQSPGKGLEWIGHIYYSGNTNYNPSLKSRLTISIDTSKT
QFSLKLSSVTAADTAIYYCVRDRVTGAFDIWGQGTMVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APEAAGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK (SEQ ID NO:
8)

Anti-EGFR Ab No. 1 Heavy Chain L234A, L235A, L328C
QVQLQESGPGLVKPSETLSLTCTVSGGSVSSGDYYWTWIRQSPGKGLEWIGHIYYSGNTNYNPSLKSRLTISIDTSKT
QFSLKLSSVTAADTAIYYCVRDRVTGAFDIWGQGTMVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPCP
APEAAGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKACPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK (SEQ ID NO:
9)

TABLE VI-continued

Antibody Sequences

Anti-EGFR Ab No. 1 Light Chain Wild Type
DIQMTQSPSSLSASVGDRVTITCQASQDISNYLNWYQQKPGKAPKLLIYDASNLETGVPSRFSGSGSGTDFTFTISSL
QPEDIATYFCQHFDHLPLAFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC (SEQ ID NO: 10)

Anti-EGFR Ab No. 2 Heavy Chain Wild Type
QVQLKQSGPGLVQPSQSLSITCTVSGFSLTNYGVHWVRQSPGKGLEWLGVIWSGGNTDYNTPFTSRLSINKDNSKS
QVFFKMNSLQSNDTAIYYCARALTYYDYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKRVEPKSCDKTHTCPP
CPAPELLGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK (SEQ ID NO:
11)

Anti-EGFR Ab No. 2 Heavy Chain L328C
QVQLKQSGPGLVQPSQSLSITCTVSGFSLTNYGVHWVRQSPGKGLEWLGVIWSGGNTDYNTPFTSRLSINKDNSKS
QVFFKMNSLQSNDTAIYYCARALTYYDYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKRVEPKSCDKTHTCPP
CPAPELLGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKACPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK (SEQ ID NO:
12)

Anti-EGFR Ab No. 2 Heavy Chain L234A, L235A
QVQLKQSGPGLVQPSQSLSITCTVSGFSLTNYGVHWVRQSPGKGLEWLGVIWSGGNTDYNTPFTSRLSINKDNSKS
QVFFKMNSLQSNDTAIYYCARALTYYDYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKKVEPKSCDKTHTCPP
CPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK (SEQ ID NO:
13)

Anti-EGFR Ab No. 2 Heavy Chain L234A, L235A, L328C
QVQLKQSGPGLVQPSQSLSITCTVSGFSLTNYGVHWVRQSPGKGLEWLGVIWSGGNTDYNTPFTSRLSINKDNSKS
QVFFKMNSLQSNDTAIYYCARALTYYDYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVDKRVEPKSCDKTHTCPP
CPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKACPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSPGK (SEQ ID NO:
14)

Anti-EGFR Ab No. 2 Light Chain Wild Type
DILLTQSPVILSVSPGERVSFSCRASQSIGTNIHWYQQRTNGSPRLLIKYASESISGIPSRFSGSGSGTDFTLSINSVESE
DIADYYCQQNNNWPTTFGAGTKLELKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC (SEQ ID NO: 15)

Anti-EGFR Ab No. 3 Heavy Chain Wild Type
QVQLQQSGAEVKKPGSSVKVSCKASGYTFTNYYIYWVRQAPGQGLEWIGGINPTSGGSNFNEKFKTRVTITADESS
TTAYMELSSLRSEDTAFYFCTRQGLWFDSDGRGFDFWGQGTTVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 16)

Anti-EGFR Ab No. 3 Heavy Chain L328C
QVQLQQSGAEVKKPGSSVKVSCKASGYTFTNYYIYWVRQAPGQGLEWIGGINPTSGGSNFNEKFKTRVTITADESS
TTAYMELSSLRSEDTAFYFCTRQGLWFDSDGRGFDFWGQGTTVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKACPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ
ID NO: 17)

Anti-EGFR Ab No. 3 Heavy Chain L234A, L235A
QVQLQQSGAEVKKPGSSVKVSCKASGYTFTNYYIYWVRQAPGQGLEWIGGINPTSGGSNFNEKFKTRVTITADESS
TTAYMELSSLRSEDTAFYFCTRQGLWFDSDGRGFDFWGQGTTVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKT
HTCPPCPAPEAAGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 18)

Anti-EGFR Ab No. 3 Heavy Chain L234A, L235A, L328C
QVQLQQSGAEVKKPGSSVKVSCKASGYTFTNYYIYWVRQAPGQGLEWIGGINPTSGGSNFNEKFKTRVTITADESS
TTAYMELSSLRSEDTAFYFCTRQGLWFDSDGRGFDFWGQGTTVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVDGVEVHNAKTKPREEQYNST TABLE VI-continued Antibody Sequences YRVVSVLTVLHQDWLNGKEYKCKVSNKACPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ
ID NO: 19)

Anti-EGFR Ab No. 3 Light Chain Wild Type
DIQMTQSPSSLSASVGDRVTITCRSSQNIVHSNGNTYLDWYQQTPGKAPKLLIYKVSNRFSGVPSRFSGSGSGTDFT
FTISSLQPEDIATYYCFQYSHVPWTFGQGTKLQITREVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC (SEQ ID NO: 20)

Anti-Trop2 Ab Heavy Chain Wild Type
QVQLQQSGSELKKPGASVKVSCKASGYTFTNYGMNWVKQAPGQGLKWMGWINTYTGEPTYTDDFKGRFAFSLD
TSVSTAYLQISSLKADDTAVYFCARGGFGSSYWYFDVWGQGSLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 21)

Anti-Trop2 Ab Heavy Chain L328C
QVQLQQSGSELKKPGASVKVSCKASGYTFTNYGMNWVKQAPGQGLKWMGWINTYTGEPTYTDDFKGRFAFSLD
TSVSTAYLQISSLKADDTAVYFCARGGFGSSYWYFDVWGQGSLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKACPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ
ID NO: 22)

Anti-Trop2 Ab Heavy Chain L234A, L235A
QVQLQQSGSELKKPGASVKVSCKASGYTFTNYGMNWVKQAPGQGLKWMGWINTYTGEPTYTDDFKGRFAFSLD
TSVSTAYLQISSLKADDTAVYFCARGGFGSSYWYFDVWGQGSLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 23)

Anti-Trop2 Ab Heavy Chain L234A, L235A, L328C
QVQLQQSGSELKKPGASVKVSCKASGYTFTNYGMNWVKQAPGQGLKWMGWINTYTGEPTYTDDFKGRFAFSLD
TSVSTAYLQISSLKADDTAVYFCARGGFGSSYWYFDVWGQGSLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVDGVEVHNAKTKPREEQYNST
YRVVSVLTVLHQDWLNGKEYKCKVSNKACPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ
ID NO: 24)

Anti-Trop2 Ab Light Chain Wild Type
DIQLTQSPSSLSASVGDRVSITCKASQDVSIAVAWYQQKPGKAPKLLIYSASYRYTGVPDRFSGSGSGTDFTLTISSLQ
PEDFAVYYCQQHYITPLTFGAGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC (SEQ ID NO: 25)

Anti-CDH3 Ab Heavy Chain Wild Type
QVQLQQSGPGLVKPSQTLSLTCAISGDSVSSQSAAWNWIRQSPSRGLEWLGRIYYRSKWYNDYALSVKSRITINPD
TSKNQFSLQLNSVTPEDTAVYYCARGEGYGREGFAIWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKRVEPKSCDKTH
TCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 26)

Anti-CDH3 Ab Heavy Chain L328C
QVQLQQSGPGLVKPSQTLSLTCAISGDSVSSQSAAWNWIRQSPSRGLEWLGRIYYRSKWYNDYALSVKSRITINPD
TSKNQFSLQLNSVTPEDTAVYYCARGEGYGREGFAIWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKRVEPKSCDKTH
TCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKACPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 27)

Anti-CDH3 Ab Heavy Chain L234A, L235A
QVQLQQSGPGLVKPSQTLSLTCAISGDSVSSQSAAWNWIRQSPSRGLEWLGRIYYRSKWYNDYALSVKSRITINPD
TSKNQFSLQLNSVTPEDTAVYYCARGEGYGREGFAIWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKRVEPKSCDKTH
TCPPCPAPEAAGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 28)

TABLE VI-continued

Antibody Sequences

Anti-CDH3 Ab Heavy Chain L234A, L235A, L328C
QVQLQQSGPGLVKPSQTLSLTCAISGDSVSSQSAAWNWIRQSPSRGLEWLGRIYYRSKWYNDYALSVKSRITINPD
TSKNQFSLQLNSVTPEDTAVYYCARGEGYGREGFAIWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKRVEPKSCDKTH
TCPPCPAPEAAGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKACPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 29)

Anti-CDH3 Ab Light Chain Wild Type
DIQMTQSPSSLSASVGDRVTITCRASQTISNTLAWYQQKPGKAPKLLIYAASNLQSGVPSRFSGSGSGTDFTLTISSL
QPEDFATYYCQQYLSWFTFGQGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC (SEQ ID NO: 30)

TABLE VII

Antibody Fragments and Confidence Scores of Resulting Peptide Mapping for Single Mutant of anti-EGFR mAb No. 1.

| Heavy Chain Sequence | Modifications | XCorr | Charge | MH+ [Da] | ΔM [ppm] |
| --- | --- | --- | --- | --- | --- |
| ScDKTHTcPPcPAPEAAGGPSVFLFPPKPK | C2(Carbamidomethyl); C8(Carbamidomethyl); C11(Carbamidomethyl) | 6.60 | 4 | 3250.55434 | 1.83 |
| VTGAFDIWGQGTMVTVSSASTK | | 6.55 | 2 | 2243.10307 | 0.76 |
| THTcPPcPAPEAAGGPSVFLFPPKPK | C4(Carbamidomethyl); C7(Carbamidomethyl) | 6.47 | 3 | 2760.36362 | −0.06 |
| TPEVTcVVVDVSHEDPEVK | C6(Carbamidomethyl) | 5.25 | 3 | 2139.03019 | 1.24 |
| GFYPSDIAVEWESNGQPENNYK | | 4.91 | 2 | 2544.13384 | 0.93 |
| SRWQQGNVFScSVMHEALHNHYTQK | C11(Carbamidomethyl) | 4.68 | 5 | 3044.40595 | 1.84 |
| THTcPPCPAPEAAGGPSVF | C4(Carbamidomethyl); C7(Carbamidomethyl) | 4.40 | 2 | 1952.86479 | 0.90 |
| VFScSVMHEALHNHYTQK | C4(Carbamidomethyl) | 4.03 | 4 | 2188.00844 | 0.97 |
| FNWYVDGVEVHNAK | | 3.94 | 3 | 1677.80436 | 1.38 |
| THTcPPcPAPEAAGGPSVFLFPPK | C4(Carbamidomethyl); C7(Carbamidomethyl) | 3.93 | 3 | 2535.21146 | −1.81 |
| WQQGNVFScSVMHEALHNHYTQK | C9(Carbamidomethyl) | 3.75 | 5 | 2801.26875 | 0.55 |
| MHEALHNHYTQK | | 3.72 | 3 | 1508.71268 | 4.20 |
| WYVDGVEVHNAK | | 3.69 | 2 | 1416.70049 | 6.91 |
| ScDKTHTcPPcPAPEAAGGPSVF | C2(Carbamidomethyl); C8(Carbamidomethyl); C11(Carbamidomethyl) | 3.66 | 3 | 2443.05136 | 1.52 |
| YVDGVEVHNAK | | 3.54 | 2 | 1230.61699 | 4.57 |
| IcNVNHKPSNTK | C2(Carbamidomethyl) | 3.52 | 4 | 1411.71242 | 0.93 |
| WQQGNVFScSVmHEALHNHYTQK | C9(Carbamidomethyl); M12(Oxidabon) | 3.51 | 4 | 2817.26357 | 0.52 |
| STSGGTAALGcLVK | C11(Carbamidomethyl) | 3.50 | 2 | 1321.67266 | −4.12 |
| GQPREPQVYTLPPSR | | 3.48 | 3 | 1724.90805 | 0.08 |
| ScSVMHEALHNHYTQK | C2(Carbamidomethyl) | 3.47 | 3 | 1941.86899 | −0.25 |
| EVTcVCCDVSHEDPEVK | C4(Carbamidomethyl) | 3.40 | 3 | 1940.92600 | −0.55 |
| ePQVYTLPPSREEMTK | N-Term(Gln → pyro-Glu) | 3.24 | 3 | 1887.91367 | −1.11 |
| qVQLQESGPGLVK | N-Term(Gln → pyro-Glu) | 3.23 | 2 | 1365.74162 | 3.15 |

TABLE VII-continued

Antibody Fragments and Confidence Scores of Resulting Peptide Mapping for Single Mutant of anti-EGFR mAb No. 1.

| | | | | | |
|---|---|---|---|---|---|
| GQPREPQVYTLPPSREEMTK | | 3.18 | 4 | 2343.17544 | −0.35 |
| TVLHQDWLNGK | | 3.11 | 2 | 1310.69036 | 3.92 |
| IcNVNHKPSNTKVDK | C2(Carbamidomethyl) | 3.11 | 3 | 1753.90299 | 0.88 |
| TTPPVLDSDGSFFLYSK | | 3.07 | 2 | 1873.92363 | 0.93 |
| VVSVLTVLHQDWLNGK | | 3.03 | 2 | 1808.01262 | 3.35 |
| GPSVFPLAPSSK | | 2.84 | 2 | 1186.64751 | 0.67 |
| HQDWLNGK | | 2.70 | 2 | 997.48625 | 1.22 |
| SVMHEALHNHYTQK | | 2.68 | 4 | 1694.80666 | −0.08 |
| EPQVYTLPPSREEMTK | | 2.67 | 3 | 1904.94852 | 3.25 |
| WSVLTVLHQDWLNGKEYK | | 2.64 | 3 | 2228.21006 | 1.16 |
| cNVNHKPSNTK | N-Term(Gln → pyro-Glu); C1(Carbamidomethyl) | 2.63 | 3 | 1281.60102 | 0.41 |
| AKGQPREPQVYTLPPSR | | 2.60 | 4 | 1924.04104 | 0.54 |
| TSGGTAALGcLVK | C10(Carbamidomethyl) | 2.57 | 2 | 1234.65386 | 6.31 |
| LHQDWLNGK | | 2.52 | 2 | 1110.56560 | −3.16 |
| cNVNHKPSNTK | C1(Carbamidomethyl) | 2.48 | 3 | 1298.62781 | 0.60 |
| GGPSVFLFPPKPK | | 2.47 | 2 | 1370.78435 | 0.87 |
| DKTHTcPPcPAPEAAGGPSVFLFPPKPK | C6(Carbamidomethyl); C9(Carbamidomethyl) | 2.44 | 5 | 3003.48554 | −0.05 |
| IcNVNHKPSNTKVDKK | C2(Carbamidomethyl) | 2.40 | 5 | 1881.99628 | −0.07 |
| FNWYVDGVEVH | | 2.39 | 2 | 1364.62895 | 1.42 |
| SGNTNYNPSLK | | 2.36 | 2 | 1194.57561 | 0.53 |
| VLHQDWLNGK | | 2.35 | 3 | 1209.63700 | −0.44 |
| NQVSLTcLVK | C7(Carbamidomethyl) | 2.34 | 2 | 1161.63066 | 0.86 |
| EPQVYTLPPSREmTK | M14(Oxidation) | 2.34 | 3 | 1920.93875 | 0.79 |
| cVVVDVSHEDPEVK | N-Term(Gln → pyro-Glu); C1(Carbamidomethyl) | 2.34 | 2 | 1594.74370 | 1.17 |
| qGNVFSCSVMHEALHNHYTQK | N-Term(Gln → pyro-Glu); C7(Carbamidomethyl) | 2.27 | 4 | 2470.10976 | 2.84 |
| GTAALGcLVK | C7(Carbamidomethyl) | 2.27 | 2 | 989.54595 | 1.07 |
| fNWYVDGVEVHNAK | N-Term(Gln → pyro-Glu) | 2.27 | 2 | 1660.77812 | 1.58 |
| SVLTVLHQDWLNGK | | 2.26 | 2 | 1609.87578 | 3.76 |
| qVQLQESGPGLVKPSETL | N-Term(Gln → pyro-Glu) | 2.25 | 2 | 1892.99919 | 1.44 |
| PEAAGGPSVFLFPPKPK | | 2.25 | 2 | 1738.96257 | 5.64 |
| PEVTcVVVDVSHEDPEVK | C5(Carbamidomethyl) | 2.15 | 3 | 2037.98178 | 0.95 |
| VMHEALHNHYTQK | | 2.13 | 4 | 1607.78066 | 3.67 |
| FNWYVDGVEVHN | | 2.13 | 2 | 1470.67217 | 1.50 |
| NWYVDGVEVHNAK | | 2.13 | 2 | 1530.74016 | 4.27 |
| DRVTGAFDIWGQGTMVTVSSASTK | | 2.12 | 3 | 2514.23526 | 2.32 |
| MVTVSSASTK | | 2.11 | 2 | 1010.51879 | 0.06 |

TABLE VII-continued

Antibody Fragments and Confidence Scores of Resulting Peptide Mapping for Single Mutant of anti-EGFR mAb No. 1.

| | | | | | |
|---|---|---|---|---|---|
| SRWQQGNVF | | 2.09 | 2 | 1121.54936 | 0.58 |
| QVSLTcLVK | C6(Carbamidomethyl) | 2.03 | 2 | 1047.58537 | −1.30 |
| VVVDVSHEDPEVK | | 2.01 | 3 | 1451.73648 | −0.85 |
| LTISIDTSK | | 2.01 | 2 | 977.55144 | 0.05 |
| TKPREEQYNSTYR | | 2.00 | 4 | 1671.80764 | −0.55 |

| Light Chain Sequence | Modifications | XCorr | Charge | MH+ [Da] | ΔM [ppm] |
|---|---|---|---|---|---|
| VDNALQSGNSQESVTEQDSK | | 5.42 | 2 | 2135.96855 | −0.12 |
| DIQmTQSPSSLSASVGDR | M4(Oxidation) | 4.67 | 2 | 1894.88262 | 0.75 |
| RTVAAPSVFIFPPSDEQLK | | 4.41 | 3 | 2102.13095 | 1.32 |
| TVAAPSVFIFPPSDEQLK | | 4.30 | 2 | 1946.03008 | 1.55 |
| HKVYAcEVTHQGLSSPVTK | C6(Carbamidomethyl) | 4.30 | 4 | 2141.07485 | −2.81 |
| VTTTcQASQDISNYLNWYQQKPGK | C5(Carbamidomethyl) | 4.24 | 3 | 2842.38736 | 1.56 |
| LLIYDASNLETGVPSR | | 4.09 | 2 | 1747.92595 | 1.94 |
| DIQMTQSPSSLSASVGDR | | 4.06 | 2 | 1878.88994 | 1.95 |
| VDNALQSGNSQESVTEQDSKDSTYSLSSTLTLSK; | | 3.64 | 3 | 3619.71457 | 1.41 |
| FcQHFDHLPLAFGGGTK | C2(Carbamidomethyl) | 3.57 | 3 | 1931.92472 | 1.31 |
| VYAcEVTHQGLSSPVTK | C4(Carbamidomethyl) | 3.44 | 3 | 1875.92704 | 0.03 |
| AcEVTHQGLSSPVTK | C2(Carbamidomethyl) | 3.41 | 2 | 1613.79631 | 0.66 |
| vDNALQSGNSQESVTEQDSK | N-Term(Gln → pyro-Glu) | 3.40 | 2 | 2118.94292 | 0.31 |
| SPSSLSASVGDR | | 3.20 | 2 | 1162.57573 | 5.01 |
| SGTASVVcLLNNFYPR | C8(Carbamidomethyl) | 3.17 | 2 | 1797.89812 | 1.57 |
| LNWYQQKPGKAPK | | 3.15 | 3 | 1557.85746 | 2.42 |
| eAKVQWKVDNALQSGNSQESVTEQDSK | N-Term(Gln → pyro-Glu) | 3.14 | 4 | 2988.40053 | −5.93 |
| DSTYSLSSTLTLSK | | 3.13 | 2 | 1502.76091 | 1.62 |
| DIQMTQSPSSL | | 3.05 | 2 | 1206.56743 | 0.25 |
| HKVYAcEVTHQGL | C6(Carbamidomethyl) | 3.01 | 3 | 1541.75260 | −0.24 |
| PPSDEQLK | | 2.86 | 2 | 913.46160 | −1.08 |
| qSPSSLSASVGDR | N-Term(Gln → pyro-Glu) | 2.83 | 2 | 1273.60100 | −0.74 |
| qASQDISNYLNWYQQKPGK | N-Term(Gln → pyro-Glu) | 2.79 | 3 | 2251.08304 | 2.29 |
| VTITcQASQDISNYLNW | C5(Carbamidomethyl) | 2.62 | 2 | 2012.94023 | 0.97 |
| cQHFDHLPLAFGGGTK | C1(Carbamidomethyl) | 2.61 | 3 | 1784.84745 | −3.55 |
| qDISNYLNWYQQKPGK | N-Term(Gln → pyro-Glu) | 2.44 | 2 | 1964.95134 | 0.61 |
| DIQMTQSPSSLSA | | 2.40 | 2 | 1364.63786 | 1.16 |
| qGLSSPVTK | N-Term(Gln → pyro-Glu) | 2.39 | 2 | 899.48204 | −1.41 |
| VYAcEVTHQGL | C4(Carbamidomethyl) | 2.32 | 2 | 1276.59770 | −1.08 |
| LNWYQQKPGK | | 2.22 | 3 | 1261.67118 | 1.87 |
| WYQQKPGK | | 2.21 | 2 | 1034.53960 | −2.15 |
| QSPSSLSASVGDR | | 2.18 | 2 | 1290.62883 | 0.26 |

TABLE VII-continued

Antibody Fragments and Confidence Scores of Resulting Peptide Mapping for Single Mutant of anti-EGFR mAb No. 1.

| | | | | | |
|---|---|---|---|---|---|
| ADYEKHKVYAcEVTHQGLSSPVTK | C11(Carbamidomethyl) | 2.17 | 5 | 2747.34357 | −0.82 |
| VTITcQASQDISNY | C5(Carbamidomethyl) | 2.08 | 2 | 1599.73369 | 1.08 |
| INWYQQKPGK | N-Term(Gln → pyro-Glu) | 2.06 | 3 | 1244.64603 | 3.02 |
| KVDNALQSGNSQESVTEQDSK | | 2.05 | 2 | 2264.06157 | −0.98 |
| IFPPSDEQLK | | 2.00 | 2 | 1173.61199 | −2.63 |
| SLSASVGDR | | 2.00 | 2 | 891.45268 | −0.45 |

TABLE VIII

Antibody Fragments and Confidence Scores of Resulting Peptide Mapping for Triple Mutant of anti-EGFR mAb No. 1. Note, "*" denotes the peptide with the site of conjugation.

| Heavy Chain Sequence | Modifications | XCorr | Charge | MH+ [Da] | ΔM [ppm] |
|---|---|---|---|---|---|
| THTcPPcPAPEAAGGPSVFLFPPKPK | C4(Carbamidomethyl); C7(Carbamiddmethyl) | 7.39 | 3 | 2760.36710 | 1.20 |
| TPEVTcVVVDVSHEDPEVK | C6(Carbamidomethyl) | 5.66 | 3 | 2139.03000 | 1.16 |
| ScDKTHTcPPcPAPEAAGGPSVFLFPPKPK | C2(Carbamidomethyl); C8(Carbamidomethyl); C11(Carbamidomethyl) | 5.50 | 4 | 3250.55410 | 1.76 |
| GFYPSDIAVEWESNGQPENNYK | | 4.79 | 2 | 2544.13262 | 0.45 |
| VVSVLTVLHQDWLNGKEYK | | 4.73 | 4 | 2228.21401 | 2.94 |
| WQQGNVFScSVMHEALHNHYTQK | C9(Carbamidomethyl) | 4.58 | 4 | 2801.25576 | −4.08 |
| VVSVLTVLHQDWLNGK | | 4.36 | 2 | 1808.01164 | 2.81 |
| THTcPPcPAPEAAGGPSVF | C4(Carbamidomethyl); C7(Carbamidomethyl) | 4.25 | 2 | 1952.86479 | 0.90 |
| cNVNHKPSNTKVDK | C1(Carbamidomethyl) | 4.14 | 4 | 1640.81948 | 1.28 |
| FNWYVDGVEVHNAK | | 4.09 | 3 | 1677.80472 | 1.60 |
| cSVMHEALHNHYTQK | C1(Carbamidomethyl) | 4.08 | 4 | 1854.84047 | 1.63 |
| WYVDGVEVHNAK | | 3.85 | 2 | 1416.68852 | −1.53 |
| ScDKTHTcPPcPAPEAAGGPSVF | C2(Carbamidomethyl); C8(Carbamidomethyl); C11(Carbamidomethyl) | 3.84 | 3 | 2443.05173 | 1.67 |
| VTGAFDIWGQGTMVTVSSASTK | | 3.83 | 3 | 2243.10843 | 3.15 |
| TPEVTcVVVDVSHED | C6(Carbamidomethyl) | 3.83 | 2 | 1685.76958 | 0.48 |
| GQPREPQVYTLPPSR | | 3.69 | 3 | 1724.91098 | 1.78 |
| YVDGVEVHNAK | | 3.64 | 2 | 1230.61040 | −0.79 |
| SRWQQGNVFSCSVMHEALHNHYTQK | C11(Carbamidomethyl) | 3.55 | 5 | 3044.40229 | 0.64 |
| IcNVNHKPSNTKVDKK | C2(Carbamidomethyl) | 3.49 | 5 | 1881.99720 | 0.42 |
| nQVSLTcLVK | N-Term(Gln → pyro-Glu); C7(Carbamidomethyl) | 3.45 | 2 | 1144.60796 | 4.23 |
| STSGGTAALGCLVK | C11(Carbamidomethyl) | 3.45 | 2 | 1321.67778 | −0.24 |
| SVLTVLHQDWLNGK | | 3.44 | 2 | 1609.87370 | 2.47 |
| GQPREPQVYTLPPSREEMTK | | 3.25 | 4 | 2343.17592 | −0.14 |
| GPSVFPLAPSSK | | 3.23 | 2 | 1186.64739 | 0.57 |

TABLE VIII-continued

Antibody Fragments and Confidence Scores of Resulting Peptide Mapping for Triple Mutant of anti-EGFR mAb No. 1. Note, "*" denotes the peptide with the site of conjugation.

| | | | | | |
|---|---|---|---|---|---|
| ePQVYTLPPSREEMTK | N-Term(Gln → pyro-Glu) | 3.20 | 3 | 1887.92667 | 5.77 |
| VSNKAcPAPIEK* | C6(Carbamidomethyl) | 3.16 | 2 | 1313.69072 | 1.87 |
| IcNVNHKPSNTK | C2(Carbamidomethyl) | 3.12 | 4 | 1411.71218 | 0.76 |
| TSGGTAALGcLVK | C10(Carbamidomethyl) | 3.09 | 2 | 1234.65105 | 4.04 |
| ScSVmHEALHNHYTQK | C2(Carbamidomethyl); M5(Oxidation) | 3.09 | 4 | 1957.86367 | -0.37 |
| GGPSVFLFPPKPK | | 3.01 | 2 | 1370.78752 | 3.18 |
| wQQGNVFScSVMHEALHNHYTQK | N-Term(Gln → pyro-Glu); C9(Carbamidomethyl) | 2.98 | 5 | 2784.25367 | 4.68 |
| IcNVNHKPSNTKVDK | C2(Carbamidomethyl) | 2.92 | 3 | 1753.90171 | 0.15 |
| SGNTNYNPSLK | | 2.91 | 2 | 1194.57671 | 1.45 |
| EPQVYTLPPSREEMTK | | 2.86 | 2 | 1904.94658 | 2.24 |
| qVQLQESGPGLVK | N-Term(Gln → pyro-Glu) | 2.85 | 2 | 1365.74468 | 5.38 |
| fNWYVDGVEVHNAK | N-Term(Gln → pyro-Glu) | 2.77 | 2 | 1660.77764 | 1.29 |
| EVTcVVVDVSHEDPEVK | C4(Carbamidomethy) | 2.74 | 3 | 1940.92545 | -0.84 |
| GGTAALGcLVK | C8(Carbamidomethyl) | 2.58 | 2 | 1046.56560 | -0.72 |
| AKGQPREPQVYTLPPSR | | 2.55 | 3 | 1924.04276 | 1.43 |
| TTPPVLDSDGSFFLYSK | | 2.54 | 2 | 1873.92668 | 2.56 |
| NQVSLTcLVK | C7(Carbamidomethyl) | 2.52 | 2 | 1161.63188 | 1.91 |
| SVMHEALHNHYTQK | | 2.47 | 4 | 1694.80886 | 1.22 |
| NWYVDGVEVHNAK | | 2.44 | 2 | 1530.73760 | 2.60 |
| PEAAGGPSVFLFPPKPK | | 2.42 | 2 | 1738.94597 | -3.91 |
| SSLGTQTYIcNVNHKPSNTK | C10(Carbamidomethyl) | 2.37 | 4 | 2249.09975 | 0.79 |
| cPAPIEK | C1(Carbamidomethyl) | 2.37 | 2 | 814.41460 | 2.21 |
| tcVVVDVSHEDPEVKFNWYVDGVEVHNAK | N-Term(Gln → pyro-Glu); C2(Carbamidomethyl) | 2.30 | 3 | 3354.59543 | 6.48 |
| EPQVYTLPPSREEmTK | M14(Oxidation) | 2.29 | 3 | 1920.93839 | 0.60 |
| cNVNHKPSNTK | C1(Carbamidomethyl) | 2.28 | 3 | 1298.63092 | 2.99 |
| EEMTKNQVSLTcLVK | C12(Carbamidomethyl) | 2.28 | 3 | 1779.90433 | 3.55 |
| VLHQDWLNGK | | 2.26 | 3 | 1209.63782 | 0.24 |
| AcPAPIEKTISKAK* | C2(Carbamidomethyl) | 2.23 | 4 | 1513.84084 | 0.06 |
| EPQVYTLPPSR | | 2.22 | 2 | 1286.67912 | 4.01 |
| LHQDWLNGK | | 2.21 | 2 | 1110.56914 | 0.03 |
| LSSVTAADTAIYYcVR | C14(Carbamidomethyl) | 2.21 | 2 | 1789.88237 | 1.90 |
| VDGVEVHNAK | | 2.20 | 2 | 1067.54704 | -0.94 |
| PEVTcVVVDVSHEDPEVK | C5(Carbamidomethyl) | 2.20 | 3 | 2037.98288 | 1.49 |
| EEmTKNQVSLTcLVK | M3(Oxidation); C12(Carbamidomethyl) | 2.19 | 3 | 1795.89530 | 1.32 |
| DGVEVHNAK | | 2.18 | 2 | 968.48192 | 2.36 |
| HQDWLNGK | | 2.16 | 2 | 997.48693 | 1.89 |

TABLE VIII-continued

Antibody Fragments and Confidence Scores of Resulting Peptide Mapping for Triple Mutant of anti-EGFR mAb No. 1. Note, "*" denotes the peptide with the site of conjugation.

| | | | | | |
|---|---|---|---|---|---|
| FNWYVDGVEVH | | 2.16 | 2 | 1364.62871 | 1.24 |
| IYYSGNTNYNPSLK | | 2.14 | 2 | 1633.78142 | -2.61 |
| LTISIDTSK | | 2.08 | 2 | 977.54796 | -3.51 |
| QVSLTcLVK | C6(Carbamidomethyl) | 2.03 | 2 | 1047.58293 | -3.63 |
| PPSREEMTK | | 2.03 | 2 | 1074.52556 | 0.63 |

| Light Chain Sequence | Modifications | XCorr | Charge | MH+ [Da] | ΔM [ppm] |
|---|---|---|---|---|---|
| VTITcQASQDISNYLNWYQQKPGK | C5(Carbamidomethyl) | 5.83 | 3 | 2842.38791 | 1.75 |
| eAKVQWKVDNALQSGNSQESVTEQDSK | N-Term(Gln → pyro-Glu) | 4.91 | 4 | 2988.40835 | -3.31 |
| DIQmTQSPSSLSASVGDR | M4(Oxidation) | 4.91 | 2 | 1894.88396 | -1.46 |
| VDNALQSGNSQESVTEQDSK | | 4.79 | 2 | 2135.96758 | -0.58 |
| DIQMTQSPSSLSASVGDR | | 4.24 | 2 | 1878.88860 | 1.24 |
| RTVAAPSVFIFPPSDEQLK | | 4.23 | 3 | 2102.13059 | 1.15 |
| SGTASVVcLLNNFYPR | C8(Carbamidomethyl) | 4.20 | 2 | 1797.89861 | 1.84 |
| VTTTcQASQDISNYLNWYQQKPGKAPK | C5(Carbamidomethyl) | 4.07 | 4 | 3138.57168 | 1.24 |
| LLIYDASNLETGVPSR | | 4.02 | 2 | 1747.92705 | 2.57 |
| HKVYAcEVTHQGLSSPVTK | C6(Carbamidomethyl) | 3.90 | 4 | 2141.08266 | 0.84 |
| TVAAPSVFIFPPSDEQLK | | 3.87 | 2 | 1946.03081 | 1.93 |
| VYAcEVTHQGLSSPVTK | C4(Carbamidomethyl) | 3.80 | 3 | 1875.92557 | -0.75 |
| VDNALQSGNSQESVTEQDSKDSTYSLSSTLTLSK | | 3.61 | 3 | 3619.71640 | 1.92 |
| DSTYSLSSTLTLSK | | 3.39 | 2 | 1502.76250 | 2.67 |
| HKVYAcEVTHQGL | C6(Carbamidomethyl) | 3.19 | 3 | 1541.75260 | -0.24 |
| LNWYQQKPGKAPK | | 3.17 | 3 | 1557.85251 | -0.75 |
| SPSSLSASVGDR | | 3.12 | 2 | 1162.57341 | 3.01 |
| DIQMTQSPSSL | | 2.98. | 2 | 1206.56523 | -1.57 |
| PPSDEQLK | | 2.95 | 2 | 913.46257 | -0.01 |
| qDISNYLNWYQQKPGK | N-Term(Gln → pyro-Glu) | 2.95 | 2 | 1964.94902 | -0.58 |
| FcQHFDHLPLAFGGGTK | C2(Carbamidomethyl) | 2.85 | 4 | 1931.92251 | 0.16 |
| VQWKVDNALQSGNSQESVTEQDSKDSTYSLSSTLTLSK | | 2.78 | 4 | 4161.01479 | 0.97 |
| qGLSSPVTK | N-Term(Gln → pyro-Glu) | 2.67 | 2 | 899.48210 | -1.34 |
| qASQDISNYLNWYQQKPGK | N-Term(Gln → pyro-Glu) | 2.63 | 2 | 2251.08330 | 2.41 |
| VYAcEVTHQGL | C4(Carbamidomethyl) | 2.58 | 2 | 1276.59905 | -0.03 |
| LLIYDASNLETGVPSRF | | 2.51 | 2 | 1894.99394 | 1.56 |
| DIQMTQSPSSLSA | | 2.47 | 2 | 1364.63750 | 0.89 |
| AcEVTHQGLSSPVTK | C2(Carbamidomethyl) | 2.38 | 3 | 1613.79654 | 0.80 |
| VTITcQASQDISNYLNW | C5(Carbamidomethyl) | 2.36 | 2 | 2012.94121 | 1.46 |
| VDNALQSGNSQESVTEQDSKDSTY | | 2.30 | 2 | 2602.13994 | 0.44 |

TABLE VIII-continued

Antibody Fragments and Confidence Scores of Resulting Peptide Mapping for Triple Mutant of anti-EGFR mAb No. 1. Note, "*" denotes the peptide with the site of conjugation.

| | | | | |
|---|---|---|---|---|
| LNWYQQKPGK | 2.28 | 3 | 1261.67154 | 2.16 |
| ALQSGNSQESVTEQDSK | 2.28 | 2 | 1807.83879 | 4.58 |
| SNLETGVPSR | 2.06 | 2 | 1059.54436 | 1.32 |

The invention claimed is:

1. An antibody composition comprising, a triple amino acid mutation, wherein the triple amino acid mutation comprises a L234A modification, a L235A modification, and a L328C modification, wherein the amino acid mutation position numbering is according to the EU index as set forth in Kabat, and wherein said triple amino acid mutation suppresses binding to FcγRI, FcγRIIA, and FcγRIIIA and reduces antibody-dependent cellular cytotoxicity (ADCC) and wherein said triple mutation further reduces C1q binding and reduces complement-dependent cytotoxicity (CDC).

2. The antibody of claim 1, wherein the antibody comprises an EGFR antibody.

3. The antibody of claim 1, wherein the antibody comprises a Her2 antibody.

4. The antibody of claim 1, wherein the antibody comprises a Trop2 antibody.

5. The antibody of claim 1, wherein the antibody comprises a CDH3 antibody.

6. The antibody of claim 1, wherein the antibody comprises a tumor associated antigen (TAA) antibody.

7. The antibody of claim 6, wherein the TAA is selected from the group consisting of GPNMB, DLL3, ENPP3, SLITRK6, CA9, PSMA, CDH6, Glypican 3, EDNRB, NECTIN-4, SLC34A2, Her3, and NRP-1.

8. An article of manufacture comprising the antibody of claim 1.

9. A pharmaceutical composition comprising a therapeutically effective amount of the antibody of claim 1, and a pharmaceutically acceptable excipient.

10. An antibody-drug-conjugate (ADC) comprising,
   (i) antibody composition comprising, a triple amino acid mutation, wherein the triple amino acid mutation comprises a L234A modification, a L235A modification, and a L328C modification, wherein the amino acid mutation position numbering is according to the EU index as set forth in Kabat, and wherein said triple amino acid mutation suppresses binding to FcγRI, FcγRIIA, and FcγRIIIA and reduces antibody-dependent cellular cytotoxicity (ADCC) and wherein said triple mutation further reduces C1g binding and reduces complement-dependent cytotoxicity (CDC);
   (ii) a linker; and
   (iii) a drug unit, wherein said drug unit is conjugated specifically at site L328C.

11. The ADC of claim 10, wherein the antibody composition comprises an EGFR antibody.

12. The ADC of claim 10, wherein the antibody composition comprises an Her2 antibody.

13. The ADC of claim 10, wherein the antibody composition comprises an Trop2 antibody.

14. The ADC of claim 10, wherein the antibody comprises a CDH3 antibody.

15. The ADC of claim 10, wherein the antibody composition comprises a tumor associated antigen (TAA) antibody.

16. The ADC of claim 15, wherein the TAA is selected from the group consisting of GPNMB, DLL3, ENPP3, SLITRK6, CA9, PSMA, CDH6, Glypican 3, EDNRB, NECTIN-4, SLC34A2, Her3, and NRP.

17. The ADC of claim 10, further comprising a stretcher unit.

18. The ADC of claim 10, further comprising a spacer unit.

19. The ADC of claim 10, further comprising an amino acid unit, wherein the amino acid unit links the spacer unit to the stretcher unit.

20. An article of manufacture comprising the ADC of claim 10.

21. A pharmaceutical composition comprising a therapeutically effective amount of the ADC of claim 10, and a pharmaceutically acceptable excipient.

22. An antibody-boron-conjugate (ABC) comprising,
   (i) an antibody composition comprising, a triple amino acid mutation, wherein the triple amino acid mutation comprises a L234A modification, a L235A modification, and a L328C modification, wherein the amino acid mutation position numbering is according to the EU index as set forth in Kabat, and wherein said triple amino acid mutation suppresses binding to FcγRI, FcγRIIA, and FcγRIIIA and reduces antibody-dependent cellular cytotoxicity (ADCC) and wherein said triple mutation further reduces C1q binding and reduces complement-dependent cytotoxicity (CDC);
   (ii) a linker; and
   (iii) a drug unit, wherein said drug unit comprises a borylated composition, and wherein said drug unit is conjugated specifically at site L328C.

23. The ABC of claim 22, wherein the antibody composition comprises an EGFR antibody.

24. The ABC of claim 22, wherein the antibody composition comprises an Her2 antibody.

25. The ABC of claim 22, wherein the antibody composition comprises a Trop2 antibody.

26. The ABC of claim 22, wherein the antibody composition comprises a CDH3 antibody.

27. The ABC of claim 22, wherein the antibody composition comprises a tumor associated antigen (TAA) antibody.

28. The antibody of claim 27, wherein the TAA is selected from the group consisting of GPNMB, DLL3, ENPP3, SLITRK6, CA9, PSMA, CDH6, Glypican 3, EDNRB, NECTIN-4, SLC34A2, Her3, and NRP-1.

29. The ABC of claim 22, further comprising a stretcher unit, wherein the stretcher unit links the antibody unit to an amino acid unit.

30. The ABC of claim 22, further comprising a spacer unit, wherein the spacer unit links a stretcher unit to a drug unit.

31. The ABC of claim 22, further comprising an amino acid unit, wherein the amino acid unit links the spacer unit to the stretcher unit.

32. A pharmaceutical composition comprising a therapeutically effective amount of the ABC of claim 22, and a pharmaceutically acceptable excipient.

33. A method of treating cancer in an individual comprising,
   (i) administering to said individual a therapeutically effective amount of the ABC of claim 22, wherein the cancer is selected from the group consisting of acute myeloid leukemia, adrenocortical carcinoma, adult t-cell leukemia/lymphoma, B-cell Hodgkin's lymphoma, bladder, breast, renal cell carcinoma, colorectal, gastric, head and neck, multiple myeloma, non-small cell lung cancer, ovarian, pancreatic, prostate, genital, cervical, esophageal, and glioma.

* * * * *